US009879280B2

(12) United States Patent
Gomez Sebastian et al.

(10) Patent No.: US 9,879,280 B2
(45) Date of Patent: Jan. 30, 2018

(54) BACULOVIRUS SYSTEM FOR EXPRESSING PROTEINS FORMING VIRUS-LIKE PARTICLES

(71) Applicant: ALTERNATIVE GENE EXPRESSION S.L., Madrid (ES)

(72) Inventors: Silvia Gomez Sebastian, Madrid (ES); Javier López Vidal, Madrid (ES); José Angel Martinez Escribano, Madrid (ES)

(73) Assignee: ALTERNATIVE GENE EXPRESSION S.L., Madrid (ES)

( * ) Notice: Subject to any disclaimer, the term of this patent is extended or adjusted under 35 U.S.C. 154(b) by 0 days.

(21) Appl. No.: 14/649,500

(22) PCT Filed: Dec. 6, 2013

(86) PCT No.: PCT/EP2013/075812
§ 371 (c)(1),
(2) Date: Jun. 3, 2015

(87) PCT Pub. No.: WO2014/086981
PCT Pub. Date: Jun. 12, 2014

(65) Prior Publication Data
US 2015/0307899 A1 Oct. 29, 2015

(30) Foreign Application Priority Data

Dec. 7, 2012 (EP) .................................. 12196120

(51) Int. Cl.
| | | |
|---|---|---|
| *C07H 21/04* | (2006.01) | |
| *C12N 5/00* | (2006.01) | |
| *C12N 7/00* | (2006.01) | |
| *C12N 15/00* | (2006.01) | |
| *C12P 21/06* | (2006.01) | |
| *C12N 15/86* | (2006.01) | |
| *C07K 14/005* | (2006.01) | |
| *C12N 15/85* | (2006.01) | |

(52) U.S. Cl.
CPC ............ *C12N 15/86* (2013.01); *C07K 14/005* (2013.01); *C12N 7/00* (2013.01); *C12N 15/85* (2013.01); *C07H 21/04* (2013.01); *C12N 2502/00* (2013.01); *C12N 2510/00* (2013.01); *C12N 2710/14022* (2013.01); *C12N 2710/14023* (2013.01); *C12N 2710/14034* (2013.01); *C12N 2710/14041* (2013.01); *C12N 2710/14122* (2013.01); *C12N 2710/14131* (2013.01); *C12N 2710/14143* (2013.01); *C12N 2710/20022* (2013.01); *C12N 2710/20034* (2013.01); *C12N 2710/20051* (2013.01); *C12N 2750/10022* (2013.01); *C12N 2750/10034* (2013.01); *C12N 2750/10051* (2013.01); *C12N 2770/16022* (2013.01); *C12N 2770/16034* (2013.01); *C12N 2770/16051* (2013.01)

(58) Field of Classification Search
CPC ................ C12N 15/86; C12N 2502/00; C12N 2510/00; C12N 2710/14023; C12N 2710/14034; C12N 2710/14041; C07H 21/04
USPC ...... 435/69.1, 235.1, 320.1, 404; 424/93.21; 536/23.4, 23.7, 24.1
See application file for complete search history.

(56) References Cited

U.S. PATENT DOCUMENTS

| | | | |
|---|---|---|---|
| 5,965,393 A | 10/1999 | Hasnain et al. | |
| 2009/0068703 A1 | 3/2009 | Chao et al. | |

FOREIGN PATENT DOCUMENTS

| | | |
|---|---|---|
| EP | 1811027 A1 | 7/2007 |
| ES | 2232308 B1 | 5/2005 |
| KR | 20010074351 A | 8/2001 |
| WO | WO-2005/085456 A1 | 9/2005 |
| WO | WO-2010/025764 A1 | 3/2010 |
| WO | WO-2011/069562 A1 | 6/2011 |
| WO | WO-2012/168492 A2 | 12/2012 |
| WO | WO-2012/168789 A2 | 12/2012 |
| WO | WO-2012/169940 A2 | 12/2012 |

OTHER PUBLICATIONS

Gomez Sebastian et al., 2015, US 20150353898, effective filing date Jun. 12, 2012.*
Tomasinsig et al., 2005, Current Protein and Peptide Science, vol. 6, p. 23-34.*
Chattopadhyay et al., 2004, Virus Research, vol. 99, p. 139-145.*

(Continued)

*Primary Examiner* — Shin Lin Chen
(74) *Attorney, Agent, or Firm* — McCarter & English, LLP; Jill Ann Mello

(57) ABSTRACT

The present invention may be included in the field of biotechnology and it covers the improved production of recombinant proteins in insect cells or insect larvae as biofactories by a novel expression cassette. This expression cassette comprises nucleic acid sequences such as promoters, homologous regions (hr) as enhancers, and sequences encoding transcriptional regulators, for example, the baculovirus Ac-ie-01 cDNA, or any combination thereof, which are able to increase the quality and production efficiency of the recombinant proteins. Moreover, the present invention is also directed to the vectors themselves comprising the above mentioned nucleic acid sequences of the invention, cells or insects infected, transformed or transfected with those sequences or vectors, and methods for producing the recombinant proteins by using the aforesaid sequences, vectors, cells or insects.

12 Claims, 15 Drawing Sheets

(56) References Cited

OTHER PUBLICATIONS

Pandey, Prativa, 2007, Abstracts, 59th Southeast regional Meeting of the American Chemical Society, Greenville, SC, United States, GEN-671, Publisher: American Chemical Society, Washington D.C.*
Bryan et al., 2013, http://www.elsevierblogs.com/currentcomments/? p=962, Implications of protein fold switching, p. 1-4.*
Iatrou et al., 2003, US 20030027257 A1.*
Wu et al., 2009, US 20090162398 A1.*
Chao et al., Issued_Patents_NA, Sequence 2, U.S. Appl. No. 11/851,042 (now U.S. Pat. No. 8,105,827 B2), current filing date, Jan. 16, 2008, computer printout pp. 2-5.*
Morrison et al., 2007, N_Geneseq Accession No. AEX83551, computer printout pp. 71-73.*
Possee et al., 1994, GenEmbl Accession No. M75679, computer printout pp. 4-6.*
Alves, C.A., et al., "hycu-hr6, A large homologous region of the *Hypantria cunea* nucleopolyhedrovirus genome, as a powerful and versatile enhancer in insect expression systems", *Virus Genes*, Kluwer Academic Publishers, BO, vol. 39, No. 3, 2009, pp. 403-408.
Baek, J.O., et al., "Production and purification of human papillomavirus type 33 L1 virus-like particles from Spodoptera frugiperda 9 cells using two-step column chromatography", *Protein Expression and Purification*, vol. 75, No. 2, 2010, pp. 211-217.
Berger, I., et al., "Baculovirus expression system for heterologus multiprotein complexes", *Nature Biotechnology*, vol. 22, No. 12, 2004, pp. 1583-1587.
Bieniossek, C., et al., "MultiBac: expanding the research toolbox for multiprotein complexes", *Trends in Biochemical Sciences*, vol. 37, No. 2, 2012, pp. 49-57.
Crouch, E.A., et al., "Effects of baculovirus transactivators IE-1 and IE-2 on the *Drosophila* heat shock 70 promoter in two insect cell lines", *Archives of Virology; Official Journals of the Virology Division of the International Union of Microbiological Societies*, Springer-Verlag VI, vol. 150, No. 8, 2005, pp. 1563-1578.
Dai, X., "The acidic activation domains of the baculovirus transactivators IE1 and IE0 are functional for transcritional activation in both insect and mammalian cells", *Journal of General Virology*, vol. 85, No. 3, 2004, pp. 573-582.
Fan, H., et al., "Construction and immunogenicity of recombinant pseudotype baculovirus expressing the capsid protein of porcine circovirus type 2 in mice", *Journal of Virological Methods*, vol 150, No. 1-2, 2008, pp. 21-26.
Gomez-Casado, E., et al., "Insect larvae biofactories as a platform for influenza vaccine production", *Protein Expression and Purification*, vol. 79, 2011, pp. 35-43.
Gomi, S., et al., "Sequence analysis of the genome of Bombyx mori nucleopolyhedrovirus", *Journal of General Virology*, vol. 80, No. 5, 1999, 1323-1337.
Guo, M., et al., "Expression and Self-Assembly in Baculovirus of Porcine Enteric Calicivirus Capsids into Virus-Like Particles and Their Use in an Enzyme-Linked Immunosorbent Assay for Antibody Detection in Swine", *Journal of Clinical Microbiology*, vol. 39, No. 4, 2001, pp. 1487-1493.
Hashimoto, Y., et al., "Ao38, a new cell line from eggs of the black witch moth, *Ascalapha odorata* (Lepidoptera: Noctuidae), is permissive for AcMNPV infection and produces high levels of recombinant proteins", *BMC Biotechnology*, vol. 10, 2010, p. 50.
Hill-Perkins, M.S., et al., "A baculovirus expression vector derived from the basic protein promoter of *Autographa californica* nuclear polyhedrosis virus", *Journal of General Virology*, vol. 71, 1990, pp. 971-976.
Hitchman, R.B., et al., "Baculovirus expression systems for recombinant protein production in insect cells", *Recent Patents on Biotechnology*, vol. 3, No. 1, 2009, pp. 46-54.
International Search Report and Written Opinion of PCT/EP2012/061081, dated Feb. 19, 2013.

International Search Report and Written Opinion of PCT/EP2012/061088, dated Mar. 6, 2013.
International Search Report and Written Opinion of PCT/EP2013/075812, dated Apr. 25, 2014.
Kang, W., et al., "IE1 and hr facilitate the localization of *Bombyx mori* nucleopolyhedrovirus ORF8 to specific nuclear sites", *Journal of General Virology*, vol 86, No. 11, 2005, pp. 3031-3038.
Kanginakudru, S., et al., "Targeting ie-1 gene by RNAi induces baculoviral resistance in lepidopteran cell lines and in transgenic silkworms", *Insect Molecular Biology*, vol. 16, No. 5, 2007, pp. 635-644.
Kawasaki, Y., "Analysis of baculovirus IE1 in living cells: dynamic and spatial relationship in viral structural proteins", *Journal of General Virology*, vol. 85, No. 12, 2004, pp. 3575-3583.
Lin, X., et al., "Baculovirus immediately early 1, a mediator for homologous regions enhancer function *in trans*", *Virology Journal*, vol. 7, No. 32, 2010.
Lo, H.-R., et al., "Novel Baculovirus DNA Elements Strongly Stimulate Activities of Exogenous and Endogenous Promoters", *Journal of Biological Chemistry*, vol. 277, No. 7, 2002, pp. 5256-5264.
López-Vidal, J., et al., "Characterization of a Trichoplusia ni hexamerin-derived promoter in the AcMNPV baculovirus vector", *Journal of Biotechnology*, vol. 165, No. 3-4, 2013, pp. 201-208.
Majima, K., et al., "Divergence and evolution of homologous regions of Bombyx mori nuclear polyhedrosis virus", *Journal of Virology*, vol. 67, No. 12, 1993, pp. 7513-7521.
Nagai, S., et al., "Comparative transient expression assay analysis of hycu-hr6- and IE1-dependent regulation of baculovirus *gp64* early promoters in three insect lines", *Virus Research*, Amsterdam, NL, vol. 155, No. 1, 2011, pp. 83-90.
Nagamine, T., et al., "Focal Distribution of Baculovirus IE1 Triggered by its Binding to the hr DNA Elements", *Journal of Virology*, vol. 79, No. 1, 2005, pp. 39-46.
Nagamine, T., et al., "Induction of a sub-nuclear structure by the simultaneous expression of baculovirus proteins, IE1, LEF3, and P143 in the presence of hr", *Virology*, Academic Press, Orlando, US, vol. 352, No. 2, 2006, pp. 400-407.
Nettleship, J.E., et al., "Recent advances in the production of proteins in insect and mammalian cells for structural biology", *Journal of Structural Biology*, Academic Press, US, vol. 172, No. 1, 2010, pp. 55-65.
Ogawa, S., et al., "Generation of a transgenic silkworm that secretes recombinant proteins in the sericin layer of cocoon: Production of recombinant human serum albumin", *Journal of Biotechnology*, Elsevier Science Publishers, vol. 128, No. 3, 2007, pp. 531-544.
Okano, L., et al., "Colocalization of baculovirus IE-1 and two DNA-binding proteins, DBF and LEF-3, to viral replication factories", *Journal of Virology*, vol. 73, No. 1, 1999, pp. 110-119.
Olson, V.A., et al., "The highly conserved basic domain I of baculovirus IE1 is required for hr enhancer DNA binding and hr-dependent transactivation", *Journal of Virology, The American Society for Microbiology*, US, vol. 77, No. 10, 2003, pp. 5668-5677.
Passarelli, A.L., et al., "Three baculovirus genes involved in late and very late gene expression: ie-1, ie-n, and lef-2", *Journal of Virology*, vol. 67, No. 4, 1993, pp. 2149-2158.
Perez-Filgueira, D.M., et al., "Development of a low-cost, insect larvae-derived recombinant subunit vaccine against RHDV", *Virology*, vol. 364, No. 2, 2007, pp. 422-430.
Radner, S., et al., "Transient transfection couples to baculovirus infection for rapid protein expression screening in insect cells", *Journal of Structural Biology*, vol. 179, No. 1, 2012, pp. 46-55.
Rodems, S. M., et al., "DNA-dependent transregulation by IE1 of *Autographa californica* nuclear polyhedrosis virus: IE1 domains required for transactivation and DNA binding", *Journal of Virology*, vol. 71, 1997, pp. 9270-9277.
Senger, T., et al., "Enhanced papillomavirus-like particle production in insect cells", *Virology*, vol. 388, No. 2, 2009, pp. 344-353.
Smith, G.E., et al., "Production of human beta interferon in insect cells infected with a baculovirus expression vector", *Molecular Cellular Biology*, vol. 3, 1983, pp. 2156-2165.

(56) References Cited

OTHER PUBLICATIONS

Taticek, R.A., el al., "Comparison of growth and recombinant protein expression in two different insect cells lines in attached and suspension culture", *Biotechnology Progress*, vol. 17, No. 4, 2001, pp. 676-684.

Tomita, M., et al., "A germline transgenic silkworm that secretes recombinant proteins in the sericin layer of cocoon", *Transgenic Research*, Kluwer Academic Publishers-Plenum Publishers, vol. 16, No. 4, 2007, pp. 449-465.

Valdes, V.J., et al., "Using double-stranded RNA to prevent in vitro and in vivo viral infections by recombinant baculovirus", *Journal of Biological Chemistry*, vol. 278, No. 21, 2003, pp. 19317-19324.

Venkaiah, B., et al., "An additional copy of the homologous region (hrl) sequence in the *Autographa californica* multinucleocapsid polyhedrosis virus genome promote hyperexpression of foreign genes,"*Biochemistry*, vol. 43, No. 25, 2004, pp. 8143-8151.

Gomez-Sebastien, S. et al., "Significant Productivity Improvement of the Baculovirus Expression Vector System by Engineering a Novel Expression Cassette", *PLOS One*, vol. 9, No. 5, e96562, May 2014, 10 pages.

Guarino, L.A., et al., "Interspersed Homologous DNA of *Autographa californica* Nuclear Polyhedrosis Virus Enhances Delayed-Early Gene Expression", *Journal of Virology*, vol. 60, No. 1, pp. 215-223, 1986.

Kimchi-Sarfaty, C., et al., "A 'Silent' Polymorphism in the MDR1 Gene Changes Substrate Specificity", *Science*, vol. 315, pp. 525-528, 2007.

Knebel, D., et al., "The promoter of the late p10 gene in the insect nuclear polyhedrosis virus *Autographa californica*: activation by viral gene products and sensitivity to DNA methylation", *The EMBO Journal*, vol. 4, No. 5, 1985, pp. 1301-1306.

Lopez-Vidal, J., et al., "Insect-derived promoters for baculovirus vectors improvement", *FEBS Journal*, vol. 276, (Suppl. 1), p. 438, Abstract P33.15, 2011.

Ngo, J.T. et al., "Computational Complexity, Protein Structure Prediction, and the Levinthal Paradox", In The Protein Folding Problem and Tertiary Structure Prediction, Merz et al. (eds.), Birkhauser Boston: Boston, MA, pp. 433 and 492-495, 1994.

Prikhod'ko, E., et al., "Induction of Apoptosis by Baculovirus Transactivator IE1", *Journal of Virology*, vol. 70, No. 10, 1996, pp. 7116-7124.

Rudinger, J., "Characteristics of the amino acids as components of a peptide hormone sequence", In Peptide Hormones, Parsons (ed.), 1976, University Park Press: Baltimore, MD, pp. 1-7.

Voet, D., et al., Biochemistry, 3rd Edition, John Wiley and Sons, 1990, pp. 126-128.

Weyer, U., et al., "A baculovirus dual expression vector derived from the *Autographa californica* nuclear polyhedrosis virus polyhedrin and p10 promoters: co-expression of two influenza virus genes in insect cells", *Journal of General Virology*,vol. 72, pp. 2967-2974, 1991.

\* cited by examiner

US 9,879,280 B2

BACULOVIRUS SYSTEM FOR EXPRESSING PROTEINS FORMING VIRUS-LIKE PARTICLES

RELATED APPLICATIONS

This application is a 35 U.S.C. §371 national stage filing of International Application No. PCT/EP2013/075812, filed Dec. 6, 2013, which claims priority to European Patent Application No. 12196120.5, filed Dec. 7, 2012. The entire contents of each of the foregoing applications are incorporated herein by reference.

FIELD OF THE INVENTION

The present invention may be included in the field of biotechnology and it covers the improved production of recombinant proteins in insect cells or insect larvae as biofactories by a novel expression cassette. This expression cassette comprises nucleic acid sequences such as promoters, homologous regions (hr) as enhancers, and sequences encoding transcriptional regulators, for example, the baculovirus Ac-ie-01 cDNA, or any combination thereof, which are able to increase the quality and production efficiency of the recombinant proteins, in particular those forming virus-like particles. Moreover, the present invention is also directed to the vectors themselves comprising the above mentioned nucleic acid sequences of the invention, cells or insects infected, transformed or transfected with those sequences or vectors, and methods for producing the recombinant proteins by using the aforesaid sequences, vectors, cells or insects.

STATE OF THE ART

The baculovirus expression vector system (BEVS) is a well-established method for the production of recombinant proteins to be used as vaccines, therapeutic molecules or diagnostic reagents. With its potential for over-expression and rapid speed of development, BEVS is one of the most attractive choices for producing recombinant proteins for any purpose. The most employed baculovirus used in industry for recombinant protein expression is based on *Autographa californica* multiple nucleopolyhedrovirus (AcMNPV) with *Spodoptera frugiperda* 9 (Sf9) or 21 (Sf21) insect cells as suitable expression hosts (1), as well as *Trichoplusia ni* (*T. ni*) insect larvae as living biofactories (2). Since the BEVS was developed in the 80's (3), hundreds of recombinant proteins, ranging from cytosolic enzymes to membrane-bound proteins, have been successfully produced in baculovirus-infected insect cells.

Efforts have been made to increase BEVS productivity (4). A variety of transfer vectors are available for the construction of recombinant baculoviruses, encoding resident fusion proteins, which have been reported to improve protein expression, including maltose binding protein, glutathione S transferase, SUMO and KDEL retention signal. Other attempts related to improve the stability of expressed proteins have been investigated focusing on two genes in the baculovirus genome, which are not essential for growth of the virus in cell culture, namely chiA (chitinase) and cath (cathepsin). ChiA deletion appears to improve the production of secreted proteins by accumulating the protein in the endoplasmic reticulum and processing the proteins through the secretory pathway of the cells. Additionally, the prevention of the formation of cathepsin protease may also contribute to improved product stability from chiA⁻ viruses.

Novel insect cell lines, such as High-Five™ (Hi-5) or BTI-TnAo38 cell lines from *T. ni*, have recently been developed to increase the baculovirus productivity with significant improvements in the final amount of heterologous protein recovery (5, 6).

Accelerating recombinant protein expression, so that protein expression takes place before the machinery of insect cells is severely impaired by the baculovirus infection, would be an important improvement of the BEVS. Late expression, driven by the conventional strong virus promoters of polyhedrin (polh) or p10 genes, has serious disadvantages in the foreign protein post-translational modifications. Baculovirus promoters that allow for earlier expression than the conventionally used polh or p10 promoters have been characterized and been used for heterologous protein production, but showed a reduced productivity (7).

Another possibility for improving the BEVS would be to increase preservation of cell integrity at late times post-infection by reducing the virus-induced cell death. Reduction in the severe impairment of the insect cell machinery at late times post-infection caused by BEVS should not only increase the time frame for producing and accumulating recombinant proteins (secreted or not), but also allow more time for the folding of complex proteins or any post-translational modification of the produced proteins.

Some baculovirus DNA elements have been determined to be involved in the activation of late expression factor genes, which are necessary for virus propagation. One of them is the immediate early (ie) protein IE-1 and its splice variant IE-0 from AcMNPV (8). Translation of the AcMNPV mRNAs, encoded by the Ac-ie-01 gene, results in both IE-0 and IE-1 expression due to internal translation initiation. Both are thought to be critical mediators of baculovirus gene expression due to their potency as transcriptional regulators (9). Synthesized very early during infection, AcMNPV IE-1 is a 67-kDa dimeric DNA-binding protein that stimulates transcription in plasmid transfection assays through the activity of its N-terminal acidic domain (10, 11). IE-1 accumulates within the nucleus, where it is maintained through late times (12). Transactivation by IE-1 is enhanced by its binding as a homodimer to the baculovirus homologous region (hr) sequences, which function as transcriptional enhancers and origins of viral DNA replication. AcMNPV IE-0 is a 72.6-kDa 636 amino acid protein composed of 38 amino acids encoded by orf141 (exon0), 16 amino acids encoded by the upstream nontranslated leader of ie1, and the entire 582 amino acid IE-1 protein. The final product is therefore identical to IE-1 except for the additional 54 amino acids fused to the N-terminus. Presumably due to their common sequences, IE-0 and IE-1 share biochemical activities, including hr enhancer binding and transcriptional regulation.

SUMMARY OF THE INVENTION

The present invention is based to a large extent on the unexpected properties of the expression cassette of the invention.

In particular, it was discovered that the expression cassette of the invention drives the expression of recombinant proteins markedly higher than the expression obtained by conventional promoters, such as polh, and thus to unprecedented levels.

Furthermore, cells and insects infected with a recombinant baculovirus containing an expression cassette that expresses the IE-1/IE-0 proteins above endogenous levels have an increased viability and an increase in the integrity of the molecular cell machinery and cell morphology.

The present invention thus provides products and methods for the improved expression of recombinant proteins and, in particular, those forming virus-like particles.

The following items are preferred embodiments for allowing this improved expression:

1. An expression cassette comprising nucleic acid sequences that allow for the expression of the transcriptional regulators IE-1 and/or IE-0 above the endogenous levels obtained during baculovirus infection and the expression of a recombinant protein,
   wherein the expression of the recombinant protein is driven by a promoter comprising the baculoviral p10 promoter and
   wherein the recombinant protein is selected from the group consisting of a virus like particle protein, vaccine protein, subunit monomeric vaccine protein, subunit multimeric vaccine protein, therapeutic protein, antibody, enzyme, cytokine, blood clotting factor, anticoagulant, receptor, hormone and diagnostic protein.

2. An expression cassette comprising nucleic acid sequences that allow for the expression of the transcriptional regulators IE-1 and/or IE-0 above the endogenous levels obtained during baculovirus infection and the expression of a recombinant protein,
   wherein the recombinant protein is selected from the group consisting of virus-like particle protein, vaccine protein, subunit monomeric vaccine protein, subunit multimeric vaccine protein, therapeutic protein, antibody, enzyme, cytokine, blood clotting factor, anticoagulant, receptor, hormone and diagnostic protein.

3. The expression cassette according to item 1 or 2, wherein the recombinant protein is any virus-like particle protein selected from the group consisting of:
   (a) Porcine circovirus capsid protein,
   (b) Foot and mouth disease virus VP1, VP3 or VP0 protein,
   (c) Canine parvovirus VP1 and VP2 proteins,
   (d) Porcine parvovirus VP1 and VP2 proteins,
   (e) Human norovirus (genogroup I or II) capsid protein,
   (f) Calicivirus capsid protein,
   (g) Human papillomavirus L1 protein,
   (h) Hepatitis E protein E2,
   (i) Infectious bursal disease virus VP1, VP2 and VP3 proteins,
   (j) Astrovirus ORF2-encoded proteins,
   (k) Influenza virus HA, NA and M1 proteins,
   (l) Hepatitis B core and surface antigens,
   (m) Parvovirus VP1 and VP2 proteins, and
   (n) Rabbit calicivirus VP60 protein.

4. The expression cassette according to item 3, wherein the porcine circovirus capsid protein is the capsid protein from porcine circovirus type 2, the human papillomavirus L1 protein is the L1 protein from human papillomavirus 16 and the rabbit calicivirus VP60 protein is the VP60 protein from rabbit haemorrhagic disease virus.

5. The expression cassette according to item 1 or 2, wherein the recombinant protein is any virus-like particle protein, vaccine protein or diagnostic protein selected from the group consisting of:
   (a) Porcine circovirus capsid protein,
   (b) Foot and mouth disease virus VP1, VP3 or VP0 protein,
   (c) Canine parvovirus VP1 and VP2 proteins,
   (d) Porcine parvovirus VP1 and VP2 proteins,
   (e) Human parvovirus VP1 and VP2 proteins
   (f) Human norovirus (genogroup I or II) capsid protein,
   (g) Calicivirus capsid protein,
   (h) Human papillomavirus L1 protein,
   (i) Hepatitis E protein E2,
   (j) Classical swine fever E2 protein,
   (k) Bovine viral diarrhoea virus (BVDV) E2 protein,
   (l) Influenza A virus HA, NA and M1 proteins,
   (m) Infectious bursal disease virus VP1, VP2 and VP3 proteins,
   (n) Astrovirus ORF2-encoded proteins,
   (o) Hepatitis B core and surface antigens,
   (p) West Nile virus E protein,
   (q) African swine fever virus p30, p54, p72 and CD2-like proteins,
   (r) Single domain antibody (VHH) from camelids,
   (s) Parvovirus VP1 and VP2 proteins,
   (t) Rabbit calicivirus VP60 protein, and
   (u) Full-length mammalian antibodies or derived fragments thereof.

6. The expression cassette according to any of the items 1-5, comprising a nucleic acid sequence encoding the IE-1 and/or IE-0 proteins selected from the group consisting of:
   (a) nucleic acid sequence indicated in any of SEQ ID NO: 1-5;
   (b) nucleic acid sequence having a sequence identity of at least 70%, preferably at least 80%, more preferably at least 90% and most preferably at least 95% with the nucleic acid sequence indicated in any of SEQ ID NO: 1-5 and encoding a protein functioning as a transcriptional regulator in a baculovirus;
   (c) nucleic acid sequence encoding a protein with the amino acid sequence indicated in any of SEQ ID NO: 6-9; and
   (d) nucleic acid sequence encoding a protein functioning as a transcriptional regulator in a baculovirus and having a sequence similarity of at least 70%, preferably at least 80%, more preferably at least 90% and most preferably at least 95% with the amino acid sequence indicated in any of SEQ ID NO: 6-9.

7. The expression cassette according to any of the items 1-6, wherein the promoter driving the expression of the recombinant protein comprises a nucleic acid sequence selected from the group consisting of:
   (a) nucleic acid sequence indicated in any of SEQ ID NO: 10-16; and
   (b) nucleic acid sequence functioning as a promoter in a baculovirus and having a sequence identity of at least 70%, preferably at least 80%, more preferably at least 90% and most preferably at least 95% with the nucleic acid sequence indicated in any of SEQ ID NO: 10-16.

8. The expression cassette according to item 7, wherein the promoter driving the expression of the recombinant protein comprises a nucleic acid sequence selected from the group consisting of:
   (a) nucleic acid sequence indicated in any of SEQ ID NO: 11, 12, 13, 15 and 16; and
   (b) nucleic acid sequence functioning as a promoter in a baculovirus and having a sequence identity of at least 70%, preferably at least 80%, more preferably at least 90% and most preferably at least 95% with the nucleic acid sequence indicated in any of SEQ ID NO: 11, 12, 13, 15 and 16.

9. The expression cassette according to item 7 or 8, wherein the promoter driving the expression of the recombinant protein comprises a nucleic acid sequence selected from the group consisting of:
   (a) nucleic acid sequence indicated in SEQ ID NO: 11; and
   (b) nucleic acid sequence functioning as a promoter in a baculovirus and having a sequence identity of at least 70%, preferably at least 80%, more preferably at least 90% and most preferably at least 95% with the nucleic acid sequence indicated in SEQ ID NO: 11.
10. The expression cassette according to any of the items 1-9, comprising at least one recombinant homologous region (hr) as enhancer region, operably linked to the promoter that drives the expression of the recombinant protein.
11. The expression cassette according to item 10, wherein the recombinant homologous region (hr) is selected from the group of nucleic acid sequences consisting of:
    (a) nucleic acid sequence indicated in SEQ ID NO: 27; and
    (b) nucleic acid sequence functioning as an enhancer homologous region in a baculovirus and having a sequence identity of at least 70%, preferably at least 80%, more preferably at least 90% and most preferably at least 95% with the nucleic acid sequence indicated in SEQ ID NO: 27.
12. The expression cassette according to any of the items 1-11, comprising a nucleic acid sequence that is operably linked to the expression of the recombinant protein and selected from the group consisting of:
    (a) nucleic acid sequence containing the nucleic acid sequence indicated in any of SEQ ID NO: 17-22, 25 and 26 and
    (b) nucleic acid sequence substantially retaining the activity of the functional elements and having a sequence identity of at least 70%, preferably at least 80%, more preferably at least 90% and most preferably at least 95% with the nucleic acid sequence indicated in any of SEQ ID NO: 17-22, 25 and 26.
13. The expression cassette according to item 12, comprising a nucleic acid sequence that is operably linked to the expression of the recombinant protein and selected from the group consisting of:
    (a) nucleic acid sequence containing the nucleic acid sequence indicated in any of SEQ ID NO: 17-19 and 25; and
    (b) nucleic acid sequence substantially retaining the activity of the functional elements and having a sequence identity of at least 70%, preferably at least 80%, more preferably at least 90% and most preferably at least 95% with the nucleic acid sequence indicated in any of SEQ ID NO: 17-19 and 25.
14. The expression cassette according to any one of items 1-11, comprising a nucleic acid sequence selected from the group consisting of:
    (a) nucleic acid sequence containing the nucleic acid sequence indicated in any of SEQ ID NO: 51-56; and
    (b) nucleic acid sequence substantially retaining the activity of the functional elements and having a sequence identity of at least 70%, preferably at least 80%, more preferably at least 90% and most preferably at least 95% with the nucleic acid sequence indicated in any of SEQ ID NO: 51-56.
15. A cloning vector comprising the expression cassette of any of the items 1-14.
16. A transfer vector comprising the expression cassette of any of the items 1-14 and further a nucleic acid sequence suitable for integration or transposition in a baculovirus genome.
17. The transfer vector according to item 16, characterized in that the transfer vector is derived from any of the baculovirus expression systems "Bac-to-Bac®" (Invitrogen™), "BacPAK™" (Clontech™), "FlashBAC™" (Oxford Expression Technologies™), "BacuVance™" (GenScript™), "Bac-N-Blue DNA™" (Invitrogen™), "BaculoDirect™" (Invitrogen™), "BacVector®" 1000, 2000, 3000 (Novagen®), "DiamondBac™" (Sigma-Aldrich®) or "BaculoGold™" (BD Biosciences™).
18. A bacmid comprising the expression cassette of any of the items 1-14.
19. A recombinant baculovirus comprising the expression cassette of any of the items 1-14.
20. A cell comprising the expression cassette of any of the items 1-14.
21. The cell according to item 20, infected, transfected, transduced or transformed with the expression cassette, cloning vector, transfer vector, bacmid or recombinant baculovirus of any of the items 1-19.
22. The cell according to item 20 or 21, characterized in that it is of insect origin.
23. The cell according to any of the items 20-22, characterized in that it is derived from an insect belonging to the *Lepidoptera* or *Diptera* genus.
24. The cell according to any of the items 20-23, characterized in that it is derived from *Trichoplusia ni, Spodoptera frugiperda, Ascalapha odorata, Bombyx mori, Drosophila melanogaster, Stigmene acrea* or *Aedes aegypti*.
25. The cell according to any of the items 20-24, characterized in that it is a cell line selected from the group consisting of Hi-5™, Sf9, Sf21, BTI-Tn5B-1, Tn368, ExpresSf+®, BTI-TnAo38, ATC-10, Mimic™ Sf9, SfSWT-1, SfSWT-3, SfSWT-5, TriEX™ and Schneider's *Drosophila* Line 2.
26. An insect comprising the expression cassette of any of the items 1-14.
27. The insect according to item 26, infected, transfected, transduced or transformed with the expression cassette, cloning vector, transfer vector, bacmid or recombinant baculovirus of any of the items 1-19.
28. The insect according to item 26 or 27, wherein the insect is derived from the genus *Lepidoptera*.
29. The insect according to any of the items 26-28, wherein the insect is selected from the group consisting of *Trichoplusia ni, Spodoptera frugiperda, Spodoptera exigua, Ascalapha odorata, Bombyx mori, Rachiplusia ni* and *Stigmene acrea*.
30. The insect according to any of the items 26-29, wherein the expression cassette is introduced into the insect by a recombinant baculovirus, preferably AcMNPV, SeNPV or BmNPV.
31. A culture medium comprising the expression cassette, cloning vector, transfer vector, bacmid or recombinant baculovirus of any of the items 1-19.
32. A method for producing a recombinant protein comprising the use of the expression cassette, cloning vector, transfer vector, bacmid, recombinant baculovirus, cell or insect according to any of the items 1-30 and the extraction and purification of the recombinant protein by conventional means.

33. Recombinant protein obtainable by the method according to item 32.
34. Recombinant protein according to item 33 for use in a method of treatment, therapy or diagnostic.
35. Method of treatment, therapy or diagnostic using the recombinant protein according to item 33.
36. A use of the expression cassette according to any of the items 1-14 for producing a cloning vector, transfer vector, bacmid, recombinant baculovirus, cell, insect or culture medium according to any of the items 15-31.
37. A use of the cloning vector according to item 15 for producing a transfer vector, bacmid, recombinant baculovirus, cell, insect or culture medium according to any of the items 16-31.
38. A use of the transfer vector according to any of the items 16-17 for producing a bacmid, recombinant baculovirus, cell, insect or culture medium according to any of the items 18-31.
39. A use of the bacmid according to item 18 for producing a recombinant baculovirus, cell, insect or culture medium according to any of the items 19-31.
40. A use of the recombinant baculovirus according to item 19 for producing a cell, insect or culture medium according to any of the items 20-31.

Figure 1:
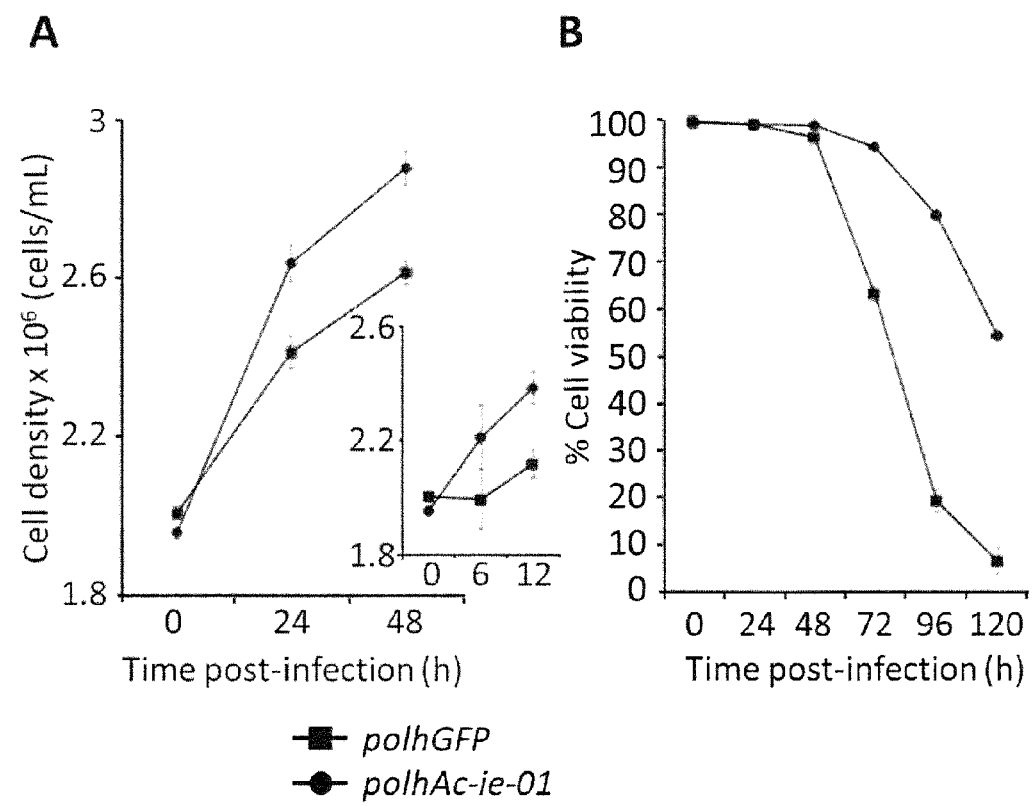
FIG. 1. Sf9 insect cells were cultured in suspension and infected by a baculovirus overexpressing the Ac-ie-01 cDNA under the control of polh. or by a conventional baculovirus expressing the GFP protein under the control of polh promoter to assess the cell density (A) and viability (B) of these cells. The insect cells were infected in suspension at a MOI of 0.1. (A) The cells were counted at different times post-infection (0, 24 and 48 hours) to calculate the cell density. A more detailed analysis of the precise moment in which cell proliferation is produced by the overexpression of the Ac-ie-01 cDNA is shown in the insert for cells infected with polhGFP or polhAc-ie-01. (B) Cell viability was assessed by Trypan blue staining (dilution 1:1 of suspended cells and colorant at 0.4% in PBS buffer). This staining allows the differentiation between live and death cells. Cell viability was calculated by the percentage of living cells with respect to the total number of cells at different times post-infection (from 0 to 120 hours). Micrographs of Hi-5™ insect cell monolayers infected at a MOI of 5 with a control conventional baculovirus overexpressing the reporter protein GFP under the polh promoter (C) or with a baculovirus overexpressing the Ac-ie-01 cDNA under the control of the polh promoter (D). Micrographs were obtained at 96 h post-infection at a 20× magnification in an inverted microscope Leica™ DMIL™.
Figure 1:
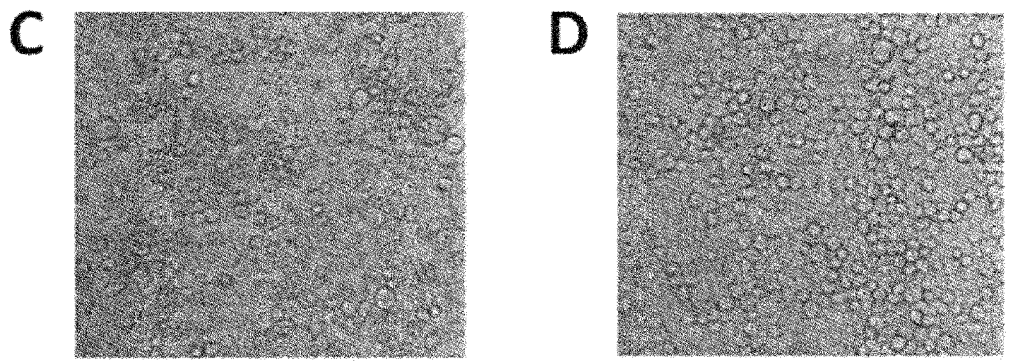

FMDV serotype C complete genome: GenBank AY593810.1

FMDV serotype SAT 1 complete genome: GenBank AY593846.1

FMDV serotype SAT 2 complete genome: GenBank JX014256.1

FMDV serotype ASIA 1 complete genome: GenBank HQ631363.1

Human parvovirus VP1 and VP2 protein, the sequence of which is indicated or can be derived, for example, from the following sequences:

Human parvovirus B19 isolate Vn115. GenBank: DQ357065.1

Human parvovirus 4 isolate VES065 CSF. GenBank: HQ593532.1

Porcine parvovirus VP1 and VP2 protein, the sequence of which is indicated or can be derived, for example, from the following sequences:

Porcine parvovirus strain 693a. GenBank: JN400519.1

Porcine parvovirus strain 8a. GenBank: JN400517.1

Canine parvovirus VP1 and VP2 protein, the sequence of which is indicated or can be derived, for example, from the following sequences:

Canine parvovirus type 1 proteins VP1 and VP2: GenBank AB518883.1

Canine parvovirus type 2a VP1 and VP2. GenBank: M24003.1

Canine parvovirus type 2b VP2: GenBank FJ005265.1

Canine parvovirus Type 2C VP2: GenBank FJ005248.1

Human norovirus (genogroup I or II) capsid protein, the sequence of which is indicated or can be derived, for example, from the following sequences:

Norwalk virus: GenBank M87661, NP056821

Southampton virus: GenBank L07418

Mexico virus: GenBank U22498

Seto virus: GenBank AB031013

Chiba virus: GenBank AB042808

Lordsdale virus: GenBank X86557

Snow Mountain virus: GenBank U70059

Hawaii virus: GenBank U07611

Rabbit haemorrhagic disease virus VP60 protein, the sequence of which is indicated or can be derived, for example, from the following sequence:

NCBI Reference Sequence: NC_001543.1

Human papillomavirus L1 protein, the sequence of which is indicated or can be derived, for example, from the following sequences:

HPV 6: GenBank: JN252323.1

HPV 11: GenBank: JQ773411.1

HPV 16: GenBank DQ155283.1

HPV 18: GenBank FJ528600.1

Hepatitis E virus E2 protein, the sequence of which is indicated or can be derived, for example, from the following sequences:

Hepatitis E virus, complete genome NCBI Reference Sequence: NC_001434.1

Swine hepatitis E virus isolate ITFAE11 capsid protein gene. GenBank: JN861806.1

Preferably, the recombinant protein is selected from the above group of virus-like particle proteins except for the capsid protein from porcine circovirus.

In an alternative preferred embodiment, the recombinant protein is the virus-like particle protein selected from the group consisting of the capsid protein from a porcine circovirus, the L1 protein from human papillomavirus and the VP60 protein from rabbit calicivirus. Preferably, the capsid protein is from porcine circovirus type 2, the L1 protein is from human papillomavirus 16 and the VP60 protein is from rabbit haemorrhagic disease virus.

In another preferred embodiment, the recombinant protein is a vaccine protein and/or diagnostic protein selected from the following group of proteins:

Classical swine fever virus E2 protein, the sequence of which is indicated or can be derived, for example, from the following sequences:

complete genome strain HNLY-2011: GenBank JX262391.1 complete genome strain Alfort/187: GenBank X87939.1 complete genome strain BRESCIA: GenBank AF091661.1

Bovine viral diarrhoea virus (BVDV) E2 protein, the sequence of which is indicated or can be derived, for example, from the following sequences:

BVDV type 1 polyprotein strain Osloss: GenBank M96687.1

BVDV type 1 polyprotein strain KS86-1cp: GenBank AB078952.1

BVDV type 1 polyprotein strain KS86-1ncp: GenBank AB078950.1

Influenza A virus HA protein, the sequence of which is indicated or can be derived, for example, from the following sequences:

H4 influenza A virus (A/shorebird/Delaware Bay/589/2008(H4N6)) hemagglutinin (HA) gene: GenBank: CY126622.1

H1 Influenza A virus (A/England/93760756/2009 (H1N1) hemagglutinin (HA) gene: GenBank: JX625498.1

H3 Influenza A virus (A/mallard-black duck hybrid/New Brunswick/02657/2007(H3N8)) hemagglutinin (HA) gene: GenBank: CY129382.1

H7 Influenza A virus (A/American black duck/New Brunswick/02493/2007(H7N3)) hemagglutinin (HA) gene: GenBank: CY128714.1

H5 Influenza A virus (A/chicken/Giza/CAI26/2011 (H5)) hemagglutinin (HA) gene: GenBank: CY126001.1

West Nile virus E protein, the sequence of which is indicated or can be derived, for example, from the following sequence:

West Nile virus, complete genome NCBI Reference Sequence: NC_001563.2

African swine fever virus p30, p54, p72 and CD2-like protein, the sequence of which is indicated or can be derived, for example, from the following sequences:

Protein p30: GenBank: M88336.1

Protein p54: GenBank: JQ771683.1

Protein p72: GenBank: AY578708.1

Protein CD2-like (8DR): GenBank: AF050111.1

Single domain antibody (VHH) from camelids, such as 3B2 and 2KD1, which are specific for the VP6 protein from rotavirus A VHH 3B2 is, for example, represented by the amino acid sequence of SEQ ID NO: 44 or encoded by the nucleic acid sequence of SEQ ID NO: 43

VHH 2KD1 is, for example, represented by the amino acid sequence of SEQ ID NO: 46 or encoded by the nucleic acid sequence of SEQ ID NO: 45

Full-length mammalian antibodies or derived fragments thereof

The recombinant proteins are preferably encoded by the above indicated nucleic acid sequences (or the respective ORF in case of the genomic sequence) or represented by the respective amino acid sequences. The recombinant proteins may also be encoded or represented by variants of said sequences, for instance, representing different virus types and subtypes.

The sequence of the nucleic acid sequence variants is preferably at least 70%, more preferably at least 80%, more preferably at least 90% and most preferably at least 95% identical to the respective nucleic acid sequences (or the respective ORF in case of the genomic sequence).

The sequence of the amino acid sequence variants is preferably at least 70%, more preferably at least 80%, more preferably at least 90% and most preferably at least 95% similar to the respective amino acid sequences.

"Promoter" refers to a DNA sequence to which RNA polymerase can bind to initiate transcription. The sequence may further contain binding sites for various proteins that regulate transcription, such as transcription factors. The promoter sequence may be composed of different promoter fragments (either different or the same fragments) that are localized closely in the DNA sequence and may be separated by linkers or spacers. Such promoters are referred to as chimeric promoters.

The expression of the recombinant protein of the invention is preferably driven by a promoter selected from the group consisting of SEQ ID NO: 10-16 and variants thereof that are still functioning as a promoter in a baculovirus and have preferably at least 70%, more preferably at least 80%, more preferably at least 90% and most preferably at least 95% identity with the nucleic acid sequence indicated in any of SEQ ID NO: 10-16.

In another preferred embodiment, the expression of the recombinant protein of the invention is driven by a promoter selected from the group consisting of SEQ ID NO: 12-16 and variants thereof that are still functioning as a promoter in a baculovirus and have preferably at least 70%, more preferably at least 80%, more preferably at least 90% and most preferably at least 95% identity with the nucleic acid sequence indicated in any of SEQ ID NO: 12-16.

Most preferably, the expression of the recombinant protein of the invention is driven by a promoter that comprises SEQ ID NO: 11, i.e. the p10 promoter, or variants thereof that are still functioning as a promoter in a baculovirus and have preferably at least 70%, more preferably at least 80%, more preferably at least 90% and most preferably at least 95% identity with the nucleic acid sequence indicated in SEQ ID NO: 11. The promoter comprising SEQ ID NO: 11 may also comprise further promoter fragments and thus form a chimeric promoter.

The promoter comprising SEQ ID NO: 11 is preferentially selected from the group consisting of SEQ ID NO: 11, 12, 13, 15 and 16 and variants thereof that are still functioning as a promoter in a baculovirus and have preferably at least 70%, more preferably at least 80%, more preferably at least 90% and most preferably at least 95% identity with the nucleic acid sequence indicated in any of SEQ ID NO: 11, 12, 13, 15 and 16.

In a preferred embodiment, the polyadenylation signal from the nucleic acid encoding the recombinant protein is the p10 or SV40 polyadenylation signal. Most preferably, it is the p10 polyadenylation signal. The most preferred expression cassettes comprising the polyadenylation signal from the nucleic acid encoding the recombinant protein are represented by SEQ ID NO: 51-56 (or variants of these sequences retaining the activity of the functional elements and having a sequence identity of at least 70%, preferably at least 80%, more preferably at least 90% and most preferably at least 95% with the nucleic acid sequence indicated in any of SEQ ID NO: 51-56).

As described above, a further recombinant DNA element that is present in the expression cassette of the invention is a nucleic acid sequence that allows for the expression above endogenous levels of baculovirus transcriptional regulators. Preferably this nucleic acid sequence is operably linked to the expression of the recombinant protein.

"Transcriptional regulator" refers to a regulatory protein that has the ability to modulate the transcription of specific genes by, for example, binding to enhancer or repressor regions and/or recruiting further proteins that are involved in transcription.

"Endogenous expression level" refers to the ground level of expression of a protein that is obtained during the infection of an insect cell or insect with a baculovirus that has not been altered in its expression of said protein by, for example, artificial means, such as introduction of a recombinant DNA sequence.

The "expression above endogenous levels" is also referred to as "overexpression".

Expression above endogenous levels can be achieved through, for example, introducing further copies of the endogenous gene encoding the transcriptional regulator or manipulating the expression of the promoter of the endogenous gene. Further, copies of the endogenous genes can be introduced as transgenes under the control of a suitable promoter such as polh or pB2$_9$.

The expression level can be determined at both the mRNA and the protein level with methods conventionally known to the person skilled in the art, such as quantitative PCR and Western Blot analysis.

"Being operably linked" refers to two nucleic acid sequences that are connected in a way that one influences the other in terms of, for example, transcriptional regulation.

IE-1 and its splice variant IE-0 are transcriptional regulators that are endogenously expressed by baculoviruses.

In a preferred embodiment, the baculovirus transcriptional regulators of the invention are IE-1 and/or IE-0.

In another preferred embodiment, the expression level of IE-1 and/or IE-0 reaches expression levels above those obtained by wild-type AcMNPV, such as the AcMNPV clone C6 (genomic sequence: GenBank accession no. NC_001623.1). In another preferred embodiment, the expression level of IE-1 and/or IE-0 reaches more than twofold the amount that can be obtained with wild-type AcMNPV, such as the AcMNPV clone C6.

IE-1 and/or IE-0 are preferably encoded by any of the nucleic acid sequences of SEQ ID NO: 1-5 or represented by any of the corresponding amino acid sequences of SEQ ID NO: 6-9. IE-1 and/or IE-0 may also be encoded or represented by any of the variants of said sequences.

SEQ ID NO: 1 is the Ac-ie-01 cDNA that encodes both IE-1 and IE-0, SEQ ID NO: 2 is the coding sequence (CDS) of IE-1 and SEQ ID NO: 3 is the CDS of IE-0. SEQ ID NO: 4 and 5 are the CDSs of the N-terminal domains of IE-1 and IE-0 respectively that substantially retain the transcriptional regulator activity. The proteins that are encoded by SEQ ID NO: 2-5 are represented by SEQ ID NO: 6-9 respectively.

The variants of SEQ ID NO: 1-9 are or encode amino acids that substantially retain their function as a transcriptional regulator.

The sequence of the variants of SEQ ID NO: 1-5 is preferably at least 70%, more preferably at least 80%, more preferably at least 90% and most preferably at least 95% identical to the sequences of SEQ ID NO: 1-5.

The sequence of the variants of SEQ ID NO: 6-9 is preferably at least 70%, more preferably at least 80%, more preferably at least 90% and most preferably at least 95% similar to the sequences of SEQ ID NO: 6-9.

In a preferred embodiment, the above sequences are limited to those encoding or representing the IE-1 protein, i.e. SEQ ID NO: 1, 2, 4, 6 and 8 or variants thereof as defined above.

In another preferred embodiment, the above sequences are limited to those encoding or representing the IE-0 protein, i.e. SEQ ID NO: 1, 3, 5, 7 and 9 or variants thereof as defined above.

In yet another preferred embodiment, IE-1 and/or IE-0 are encoded by the nucleic acid sequence of SEQ ID NO: 1.

In some embodiments, a recombinant homologous region (hr) that can enhance the expression of the recombinant protein by being operably linked to the promoter(s) of the same may further be present in the expression cassette of the invention, in addition to the nucleic acid sequences that allow for the expression of the recombinant protein and the expression above endogenous levels of the transcriptional regulators.

"Enhancer region" refers to a control sequence, whose binding by transcriptional regulators increases the level of transcription of associated genes.

Homologous regions, hr, are comprised of repeated units of about 70-bp with an imperfect 30-bp palindrome near their center. Homologous regions are repeated at eight locations in the AcMNPV genome with 2 to 8 repeats at each side. Homologous regions have been implicated as both transcriptional enhancers and origins of baculovirus DNA replication.

The enhancer homologous region sequence hr upstream of the promoter(s) is preferably hr1 (SEQ ID NO: 27) or a sequence that is able to function as an enhancer homologous region and has preferably at least 70%, more preferably at least 80%, more preferably at least 90% and most preferably at least 95% identity with the nucleic acid sequence indicated in SEQ ID NO: 27.

In a preferred embodiment, the expression cassette of the invention comprises combinations of recombinant promoters, sequences encoding transcriptional regulators and enhancer regions, which are operably linked to the expression of the recombinant protein, wherein these combinations are represented by any of SEQ ID NO: 17-22, 25 and 26 or variants thereof that substantially retain the activities of the functional elements and have preferably at least 70%, more preferably at least 80%, more preferably at least 90% and most preferably at least 95% identity with the nucleic acid sequences indicated in any of SEQ ID NO: 17-22, 25 and 26.

More preferably, the above mentioned combinations are represented by any of SEQ ID NO: 17-19 and 25 or variants thereof that substantially retain the activities of the functional elements and have preferably at least 70%, more preferably at least 80%, more preferably at least 90% and most preferably at least 95% identity with the nucleic acid sequences indicated in any of SEQ ID NO: 17-19 and 25.

The expression cassette of the invention can preferably be used to produce the cloning vector, transfer vector, bacmid, recombinant baculovirus, cell, insect or culture medium of the invention.

Cloning Vector

"Cloning vector" refers to any vector that is suitable for cloning, which generally involves the presence of restriction sites, an origin of replication for bacterial propagation and a selectable marker.

The cloning vector of the invention comprises the expression cassette of the invention and can preferably be used to produce the transfer vector, bacmid, recombinant baculovirus, cell, insect or culture medium of the invention.

The cloning vector comprising an expression cassette is also known as a "donor vector".

Transfer Vector

"Transfer vector" (or "baculovirus transfer vector") refers to a vector that is suitable for integration or transposition in a baculovirus genome. The transfer vector thus generally permits the insertion of genetic information into a baculovirus.

The transfer vector of the invention comprises the expression cassette of the invention and can preferably be used to produce the bacmid, recombinant baculovirus, cell, insect or culture medium of the invention.

In a further preferred embodiment, the transfer vector is derived from any of the commercially available baculovirus expression systems "Bac-to-Bac®" (Invitrogen™), "BacPAK™" (Clontech™), "FlashBAC™" (Oxford Expression Technologies™), "BacuVance™" (GenScript™), "Bac-N-Blue DNA™" (Invitrogen™), "BaculoDirect™" (Invitrogen™), "BacVector®" 1000, 2000, 3000 (Novagen®), "DiamondBac™" (Sigma-Aldrich®) or "BaculoGold™" (BD Biosciences™).

Bacmid

"Bacmid" refers to a plasmid construct which contains the nucleic acid sequence that is sufficient for generating a baculovirus when transfected into a cell.

The bacmid of the invention comprises the expression cassette of the invention and can preferably be used to produce the recombinant baculovirus, cell, insect or culture medium of the invention.

Baculovirus

"Baculovirus" refers to a family of infectious viruses for invertebrates, mainly infecting insects and arthropods. A "recombinant baculovirus" has further introduced recombinant DNA through, for example, homologous recombination or transposition.

The recombinant baculovirus of the invention comprises the expression cassette of the invention and can preferably be used to produce the cell, insect or culture medium of the invention.

The recombinant baculovirus preferably originates from AcMNPV.

In another preferred embodiment, the recombinant baculovirus originates from *Bombyx mori* nucleopolyhedrovirus (BmNPV) or *Spodoptera exigua* nucleopolihedrovirus (SeNPV).

Cell

The cell of the invention comprises the expression cassette of the invention. Inside this cell, the recombinant DNA elements of the expression cassette may be present on different molecules.

In a preferred embodiment, the cell is infected, transfected, transduced or transformed with the expression cassette, cloning vector, transfer vector, bacmid or recombinant baculovirus of the invention, most preferably with the recombinant baculovirus.

In a preferred embodiment, the cell is kept in cell culture.

The cell is preferably an insect cell line, more preferably a cell line derived from an insect belonging to the *Lepidop-* tera or Diptera genus, more preferably the cell is derived from the group consisting of *Trichoplusia ni, Spodoptera frugiperda, Ascalapha odorata, Bornbyx mori, Drosophila melanogaster, Stigmene acrea* and *Aedes aegypti* and most preferably it is selected from the group of insect cell lines consisting of Hi-5™, Sf9, Sf21, BTI-Tn5B-1, Tn368, ExpresSf+®, BTI-TnAo38, ATC-10, Mimic™ Sf9, SfSWT-1, SfSWT-3, SfSWT-5, TriEx™ and Schneider's *Drosophila* Line 2. The cell of the invention may be cultured in monolayer or in suspension.

Insect

The insect of the invention comprises the expression cassette of the invention. Inside this insect, the recombinant DNA elements of the expression cassette may be present on different molecules.

In a preferred embodiment the insect is infected, transfected, transduced or transformed with the expression cassette, cloning vector, transfer vector, bacmid or recombinant baculovirus of the invention.

The expression cassette of the invention is preferably introduced into the insect by a recombinant baculovirus. Preferably, this baculovirus is AcMNPV, SeNPV or BmNPV and the insect is an insect larva or insect pupa. The baculovirus is administered to the insect by oral administration (per os) or more preferably by injection.

In a further preferred embodiment, the insect is a transgenic insect.

The insect is preferably a lepidopter and more preferably an insect selected from the group consisting of *Trichoplusia ni, Spodoptera frugiperda, Spodoptera exigua, Ascalapha odorata, Bombyx mori, Rachiplusia ni* and *Stigmene acrea*. In a preferred embodiment, the insect is a larva or a pupa.

Preferably, the insect larvae are reared in a rearing module, such as the one described in the patent application ES 2 232 308.

Culture Medium

The culture medium of the invention comprises the expression cassette, cloning vector, transfer vector, bacmid or recombinant baculovirus of the invention.

In a preferred embodiment, the culture medium comprises the baculovirus of the invention.

Methods for Producing the Recombinant Protein

In a further aspect, the invention discloses methods for producing the recombinant protein of the invention.

In a preferred embodiment, the production of the recombinant protein comprises use of the expression cassette, cloning vector, transfer vector, bacmid, recombinant baculovirus, cell or insect of the invention. After expression of the recombinant protein, extraction and purification of said protein is made by conventional means.

Most preferably, said production method comprises use of the cell or insect of the invention.

In another preferred embodiment of the method for producing the recombinant protein, the cells of the invention are cultured in suspension (bioreactors), at densities between $2 \times 10^6$ to $8 \times 10^6$ cells per ml, depending on the cell line and the fermentation procedure used. Furthermore, cells are preferably infected at a MOI of 0.05 to 10.

In a preferred embodiment for the recombinant protein production, insect larvae or insect pupa are infected by injecting a high virus dose (higher than $10^4$ Plaque Forming Units) of the recombinant baculovirus of the invention. 3-4 days after infection, the infected insects are processed and the whole soluble protein extract is obtained by the use of appropriate extraction buffers. Extracts are centrifuged and the lipid fraction eliminated. Then, the recombinant protein is purified by conventional means.

In a preferred embodiment, the recombinant protein of the invention is used in a method of treatment, therapy or diagnostic. For example, the recombinant protein of the invention may be used for vaccination.

SUMMARY OF SEQUENCES

| SEQ ID NO: | Name: |
|---|---|
| 1 | Complete Ac-ie-01 cDNA |
| 2 | Coding DNA sequence (CDS) of IE-1 |
| 3 | CDS of IE-0 |
| 4 | CDS of the IE-1 N-terminal domain |
| 5 | CDS of the IE-0 N-terminal domain |
| 6 | IE-1 protein |
| 7 | IE-0 protein |
| 8 | IE-1 N-terminal domain protein |
| 9 | IE-0 N-terminal domain protein |
| 10 | polh (promoter) |
| 11 | p10 (promoter) |
| 12 | pB2$_9$p10 (promoter) |
| 13 | p6.9p10 (promoter) |
| 14 | pB2$_9$ (promoter) |
| 15 | pB2p10 (promoter) |
| 16 | polhp10 (promoter) |
| 17 | polhAc-ie-01/hr1p10 |
| 18 | polhAc-ie-01/hr1pB2$_9$p10 |
| 19 | polhAc-ie-01/hr1p6.9p10 |
| 20 | pB2$_9$Ac-ie-01/hr1p10 |
| 21 | pB2$_9$Ac-ie-01/hr1pB2$_9$p10 |
| 22 | pB2$_9$Ac-ie-01/hr1p6.9p10 |
| 23 | polhAc-ie-01/hr1polh |
| 24 | pB2$_9$Ac-ie-01/hr1polh |
| 25 | polhAc-ie-01/hr1polhp10 |
| 26 | pB2$_9$Ac-ie-01/hr1polhp10 |
| 27 | Homologous region enhancer hr1 |
| 28 | polhAc-ie-01 |
| 29 | polhGFP |
| 30 | polhAc-ie-01/hr1p6.9p10Cap |
| 31 | ORF2 from porcine circovirus type 2 |
| 32 | Capsid protein (Cap) from porcine circovirus type 2 |
| 33 | polhCap |
| 34 | polhAc-ie-01/hr1p6.9p10GFP |
| 35 | polhAc-ie-01/hr1polhp10GFP |
| 36 | polhAc-ie-01/hr1pB2$_9$p10GFP |
| 37 | polhAc-ie-01/hr1p6.9GFP |
| 38 | polhAc-ie-01/hr1p10GFP |
| 39 | polhAc-ie-01/hr1polhGFP |
| 40 | p6.9GFP |
| 41 | pB2$_9$GFP |
| 42 | p10GFP |
| 43 | Nucleic acid sequence encoding VHH 3B2 |
| 44 | Amino acid sequence of VHH 3B2 |
| 45 | Nucleic acid sequence encoding VHH 2KD1 |
| 46 | Amino acid sequence of VHH 2KD1 |
| 47 | Nucleic acid sequence encoding the L1 protein of the human papilloma virus 16 |
| 48 | Amino acidic sequence of the L1 protein of the human papilloma virus 16 |
| 49 | Nucleic acid sequence of the VP60 encoding gene from RHDV |
| 50 | Amino acidic sequence of the VP60 protein from RHDV |
| 51 | polhAc-ie-01/hr1p6.9p10Cap (polyadenylation signal from p10 gene) |
| 52 | polhAc-ie-01/hr1p6.9p10L1 (polyadenylation signal from p10 gene) |
| 53 | polhAc-ie-01/hr1p6.9p10VP60 (polyadenylation signal from p10 gene) |
| 54 | polhAc-ie-01/hr1p6.9p10L1 (SV40 polyadenylation signal) |
| 55 | polhAc-ie-01/hr1p6.9p10VP60 (SV40 polyadenylation signal) |
| 56 | polhAc-ie-01/hr1p6.9p10Cap (SV40 polyadenylation signal) |

All sequences of the invention include variants thereof that substantially retain the functional activity of the parental sequence.

"Variants" are nucleic or amino acids whose nucleic or amino acid sequence differs in one or more positions from the parental nucleic or amino acid sequence, whereby differences might be additions, deletions and/or substitutions of nucleic acids or amino acid residues.

The variants of the invention have preferably at least 70%, more preferably at least 80%, more preferably at least 90% and most preferably at least 95% identity (nucleic acid sequences) or similarity (amino acid sequences) to the parental sequence.

In another preferred embodiment, the variants of the invention are fragments of the nucleic acid or amino acid sequence that substantially retain their functional activity.

Nucleic and amino acid sequences of the present invention can be distinguished from other nucleic and amino acid sequences by their degree of sequence identity or similarity respectively as determined using, for example, EMBOSS Needle with the default parameters (http://www.ebi.ac.uk/Tools/psa/emboss_needle/). Methods for the generation of such variants include random or site directed mutagenesis, site-saturation mutagenesis, PCR-based fragment assembly, DNA shuffling, homologous recombination in vitro or in vivo, and methods of gene-synthesis.

Deposition of Microorganisms According to the Budapest Treaty

The plasmid containing the expression cassette polhAc-ie-01/hr1p6.9p10Cap was deposited in the Spanish Type Culture Collection (CECT) (www.cect.org); University of Valencia, Parc Cientific Universitat de València; Catedrático Agustín Escardino, 9; 46980 Paterna (Valencia), Spain, with the accession number CECT 8228 on Nov. 6, 2012.

EXAMPLES

Example 1. The Baculovirus Expression Cassette of the Invention Induces Cell Proliferation and Increases Cell Viability Through the Transcriptional Regulators Encoded by the Ac-ie-01 cDNA We observed by microscopy that recombinant baculoviruses incorporating a baculovirus expression cassette with the Ac-ie-01 cDNA have interesting properties related to a decrease in the virus-induced cytopathic effects and an increase of the cell density in cultures. To quantify these phenomena and to determine the DNA element/s responsible for such interesting properties, we generated a recombinant baculovirus expressing the transcriptional regulators encoded by the Ac-ie-01 cDNA under the control of polh promoter. As a control, the conventional recombinant baculovirus expressing the GFP protein under the control of the polh promoter was used. These baculoviruses were used to infect Sf9 cells in suspension at a low multiplicity of infection (MOI) of 0.1. The increase in cell number was studied until 48 h post-infection and cell viability was studied between 24 to 120 h post-infection. At 24 h post-infection, insect cells infected by the baculovirus overexpressing the Ac-ie-01 cDNA encoded transcriptional regulators, i.e. IE-1 and IE-0, presented an increase in cell number higher than 10% with respect to cultures infected by the control recombinant baculovirus (FIG. 1A). These differences in cell number were observed as early as 6 h post-infection (FIG. 1A). A more detailed analysis by flow cytometry of the time required for these factors to induce the observed differences in cell proliferation revealed an increase of insect cells in S phase at 3 h post-infection and then at 6 h post-infection, an increase in the number of insect cells in G1 was observed. These data imply a very early increment of the mitosis in those cultures infected by the baculovirus overexpressing the Ac-ie-01 cDNA encoding proteins (data not shown).

Fluorescence measurement was performed on a FACSCalibur™ (BD Biosciences™) flow cytometer. Cells were fixed in 70% EtOH, resuspended and incubated in the staining solution (50 µg/ml propidium iodide in PBS, 5 ug/ml RNAse). The data were gated to eliminate particles with a distinct size from cells and analyzed by plotting the cell number vs the red fluorescence from propidium iodide. 50,000 cells were counted per assay. Data analysis of the total number of cells per cell cycle phase (G1, S and G2) was made using Modfit software.

Infected cell cultures were also analyzed by Trypan blue staining to determine cell viability at different times post-infection. Interestingly, at very late times post-infection (96-120 hours), insect cells infected by the virus overexpressing the transcriptional regulators showed an increase (50-60% increase) of cell viability and integrity (FIG. 1B). This suggests that the overexpression of the transcriptional regulators of the present invention protects the cells from the baculovirus-induced cytopathic effect, allowing long-term expression. Both cell proliferation and increased cell viability after infection have important consequences in the recombinant protein productivity of the BEVS. Similar results were obtained when the overexpression of the transcriptional regulators was driven by both the pB2$_9$ or polh promoters (data not shown). Results observed in Sf9 insect cells infected in suspension were confirmed in Sf21 cells cultured in monolayer (data not shown) and also in Hi-5™ cells cultured in monolayer (FIGS. 1C and D). These figures demonstrate how the overexpression of the transcriptional regulators improves the cell integrity at late times post-infection (96 hours).

Example 2. The Baculovirus Expression Cassette of the Invention Increases the Baculovirus-Infected Insect Larvae Surviving Rates and Insect Biomass Recovered Using High Infectious Doses Through the Transcriptional Regulators Encoded by the Ac-ie-01 cDNA In the previous example, an advantage of baculoviruses expressing recombinant GFP protein in the context of the baculovirus cassette expressing the transcriptional regulators IE-1 and IE-0 above endogenous levels was shown in terms of viability and proliferation of insect cells.

Figure 2:
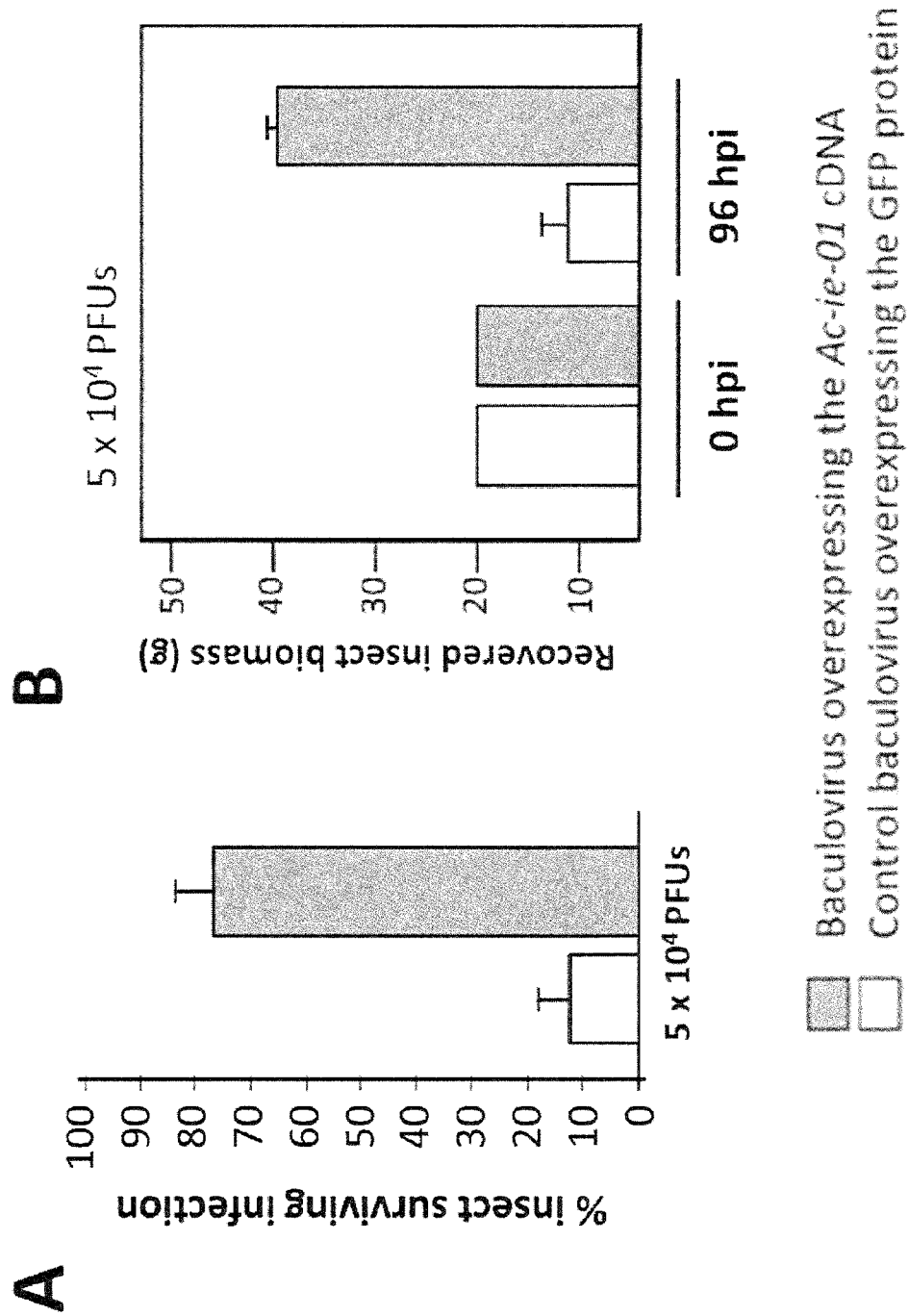
FIG. 2: A) Percentage of *T. ni* larvae surviving 96 h post-infection using $5 \times 10^4$ PFUs as the infectious dose of the baculovirus overexpressing the Ac-ie-01 cDNA under the polh promoter (polhAc-ie-01) or using a conventional baculovirus expressing GFP under the polh promoter (polhGFP). B) Insect biomass at the time of infection with the same baculoviruses as in panel A and the recovered biomass at 96 h post-infection. The infectious dose was $5 \times 10^4$ PFUs.

Using the same baculovirus constructs with the expression cassette polhAc-ie-01 or polhGFP, T. ni larvae were infected with a high infectious dose of $5 \times 10^4$ plaque forming units (PFU). Similarly to the cells infected with baculoviruses with these expression cassettes, larvae infected with the baculovirus overexpressing the Ac-ie-01 cDNA (polhAc-ie-01) also showed increased survival rates when compared to larvae infected with a conventional baculovirus expressing the GFP reporter protein under the control of the same promoter (polhGPF) (FIG. 2A). This strongly suggests that the overexpression of the transcriptional regulators used in the baculovirus expression cassette of the present invention reduces the mortality of baculovirus-infected insect larvae, allowing long-term expression (more recombinant protein production) and increasing the insect biomass recovery using high infectious doses (maximum productivity) (FIG. 2B).

Example 3. The Overexpression of the Transcriptional Regulator Proteins Encoded by Ac-ie-01 cDNA in a Baculovirus Increases Production Yields of Recombinant Proteins when their Expression is Driven by the Promoter p10 or any Chimeric Promoter Containing p10

To analyze the effect of the transcriptional regulators IE-1/IE-0 in combination with different promoters on protein expression, recombinant AcMNPV baculoviruses with the following expression cassettes were prepared:
 polhAc-ie-01/hr1polhp10GFP
 polhAc-ie-01/hr1p6.9p10GFP
 polhAc-ie-01/hr1pB2$_9$p10GFP
 polhAc-ie-01/hr1p6.9GFP
 polhAc-ie-01/hr1p10GFP
 polhAc-ie-01/hr1polhGFP
 p6.9GFP
 pB29GFP
 p10GFP
 polhGFP As a control, a conventional AcMNPV baculovirus without any foreign gene, denominated BacNi (no insert) was used.

Sf21 cells were infected with the different baculoviruses at a MOI of 5 and the increase in fluorescence was measured at 96 h post-infection. The values were normalized to the fluorescence obtained with a conventional baculovirus vector expressing the GFP under the control of the promoter polh, which was considered as 100%.

Figure 3:
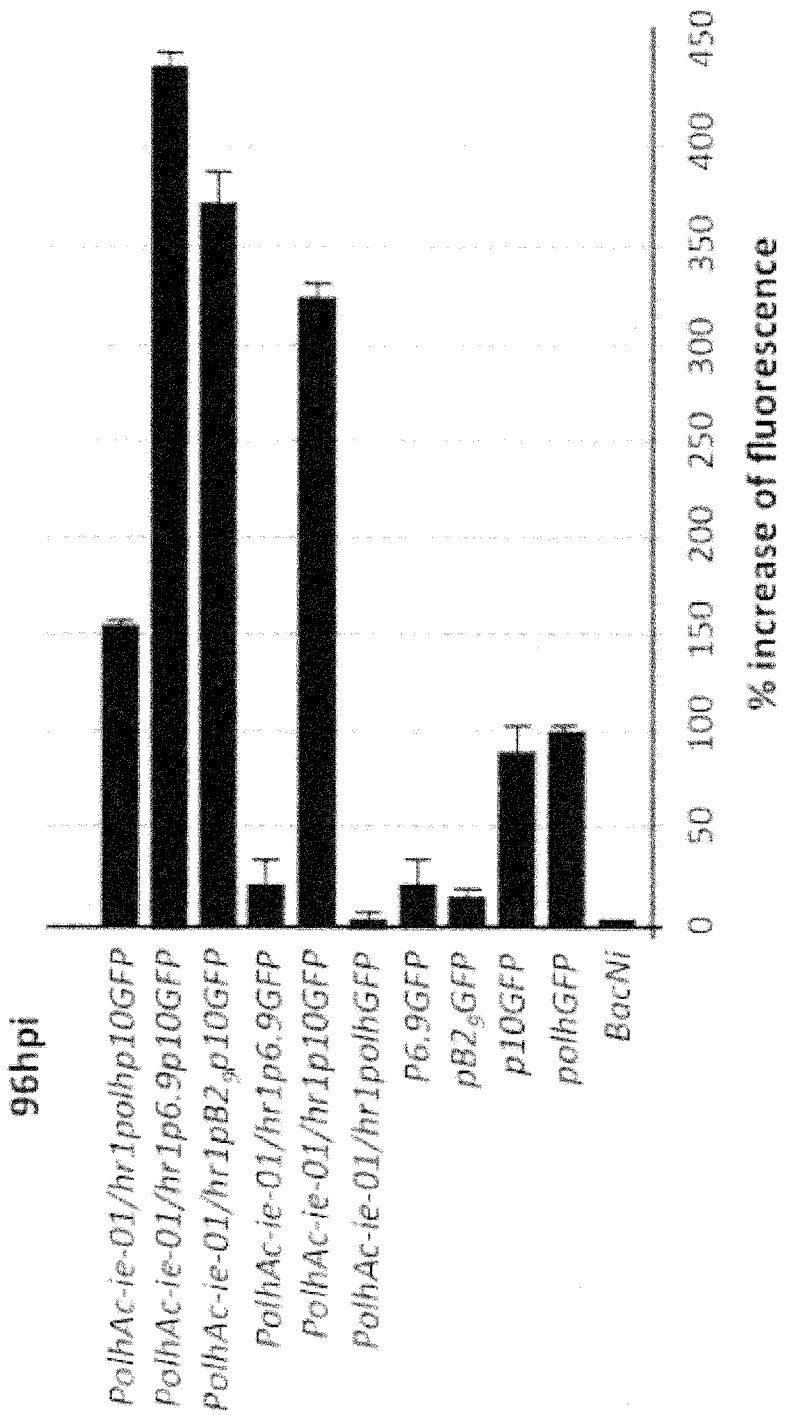
FIG. 3: The effect of the Ac-ie-01 cDNA in combination with different promoters on the expression of a reporter GFP protein was analyzed. Sf21 insect cells were infected in monolayer at a MOI of 5 with the respective recombinant baculoviruses and the increase or decrease in fluorescence was subsequently measured 96 h post-infection. The fluorescence obtained with a conventional baculovirus expressing the GFP protein under the control of polh promoter was considered as the 100% value.

As can be seen from FIG. 3, the presence of the p10 promoter (chimeric or not) is crucial for the increased expression mediated by the overexpression of Ac-ie-01 cDNA. Quite contrary, when the Ac-ie-01 cDNA is combined in the expression cassette with the promoters polh or p6.9 alone, there is either no significant increase or even a decrease in expression.

Example 4. Overexpression of Baculovirus Transcriptional Regulators IE-1 and IE-0 Potentiates the Enhancer Function of a Homologous Region Hr Functionally Linked to a Promoter Increasing the Expression of Recombinant Proteins Forming Virus-Like Particles in a Baculovirus Vector Expression System (BEVS)

Figure 4:
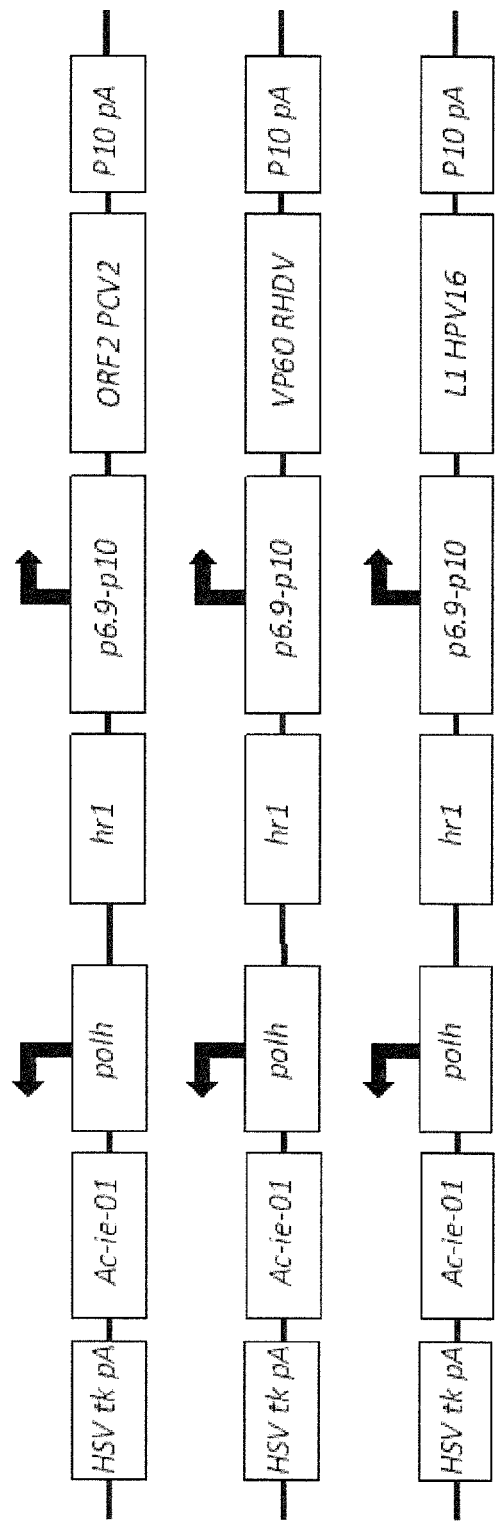
FIG. 4: Schematic representation of baculovirus recombinant DNA elements of the invention: a sequence encoding for transcriptional regulators (e.g. IE-0 and IE-1, for instance, encoded by the cDNA Ac-ie-01), which expression is driven by a promoter (e.g. polh); an enhancer homologous region (hr) sequence (e.g. hr1) upstream of the promoters (e.g. p6.9p10) driving the expression of the foreign gene, coding for a recombinant capsid protein from a porcine circovirus type 2 (ORF2 PCV2), or for the capsid protein from rabbit haemorrhagic dis MOI of 0.1 with a baculovirus expressing the VP60 protein under the control of polh promoter or by the expression cassette polhAc-ie-01/hr1p6.9p10. VLPs are shown at two magnifications. The inserts in the lower left corners of the upper panels show the Coomassie blue staining protein profiles of purified VLP preparations resolved by SDS-PAGE electrophoresis.

The expression of different proteins forming virus-like particles was compared between a conventional baculovirus and a baculovirus of the invention. The conventional baculovirus expressed the Cap, VP60 and L1 proteins under the control of the polh promoter (polhCap; polhVP60 and polhL1). The baculovirus of the invention expressed the Cap, VP60 and L1 proteins under the control of the p6.9p10 chimeric promoter that was previously synthesized. This chimeric promoter was operatively linked with the enhancer sequence homologous region hr1. The baculovirus of the invention further contained the Ac-ie-01 cDNA cloned under the control of the polh promoter to obtain the baculovirus expression cassettes polhAc-ie-01/hr1p6.9p10Cap, polhAc-ie-01/hr1p6.9p10VP60 and polhAc-ie-01/hr1p6.9p10L1 (FIG. 4). The expression of Cap, VP60 and L1 proteins were then analyzed in protein extracts from Sf9 cells cultured in suspension at different times post-infection (MOI of 0.1) with these baculoviruses. Extracts were subjected to SDS-PAGE electrophoresis and the resolved proteins were stained by Coomassie blue and/or analysed by Western blot.

Cap Protein

Figure 5:
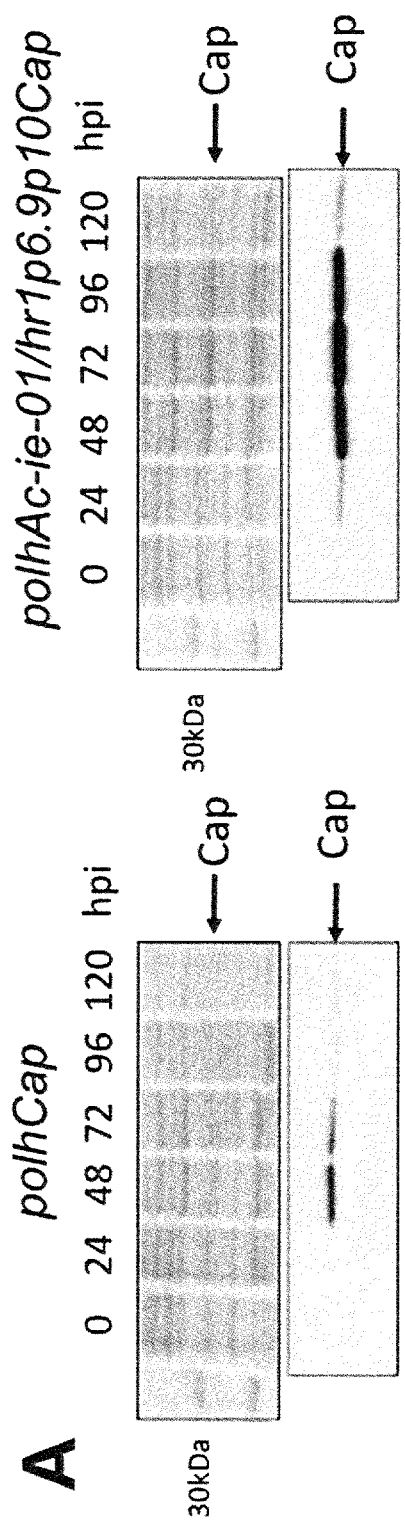
Figure 5:
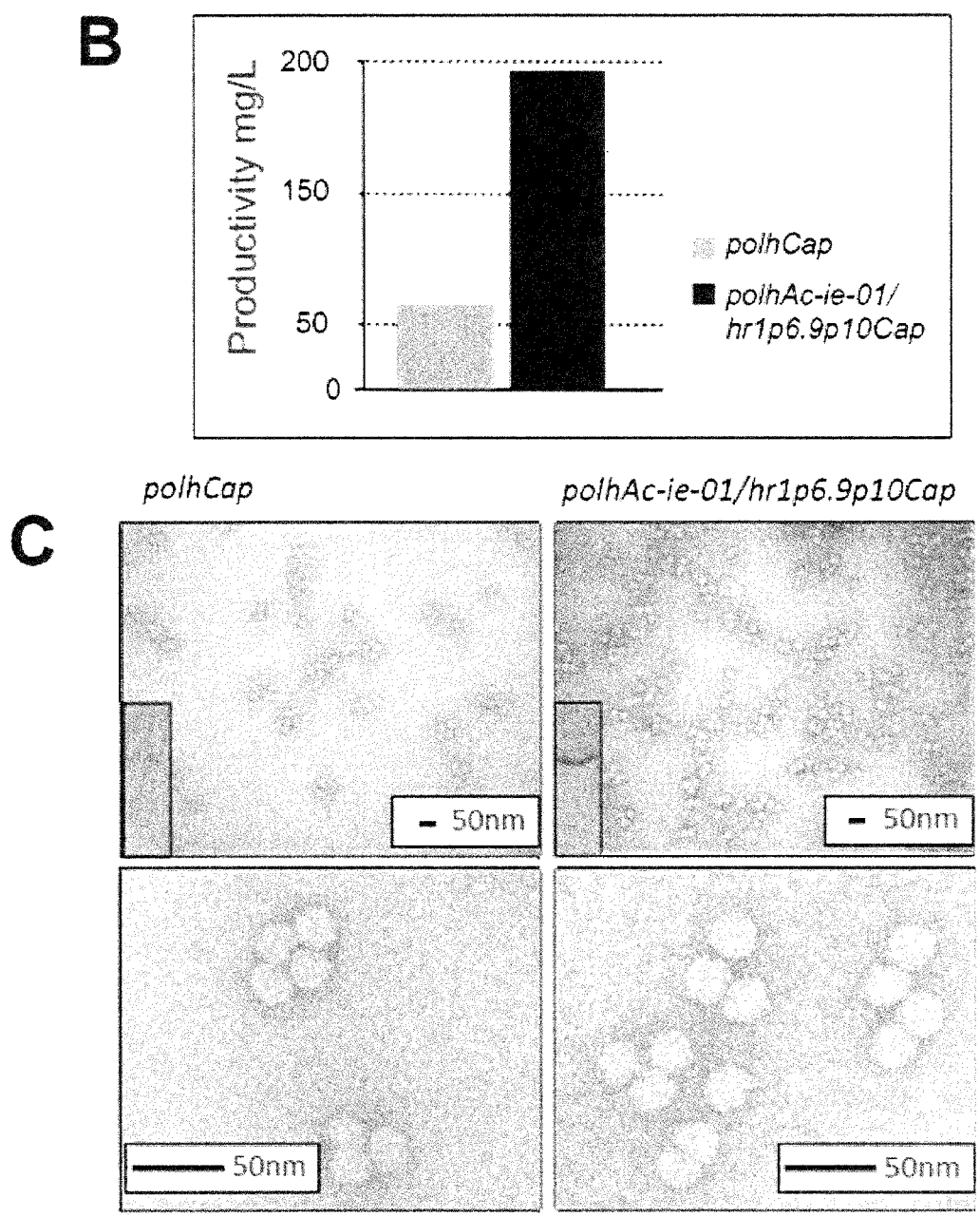

Results obtained for the Cap protein were that a more intensely stained protein band corresponding to Cap protein from porcine circovirus type 2, expressed by the baculovirus modified by the expression cassette of the present invention was observed at the different times post-infection (FIG. 5A). This clearly demonstrated that the novel expression cassette is more efficient in expressing the Cap protein. This result was found in both monolayer (Sf21) and suspension (Sf9) cells independently of the multiplicity of infection used (MOI 5 or MOI 0.1) (data not shown).

A Western blot with a monoclonal antibody against Cap protein of the same infected cell extracts also corroborated a more abundant presence of Cap protein in cells infected with the baculovirus of the invention (polhAc-ie-01/hr1p6.9p10Cap). The amount of protein was analyzed using an ECL western blotting detection system and a ChemiDoc™ XRS Gel Imaging System (Bio-Rad™, USA). Western blot reactions were studied at different times post-infection in Sf9 cells cultured in suspension as described above.

Quantification data of this analysis with the different baculoviruses obtained by the ChemiDoc™ XRS Gel Imaging System was expressed as arbitrary expression units. At 72 h post-infection, compared to a conventional baculovirus expressing the Cap protein under the control of the polh promoter, the expression level of Cap was about 4.8 times and 3.5 times higher in Sf21 monolayer (MOI of 5) and Sf9 suspension cultures (MOI of 0.1) respectively with the baculovirus modified by the expression cassette of the invention (polhAc-ie-01/hr1p6.9p10Cap) (data not shown). These differences in protein accumulation were also observed in Hi-5™ cells (data not shown), suggesting that the baculovirus expression cassette of the invention could be used to produce the recombinant protein Cap in different insect cell lines used in research and industry.

Importantly, the recombinant Cap protein expression levels mediated by the baculovirus expression cassette of the present invention were higher at any of the times post-infection analyzed (FIG. 5A). Maximum levels of expression were detected at 72 h post-infection with the baculovirus genetically modified with the expression cassette of the present invention, while the maximum level of expression with the conventional baculovirus (polhCap) was at 48 h post-infection (FIG. 5A).

A more precise quantification of the productivity of Cap protein was made by Western blot analysis with a Cap-specific monoclonal antibody of extracts from Sf9 insect cells cultured in suspension and infected by a conventional baculovirus (polhCap) or the baculovirus of the present invention (polhAc-ie-01/hr1p6.9p10Cap). The quantification was carried out with a standard curve of purified Cap protein and subsequent analyses by the ChemiDoc™ XRS Gel Imaging System (Bio-Rad™, USA). Insect cells were cultured in suspension at a density of $2\times10^6$ cells/ml and were infected at a MOI of 0.1 with each baculovirus. This demonstrated that while the productivity of Cap protein in cells infected with the conventional baculovirus was about 57 mg/L, the insect cells infected with the baculovirus of the invention were able to produce about 198 mg/L (FIG. 5B). The maximum productivities of recombinant baculoviruses were obtained at different times after infection (48 and 72 hours post-infection respectively).

Sf9 insect cells cultured in suspension were infected with a conventional baculovirus expressing the Cap protein (polhCap) or the baculovirus of the present invention expressing the Cap protein (polhAc-ie-01/hr1p6.9p10Cap). The VLPs that were formed after the expression of the Cap protein were purified. To this end, identical volumes of cell cultures were used in both cases. The cells were disrupted by a mild treatment with a non-ionic detergent and submitted after clarification to a high centrifugation speed in a sucrose gradient to purify the VLPs. Then, those VLPs were analyzed by electron microscopy by negative staining. VLPs formed by both baculoviruses were identical in size and shape, but the concentration of pseudoparticles observed reflected the differences in the Cap expression levels previously detected between the two baculoviruses. The number of VLPs produced by cells infected with the baculovirus modified with the expression cassette of the invention was higher than for the cells infected with the baculovirus expressing the Cap protein using the polh promoter (FIG. 5C). The higher number of VLPs produced by the cells infected with the baculovirus of the invention correlated with an increased expression of Cap protein in these cells, and the amount of Cap protein detected in purified VLPs analyzed by SDS-PAGE electrophoresis and Coomassie blue staining (FIG. 5C, upper panels, inserts in the lower left corners).

VP60 Protein

Figure 6:
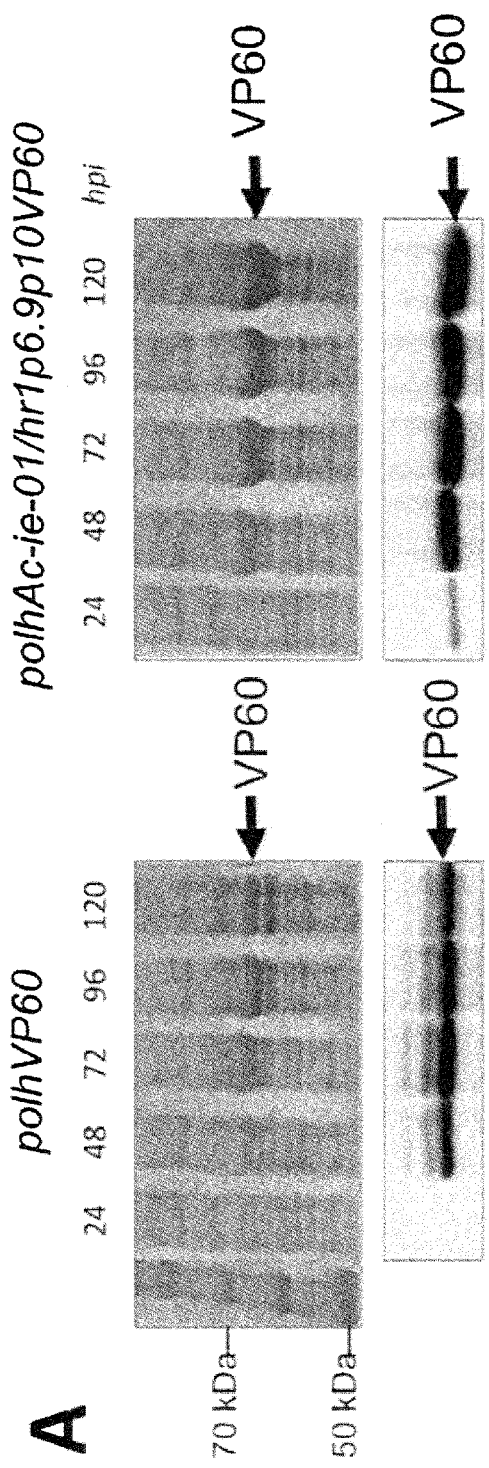
Figure 6:
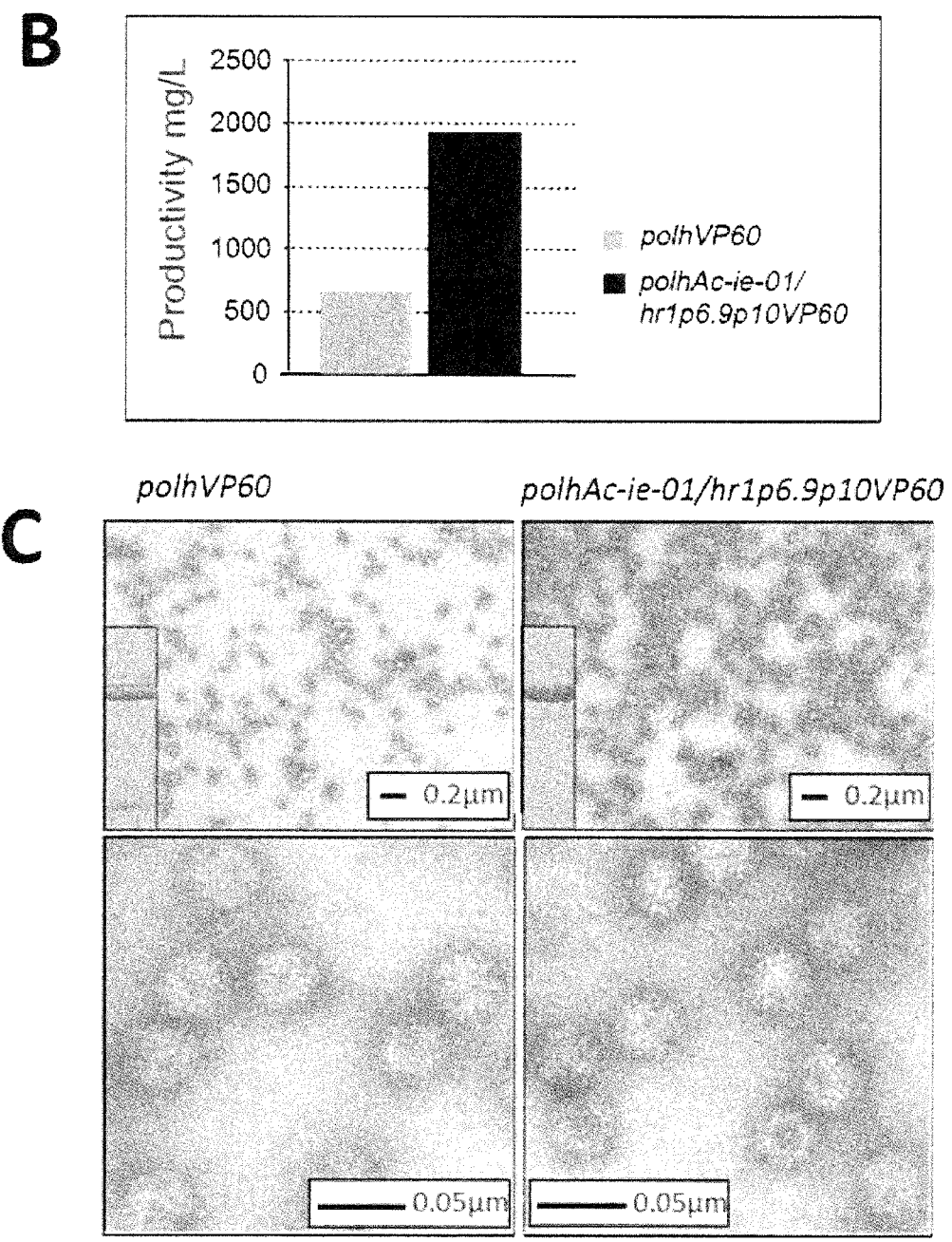

Results obtained for the VP60 protein were that a more intensely stained protein band corresponding to VP60 protein from Rabbit hameorrhagic disease virus. expressed by the baculovirus modified by the expression cassette of the present invention was observed at the different times post-infection (FIG. 6A). This clearly demonstrated that the novel expression cassette is more efficient in expressing the VP60 protein. This result was found in both monolayer (Sf21) and suspension (Sf9) cells independently of the multiplicity of infection used (MOI 5 or MOI 0.1) (data not shown).

A Western blot with a monoclonal antibody against VP60 protein of the same infected cell extracts also corroborated a more abundant presence of VP60 protein in cells infected with the baculovirus of the invention (polhAc-ie-01/hr1p6.9p10VP60). The amount of protein was analyzed using an ECL western blotting detection system and a ChemiDoc™ XRS Gel Imaging System (Bio-Rad™, USA). Western blot reactions were studied at different times post-infection in Sf9 cells cultured in suspension as described above.

Quantification data of this analysis with the different baculoviruses obtained by the ChemiDoc™ XRS Gel Imaging System was expressed as arbitrary expression units. At 72 h post-infection, compared to a conventional baculovirus expressing the VP60 protein under the control of the polh promoter, the expression level of VP60 was more than 3 times higher in Sf21 monolayer (MOI of 5) and Sf9 suspension cultures (MOI of 0.1) respectively with the baculovirus modified by the expression cassette of the invention (polhAc-ie-01/hr1p6.9p10VP60) (data not shown). These differences in protein accumulation were also observed in Hi-5™ cells (data not shown), suggesting that the baculovirus expression cassette of the invention could be used to produce the recombinant protein VP60 in different insect cell lines used in research and industry.

Figure 7:
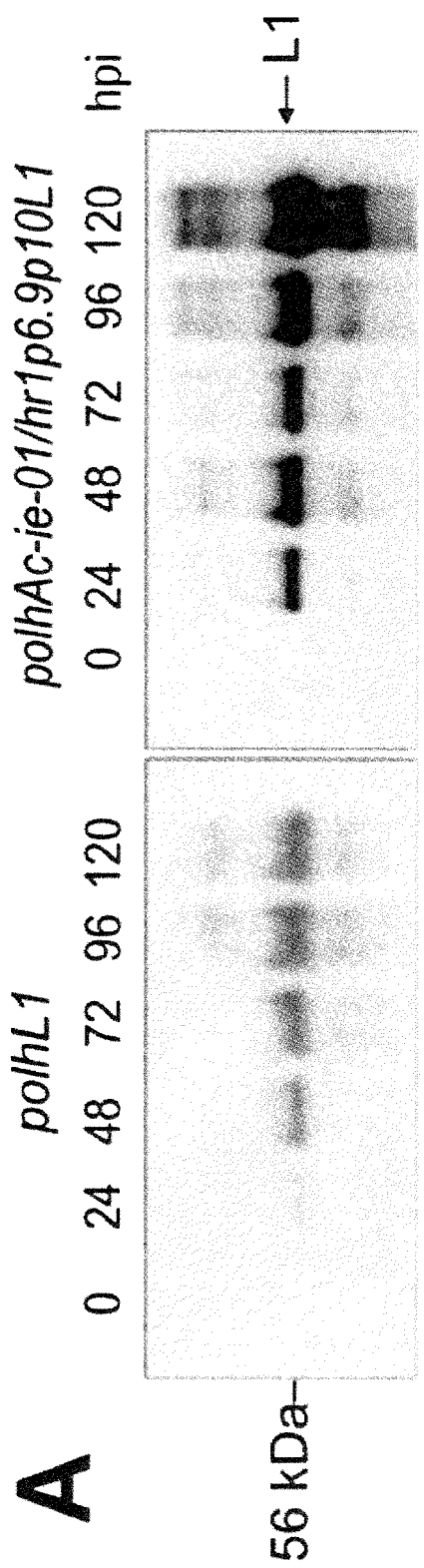
FIG. 7: A) SDS-PAGE and Western blot analysis using a monoclonal antibody against the L1 protein of ext FMDV serotype A complete genome: GenBank HQ832592.1
Figure 7:
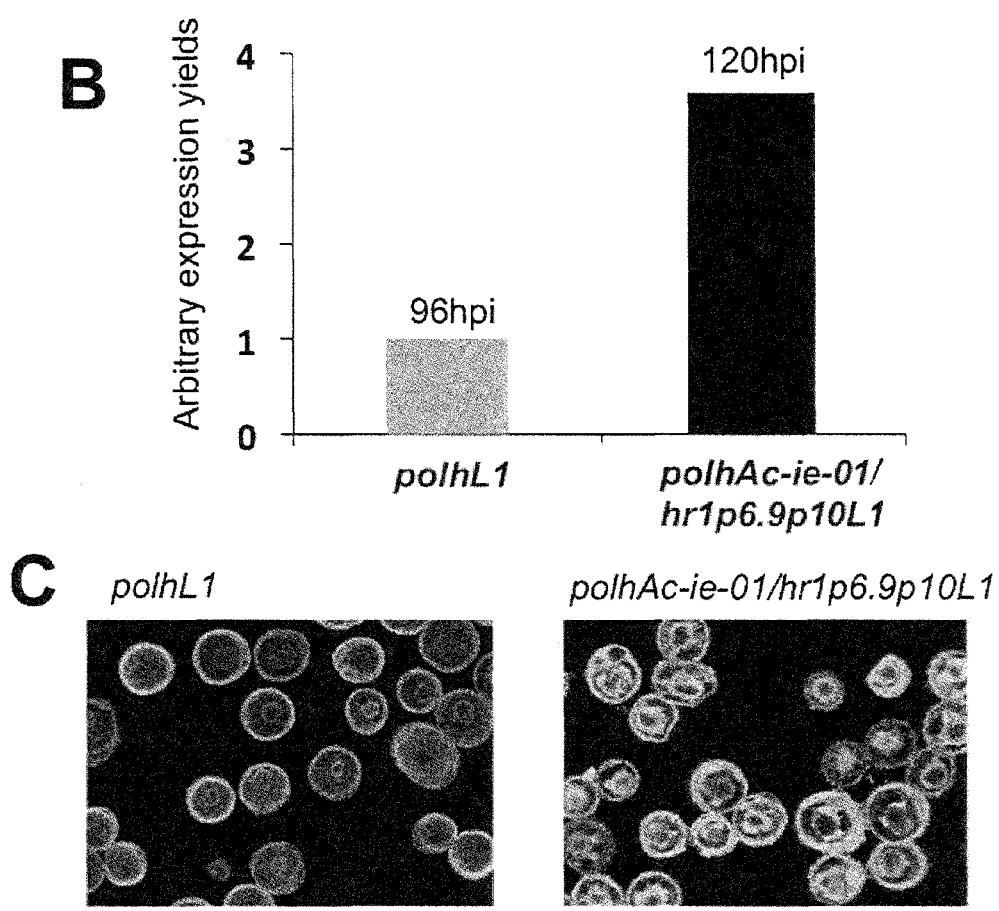

Importantly, the recombinant VP60 protein expression levels mediated by the baculovirus expression cassette of the present invention were higher at any of the times post-infection analyzed (FIG. 6A). Maximum levels of expression were detected at 120 h post-infection with the baculovirus genetically modified with the expression cassette of the present invention, while the maximum level of expression with the conventional baculovirus (polhCap) was at 72 h post-infection (FIG. 6A).

A more precise quantification of the productivity of VP60 protein was made by Western blot analysis with a VP60-specific monoclonal antibody of extracts from Sf9 insect cells cultured in suspension and infected by a conventional baculovirus (polhVP60) or the baculovirus of the present invention (polhAc-ie-01/hr1p6.9p10VP60). The quantification was carried out with a standard curve of purified VP60 protein and subsequent analyses by the ChemiDoc™ XRS Gel Imaging System (Bio-Rad™, USA). Insect cells were cultured in suspension at a density of $2\times10^6$cells/ml and were infected at a MOI of 0.1 with each baculovirus. This demonstrated that while the productivity of VP60 protein in cells infected with the conventional baculovirus was about 630 mg/L, the insect cells infected with the baculovirus of the invention were able to produce about 1,950 mg/L (FIG. 6B). The maximum productivities of recombinant baculoviruses were obtained at different times after infection (72 and 120 hours post-infection respectively).

Sf9 insect cells cultured in suspension were infected with a conventional baculovirus expressing the VP60 protein (polhVP60) or the baculovirus of the present invention expressing the VP60 protein (polhAc-ie-01/hr1p6.9p10VP60). The VLPs that were formed after the expression of the VP60 protein were purified. To this end, identical volumes of cell cultures were used in both cases. The cells were disrupted by a mild treatment with a non-ionic detergent and submitted after clarification to a high centrifugation speed in a sucrose gradient to purify the VLPs. Then, those VLPs were analyzed by electron microscopy by negative staining. VLPs formed by both baculoviruses were identical in size and shape but the concentration of pseudoparticles observed reflected the differences in the VP60 expression levels previously detected between the two baculoviruses. The number of VLPs produced by cells infected with the baculovirus modified with the expression cassette of the invention was higher than for the cells infected with the baculovirus expressing the VP60 protein using the polh promoter (FIG. 6C). The higher number of VLPs produced by the cells infected with the baculovirus of the invention correlated with an increased expression of VP60 protein in these cells, and the amount of VP60 protein detected in purified VLPs analyzed by SDS-PAGE electrophoresis and Coomassie blue staining (FIG. 6C, upper panels, inserts in the lower left corners).

L1 Protein

Results obtained for the L1 protein by Western blot analysis with a monoclonal antibody against L1 were that more intensely reacting bands corresponding to L1 protein from Human papillomavirus (HPV16) were found in cells infected by the baculovirus modified by the expression cassette of the present invention at the different times post-infection (FIG. 7A). This clearly demonstrated that the novel expression cassette (polhAc-ie-01/hr1p6.9p10L1) is more efficient in expressing the L1 protein. This result was found in both monolayer (Sf21) and suspension (Sf9) cells independently of the multiplicity of infection used (MOI 5 or MOI 0.1) (data not shown).

The amount of L1 protein was analyzed using an ECL western blotting detection system and a ChemiDoc™ XRS Gel Imaging System (Bio-Rad™, USA). Western blot reactions were studied at different times post-infection in Sf9 cells cultured in suspension as described above. Quantification data of this analysis with the different baculoviruses obtained by the ChemiDoc™ XRS Gel Imaging System was expressed as arbitrary expression units. At the moment of maximum expression levels of L1 from different baculoviruses analysed (96 and 120 hpi respectively), the expression level of L1 VP60 was more than 3.5 times higher in Sf9 suspension cultures (MOI of 0.1) with the baculovirus modified by the expression cassette of the invention (polhAc-ie-01/hr1p6.9p10L1) (FIG. 7B). These differences in protein accumulation were also observed in Hi-5™ cells (data not shown), suggesting that the baculovirus expression cassette of the invention could be used to produce the recombinant protein L1 in different insect cell lines used in research and industry.

Importantly, the recombinant L1 protein expression levels mediated by the baculovirus expression cassette of the present invention were higher at any of the times post-infection analyzed (FIG. 7A). Maximum levels of expression were detected at 120 h post-infection with the baculovirus genetically modified with the expression cassette of the present invention, while the maximum level of expression with the conventional baculovirus (polhCap) was at 96 h post-infection (FIGS. 7A and B).

Immunofluorescence staining with a L1-specific monoclonal antibody of Sf21 cells infected in monolayer at a MOI of 5 by both baculoviruses revealed clear differences in fluorescence intensity of the infected cells. Higher immunofluorescence intensities were found in cells infected by the baculovirus modified by the expression cassette of the invention (polhAc-ie-01/hr1p6.9p10L1), indicating higher L1 expression levels (FIG. 7C).

Example 5. The Baculovirus Expression Cassettes of the Invention Induce Cell Proliferation and Increase Cell Viability The baculoviruses of Example 4 containing the polhCap, polhVP60, polhL1, polhAc-ie-01/hr1p6.9p10Cap, polhAc-ie-01/hr1p6.9p10VP60 and polhAc-ie-01/hr1p6.9p10L1 expression cassettes were assessed in terms of their effect on cell growth and viability.

Figure 8A:
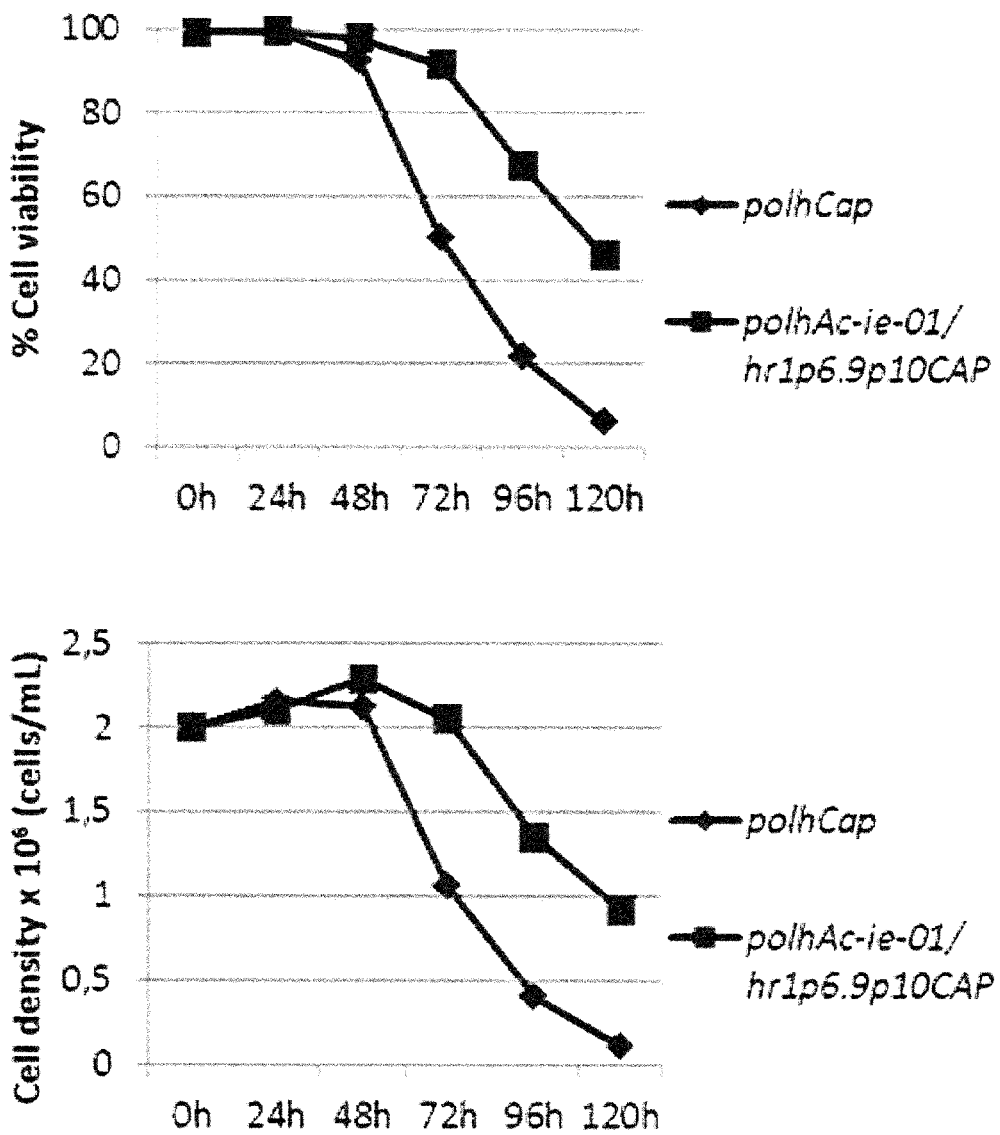
Figure 8B:
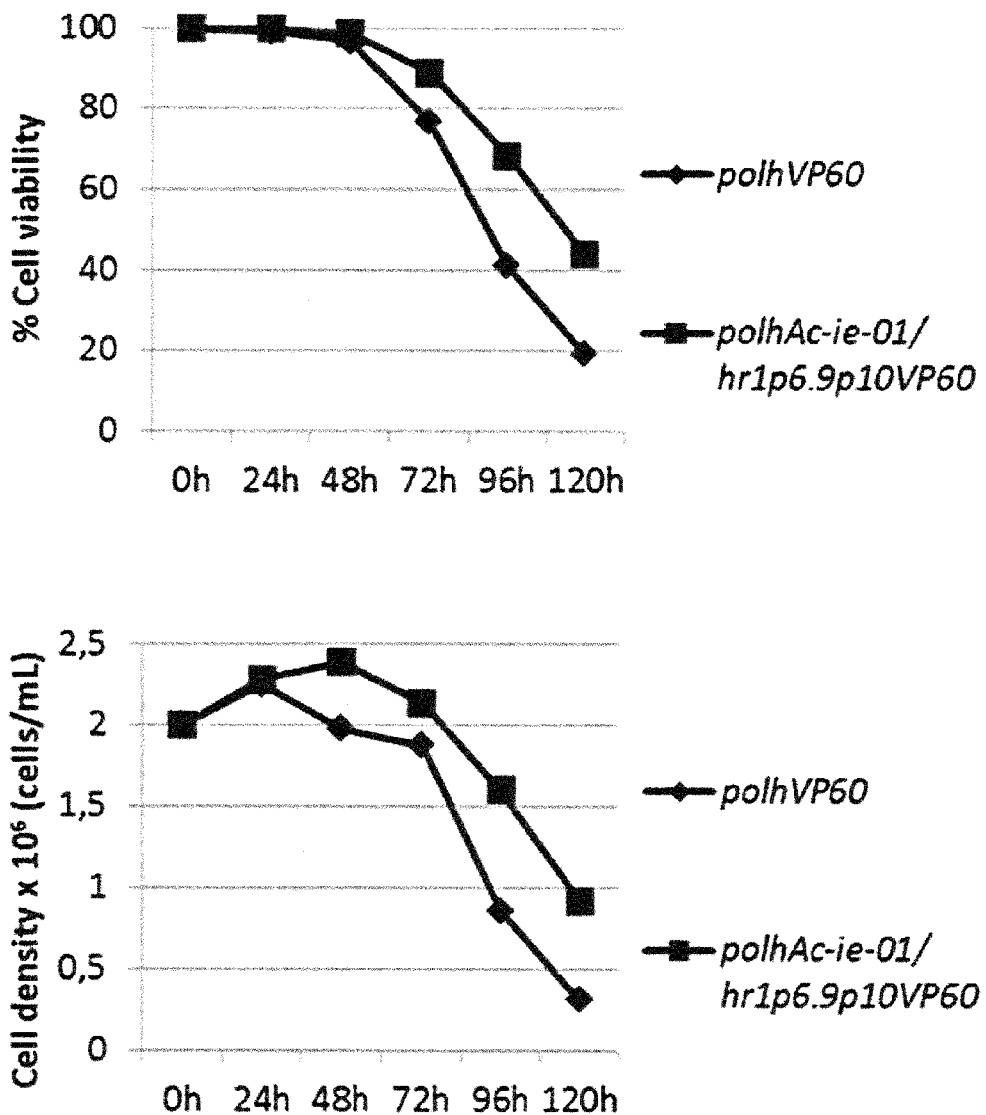
Figure 8C:
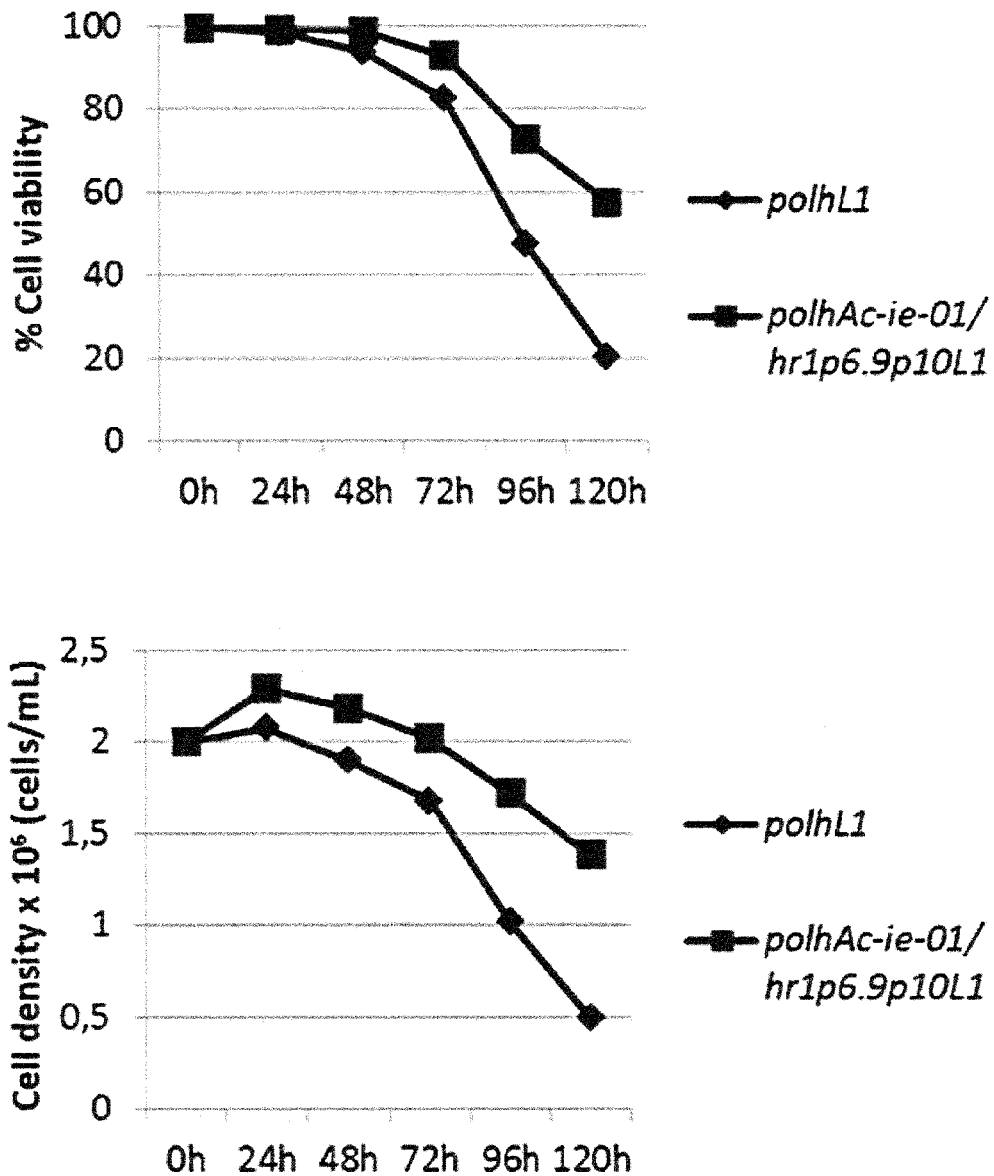

The experiment was conducted as described in Example 1 and likewise an increase in cell number, as well as an increase in viability, could be observed for the cells infected with the baculoviruses containing the expression cassette of the invention, i.e. polhAc-ie-01/hr1p6.9p10Cap (FIG. 8A), polhAc-ie-01/hr1p6.9p10VP60 (FIG. 8B) and polhAc-ie-01/hr1p6.9p10L1 (FIG. 8C).

Figure 9:
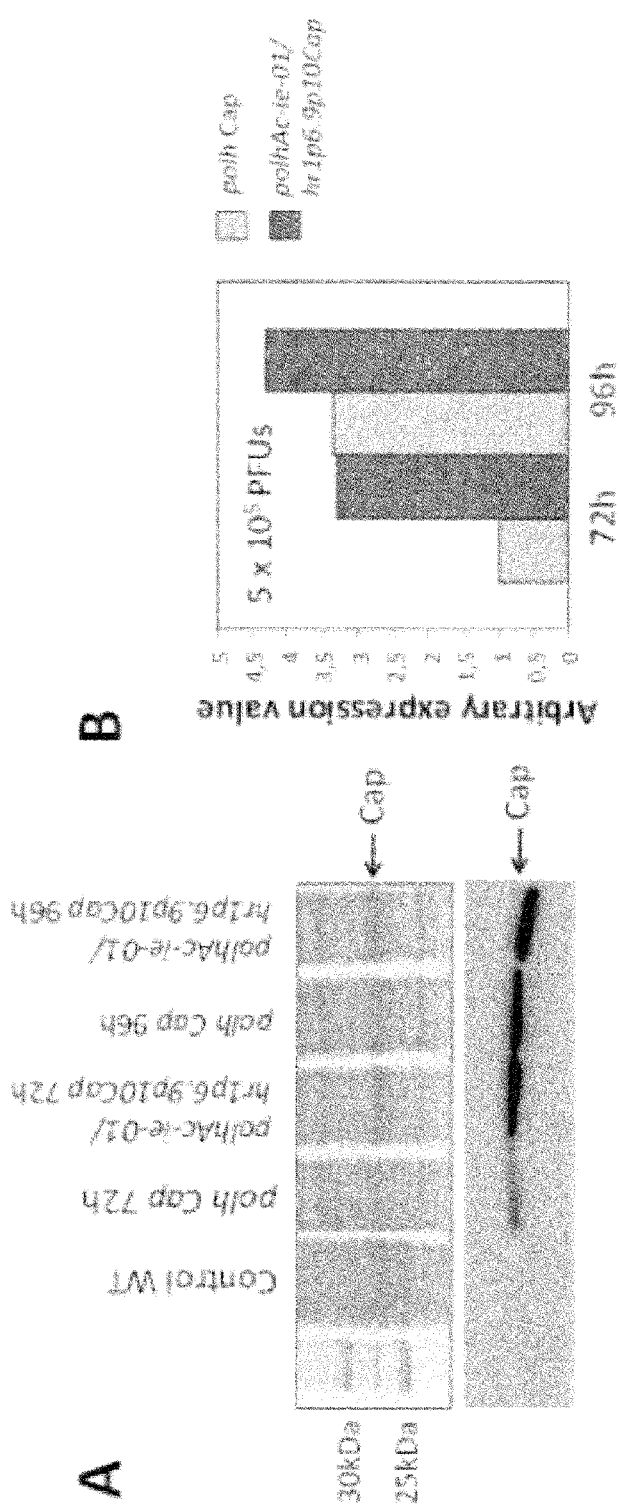

Example 6. The Expression Cassette of the Present Invention Potentiates the Productivity of Recombinant Proteins Forming Virus-Like Particles in Baculovirus-Infected Trichoplusia ni Insect Larvae The expression of Cap protein mediated by the different baculoviruses (with the conventional expression cassette and with the expression cassette of the present invention) was analyzed in infected Trichoplusia ni larvae. To this end, larvae were infected with $5 \times 10^4$ PFU of the baculovirus with the expression cassette polhCap or polhAc-ie-01/hr1p6.9p10Cap and the extracts were analyzed at 72 and 96 h post-infection by Coomassie blue staining and Western blot analysis using a monoclonal antibody against the Cap protein (FIG. 9A). The expressed Cap protein in the different extracts was also quantified by ChemiDoc™ XRS Gel Imaging System (Bio-Rad™, USA) (FIG. 9B). The expression level of Cap was increased in larval extracts by the baculovirus containing the above mentioned expression cassette of the present invention by about 325% at 72 h post-infection and by 24% at 96 h post-infection (FIG. 9B).

Figure 10:
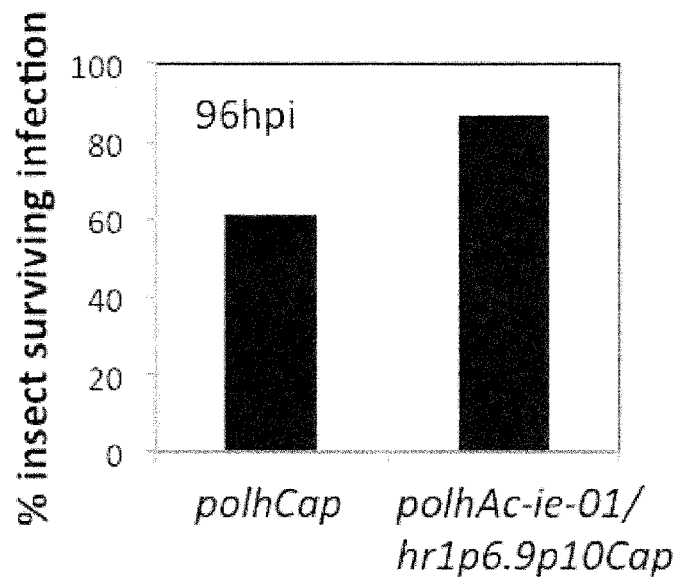

Additionally, larvae infected with the baculovirus modified by the expression cassette of the present invention presented a 30% increase in survival (FIG. 10). This represents a significant increase of insect biomass recovery during the production process.

Figure 11:
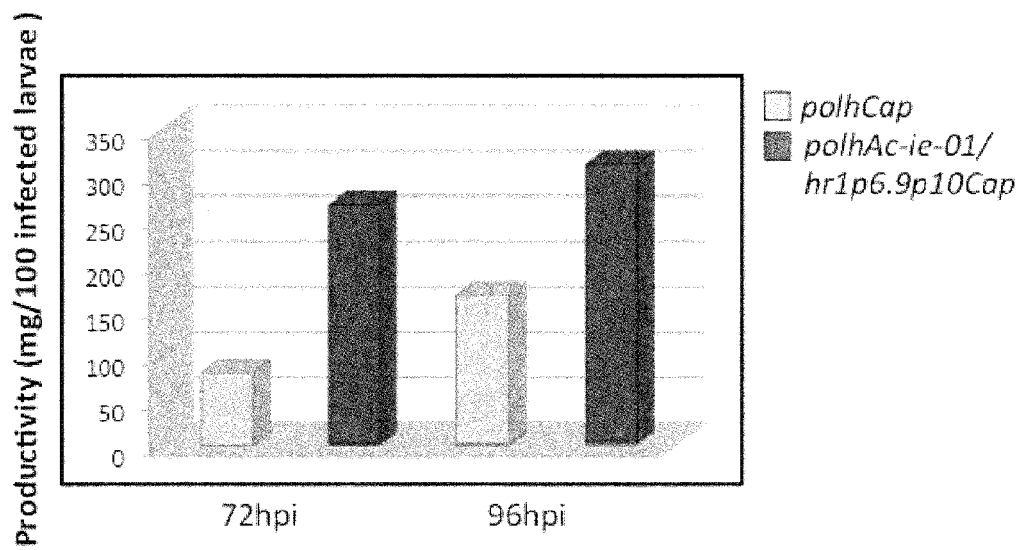

Subsequently, the productivity of 100 larvae infected with the above conventional baculovirus and the baculovirus of the invention was studied considering both the Cap production yield determined by microfluidic protein analysis (Experion™; BioRad™, USA) and the insect biomass recovered after infection. The productivity was studied at 72 and 96 h post-infection with $5 \times 10^5$ PFU of the respective baculovirus. The baculovirus containing the expression cassette of the invention, i.e. polhAc-ie-01/hr1p6.9p10Cap, increased the productivity of Cap protein in infected insect larvae with respect to the conventional baculovirus about 3.5 times at 72 h post-infection and 2 times at 96 h post-infection (FIG. 11). One hundred infected larvae with the baculovirus containing the expression cassette polhAc-ie-01/hr1p6.9p10Cap were able to produce about 300 mg of recombinant Cap protein at 96 h post-infection, whereas the larvae infected with the conventional baculovirus only produced 150 mg (FIG. 11).

Example 7. Cell Culture and Viruses

The Spodoptera frugiperda Sf21 or Sf9 cell lines were cultured in 6-well tissue culture plates ($1 \times 10^6$ cells/well) in TNM-FH insect medium (Pan Biotech™, Germany) containing 10% heat-inactivated fetal bovine serum (Pan Biotech™ Germany) at 27° C.

Confluent Sf9 or Sf21 cells in monolayer ($1 \times 10^6$ cells/well) were infected with the baculoviruses at different multiplicities of infection (from 0.01 to 10). In suspension, Sf9 cells ($2 \times 10^6$ cells/ml) were infected equally at different multiplicities of infection. Infected cells were analysed from 16 to 120 h post-infection.

Example 8. Generation of the Cloning and Donor Vectors of the Invention

A pUC57 plasmid containing the baculovirus expression cassette of the present invention was used as the cloning vector. The gene encoding the Cap protein (ORF2 from porcine circovirus type 2), the gene encoding the VP60 protein (rabbit haemorrhagic disease virus) or the gene encoding the L1 protein (human papillomavirus 16) were cloned into the MCS of a cloning plasmid using the Xho I and Nco I restriction sites. After introduction of the VLP-forming protein encoding genes, the cloning vector becomes the donor vector.

The baculovirus expression cassette in the donor vector is flanked by specific restriction sites (for example BglIII and BstZ17I at the 5'-terminal end and Bgl II and Sgf I at the 3'-terminal end) to facilitate subcloning into a transfer vector of a commercial baculovirus generation system (for example, based on transposition such the "Bac-to-Bac®" system; Invitrogen™).

Example 9. Generation of the Transfer Vectors of the Invention

The transfer vectors were generated by digesting the above donor vectors with BstZ17I at the 5'-terminal end of the expression cassette and with Hind III at the 3'-terminal end of the expression cassette. In this case, as a result of the subcloning, the SV40 polyadenylation signal of the baculovirus expression cassette is exchanged by the SV40 polyadenlation signal from the transfer vector. They were then cloned into the transfer vector pFastBac™1 that was also digested with the same enzymes. Apart from this, all the elements of the expression cassette are included in the pFastBac transfer vector, substituting the polh promoter and MCS of the original commercial transfer vector.

Example 10. Generation of the Baculovirus Expression Vectors of the Invention Using the "Bac-to-Bac®" System The modified transfer vectors pFastBac™1 of Example 9 were used to generate recombinant baculoviruses by the "Bac-to-Bac®" Baculovirus Expression System. More specifically, the modified transfer vectors were used to transform the E. coli host strain DH10Bac™ that contains a baculovirus shuttle vector (bacmid) and a helper plasmid, and allows the generation of the recombinant bacmids following transposition of the expression cassette. The DNA of the recombinant bacmids containing the baculovirus expression cassette of the present invention were then used to transfect insect Sf21 cells using Cellfectin®. 72 h post-transfection, cells were harvested and the first recombinant baculoviruses generation were obtained. These recombinant baculoviruses could then be further amplified and/or titered following conventional protocols.

For the baculoviruses of the invention that were used in Examples 4, 5 and 6, i.e. polhAc-ie-01/hr1p6.9p10Cap, polhAc-ie-01/hr1p6.9p10VP60 and polhAc-ie-01/hr1p6.9p10L1 the Ac-ie-01 cDNA was cloned under the control of the polh promoter. In the same baculoviruses, but in another locus, the Cap, VP60 or L1 encoding genes were cloned downstream of the hr1p6.9p10 chimeric promoter that was previously synthesized and contains the homologous region hr1 operatively linked to the promoters p6.9 and p10. A schematic representation of the resulting baculovirus expression cassettes of the present invention is shown in FIG. 4. The expression cassette of this baculovirus, i.e. polhAc-ie-01/hr1p6.9p10Cap, is represented by SEQ ID NO: 30. Specifically, a version of this expression cassette with a Cap gene polyadenylation signal from SV40 was used in the Examples (SEQ ID NO: 56). Also the expression cassettes polhAc-ie-01/hr1p6.9p10VP60 and polhAc-ie-01/hr1p6.9p10L1 of the Examples were used with a SV40 polyadenylation signal and are represented by SEQ ID NO: 55 and 54, respectively.

Likewise, the other baculoviruses were generated by the same methodology of Examples 8-10.

Example 11. Protein Sample Preparation

Infected cells from each time point ($1\times10^6$) were harvested and centrifuged at 14000×g for 5 min. at 4° C. The supernatants were removed and the cell pellets were resuspended in PBS and subjected to three cycles of freezing (−196° C.) and thawing (37° C.). Cellular debris was removed by centrifugation.

Example 12. Time-Course Study of Protein Expression

Sf9, Sf21 or Hi-5™ cells were infected with the different recombinant baculoviruses expressing Cap protein under the control of different regulatory, enhancer and promoter elements, using a MOI of 5 or 0.1 as indicated. Cell cultures were harvested at various time points (24, 48, 72, 96 and 120 h post-infection) and the recombinant proteins' expression was analyzed by SDS-PAGE followed by Coomassie blue staining and/or Western blot.

Quantification of the recombinant proteins was carried out by two methodologies. One involved the use of a quantitative Western blot with a specific monoclonal antibody and subsequent analysis by the ChemiDoc™ XRS Gel Imaging System (Bio-Rad™, USA) using purified counterpart proteins to carry out a standard quantification curve. A second technique involved the use of Pro260 chips (Bio-Rad™) and capillary electrophoresis using the Experion™ system (Bio-Rad™), according to the manufacturer's instructions. The electrophoresis of the samples was made through microchannels by controlling the applied voltage and electric power. The microfluidic chip allowed several sequential procedures including separation, staining, destaining, detection and basic data analysis without any need of user's intervention. The Experion™ system resolved and quantified protein samples from 10 to 260 kDa in size, with a high sensitivity, comparable to colloidal Coomassie blue SDS-PAGE gel staining. For quantification, a Pro260 ladder was used in the Experion™ system, which is a modified version of the Precision Plus Protein™ standard that has been optimized for use in that system.

Example 13. Rearing and Infection of Insect Larvae

Trichoplusia ni (cabbage looper) larvae were reared under level 2 biosafety conditions. Eggs were placed into specially designed larva developmental cages containing an artificial insect diet and were kept in growth chambers at 22° C. under controlled humidity (50%) and light period (8 h/day) conditions.

Trichoplusia ni (Cabbage looper) fifth-instar larvae (last instar larvae before pupation), were used for all experiments. The standard weight of each larva was approximately 120-130 mg and larvae were injected near the proleg (anterior to the body cavity) with 5 µl of recombinant baculoviruses diluted to reach the number of PFU per dose selected. Larvae were processed at 72 or 96 h post-infection. The collected larvae were frozen immediately to be stored at −20° C. until they were processed for recombinant protein quantification. Total soluble, non-denatured proteins (TSNDPs) from frozen T. ni larvae infected by the baculoviruses were obtained by homogenization using a Bag Mixer® blender (Interscience™, France) for 2 min. Extraction buffer was composed of PBS 1×, Triton X-100 at 0.01%, Complete protease inhibitor cocktail (Roche™, Germany), and DTT 25 mM.

Example 14. Western Blot Analysis

Total soluble protein fractions (10 µg) from cells infected with the recombinant baculoviruses were resolved in 15% SDS-PAGE gels. Gels were stained by the Coomassie blue staining method or transferred to nitrocellulose membranes. Western blots were probed with the anti-Cap monoclonal antibody (I36A; Ingenasa™, Spain) at 1:1000 or with the anti L1 HPV16 monoclonal antibody (Camvir1; AbCam, USA) at 1:1000, and the immunocomplexes were visualized with anti-mouse IgG-horseradish peroxidase (HRP)-labeled conjugate (KPL™, UK), diluted 1:2,000 or by an anti-rabbit IgG-horseradish peroxidase (HRP)-labeled conjugate (KPL™, UK), diluted 1:2,000 respectively as a secondary antibody. Protein bands were detected using an ECL western blotting detection system and analyzed by the ChemiDoc™ XRS Gel Imaging System (Bio-Rad™, USA).

BIBLIOGRAPHY

1. Nettleship, J. E., Assenberg, R., Diprose, J. M., Rahman-Hug, N., Owens, R. J. Recent advances in the production of proteins in insect and mammalian cells for structural biology. J. Struct. Biol. 2010, 172, 55-65.
2. Gomez-Casado E, Gomez-Sebastian S, Núñez M C, Lasa-Covarrubias R, Martinez-Pulgarín S, Escribano J M. Insect larvae biofactories as a platform for influenza vaccine production. *Protein Expr Purif.* 79: 35-43. 2011.
3. Smith, G. E., M. D. Summers, and M. J. Fraser. 1983. Production of human beta interferon in insect cells infected with a baculovirus expression vector. Mol. *Cell. Biol.* 3: 2156-21 65.
4. Hitchman R B, Possee R D, King L A. Baculovirus expression systems for recombinant protein production in insect cells. Recent Pat Biotechnol. 2009; 3(1):46-54.
5. Hashimoto, Y., S. Zhang, Y. R. Chen and G. W. Blissard (2012). "BTI-Tnao38, a new cell line derived from *Trichoplusia ni*, is permissive for AcMNPV infection and produces high levels of recombinant proteins." BMC Biotechnol 12: 12.
6. Taticek R A, Choi C, Phan S E, Palomares L A, Shuler M L. Comparison of growth and recombinant protein expression in two different insect cell lines in attached and suspension culture. *Biotechnol. Prog.* 2001, 17 (4), 676-684.
7. Hill-Perkins M S, Possee R D. A baculovirus expression vector derived from the basic protein promoter of *Autographa californica* nuclear polyhedrosis virus. J Gen Virol. 1990, 71 (Pt 4):971-6.
8. Taryn M S, Huijskens I, Willis L G, Theilmann D A. The *Autographa californica* multiple nucleopolyhedrovirus ie0-ie1 gene complex is essential for wild-type virus replication, but either IE0 or IE1 can support virus growth. Journal of Virology, 2005, Vol. 79 (No. 8): 4619-4629
9. Passarelli, A. L., and L. K. Miller. Three baculovirus genes involved in late and very late gene expression: ie-1, ie-n, and lef-2. J. Virol. 1993, 67:2149-2158.
10. Rodems, S. M., S. S. Pullen, and P. D. Friesen. DNA-dependent transregulation by IE1 of *Autographa californica* nuclear polyhedrosis virus: IE1 domains required for transactivation and DNA binding. J. Virol. 1997, 71: 9270-9277.
11. Lin X, Chen Y, Yi Y, Zhang Z: Baculovirus immediately early 1, a mediator for homologous regions enhancer function in trans. Virol J 2010, 7:32.
12. Okano K, Mikhailov V S, Maeda S: Colocalization of baculovirus IE-1 and two DNA-binding proteins, DBP and LEF-3, to viral replication factories. *Journal of virology* 1999, 73(1):110-119.

The invention claimed is:

1. An expression cassette for a baculovirus expression vector system (BEVS), comprising a first nucleic acid sequence and a second nucleic acid sequence;
wherein the first nucleic acid sequence is selected from the group consisting of:
(a) a nucleic acid sequence comprising the sequence of SEQ ID NO: 1;
(b) a nucleic acid sequence having at least 95% sequence identity to the sequence of SEQ ID NO:1 and encoding a protein able to function as a transcriptional regulator in a baculovirus;
(c) a nucleic acid sequence encoding an amino acid sequence comprising the sequence of SEQ ID NO: 6; and
(d) a nucleic acid sequence encoding a protein able to function as a transcriptional regulator in a baculovirus and having at least 95% sequence identity to the sequence of SEQ ID NO: 6;
wherein the second nucleic acid sequence directs the expression of a recombinant protein, wherein the recombinant protein is a virus-like particle protein;
wherein the expression cassette for BEVS also comprises at least one recombinant homologous region (hr) as enhancer region operably linked to a promoter suitable for driving the expression of the recombinant protein;
wherein the promoter suitable for driving the expression of the recombinant protein comprises a nucleic acid sequence selected from the group consisting of:
(a) a nucleic acid sequence comprising the sequence of SEQ ID NO:13; and
(b) a nucleic acid sequence able to function as a promoter in a baculovirus and having at least 95% sequence identity to the sequence of SEQ ID NO:13.

2. The expression cassette according to claim 1, wherein the recombinant protein is selected from the group consisting of:

(a) porcine circovirus capsid protein;
(b) foot and mouth disease virus VP1, VP3 and VP0 protein;
(c) canine parvovirus VP1 and VP2 protein;
(d) porcine parvovirus VP1 and VP2 protein;
(e) human norovirus (genogroup I or II) capsid protein;
(f) calicivirus capsid protein;
(g) human papillomavirus L1 protein;
(h) hepatitis E protein E2;
(i) infectious bursal disease virus VP1, VP2 and VP3 protein;
(j) astrovirus ORF2-encoded protein;
(k) influenza virus HA, NA and M1 protein;
(l) Hepatitis B core and surface antigen;
(m) parvovirus VP1 and VP2 protein; and
(n) rabbit calicivirus VP60 protein.

3. The expression cassette according to claim 2, wherein the porcine circovirus capsid protein is derived from porcine circovirus type 2.

4. The expression cassette according to claim 2, wherein the human papillomavirus L1 protein is derived from human papillomavirus type 16.

5. The expression cassette according to claim 2, wherein the rabbit calcivirus VP60 protein is derived from rabbit hemorrhagic disease virus.

6. The expression cassette according to claim 1, wherein the recombinant homologous region (hr) is selected from the group consisting of:
(a) a nucleic acid sequence comprising SEQ ID NO: 27; and
(b) a nucleic acid sequence able to function as an enhancer homologous region in a baculovirus and having at least 70% sequence identity with SEQ ID NO: 27.

7. A cloning vector, transfer vector, bacmid, recombinant baculovirus or cell comprising the expression cassette of claim 1, wherein the transfer vector further comprises a nucleic acid sequence suitable for integration or transposition in a baculovirus genome.

8. A culture media comprising the expression cassette according to claim 1.

9. An in vitro method for producing a recombinant protein comprising expressing said protein from the expression cassette according to claim 1 and purifying said protein.

10. A vaccine comprising the recombinant protein produced by the method according to claim 9.

11. An expression cassette for a baculovirus expression vector system (BEVS), comprising a first nucleic acid sequence selected from the group consisting of:
  (a) a nucleic acid sequence comprising the sequence of SEQ ID NO:19; and
  (b) a nucleic acid sequence substantially retaining the activity of the functional elements and having at least 95% sequence identity to the sequence of SEQ ID NO:19; and
a second nucleic acid sequence that encodes a recombinant protein, wherein the recombinant protein is a virus-like particle;
wherein the first nucleic acid sequence is operably linked to the expression of the second nucleic acid sequence.

12. An expression cassette for a baculovirus expression vector system (BEVS), comprising a nucleic acid sequence selected from the group consisting of:
  (a) a nucleic acid sequence comprising the sequence of SEQ ID NO:51; and
  (b) a nucleic acid sequence substantially retaining the activity of the functional elements and having at least 95% sequence identity to the sequence of SEQ ID NO:51.

* * * * *

SEQUENCE LISTING

```
<160> NUMBER OF SEQ ID NOS: 56

<210> SEQ ID NO 1
<211> LENGTH: 1911
<212> TYPE: DNA
<213> ORGANISM: Autographa californica nucleopolyhedrovirus

<400> SEQUENCE: 1
atgatccgta catccagcca cgtcctgaac gtccaagaaa acatcatgac ttccaactgt      60
gcttccagcc cctactcctg tgaggccact tcagcctgcg ctgaggccca gcaactgcag     120
gtggacacag gtggcgataa gatcgtgaac aaccaggtca ccatgactca aatcaacttc     180
aacgcttcct acacctctgc cagcactccc tctcgtgcta gttcgacaa ctcatactcg     240 gagttctgcg acaagcaacc taacgattac ttgtcttact acaaccaccc aacccggac     300 ggagctgata ctgtcatctc cgactctgaa accgctgccg ctagcaactt cctcgcctca     360
gttaactcgc tcactgacaa cgatttggtg gagtgtctgc tcaagaccac tgacaacctg     420
gaggaagctg tgtcctctgc ctactacagc gagtcactcg aacagccagt ggtcgaacaa     480
ccctctccta gctcagctta ccacgccgag tccttcgaac actctgctgg tgtcaaccag     540
ccgtcggcca caggcaccaa gaggaagttg gacgagtacc tggataactc caggggagtt     600
gtgggtcaat tcaacaagat caagttgaga cctaagtaca agaagagcac catccagtca     660
tgcgctacac tggaacaaac catcaaccac aacactaaca tctgtacagt ggcttccacc     720
caggagatca ctcactactt cacaaacgac ttcgcccct acctgatgag gttcgacgat     780
aacgactaca actcgaacag attctccgat cacatgtctg aaaccggtta ctacatgttc     840
gtcgttaaga agtccgaggt gaagcctttc gaaatcatct tcgccaagta cgtctctaac     900
gtggtctacg agtacacaaa caactactac atggttgaca accgtgtgtt cgttgtgacc     960
```

| | |
|---|---|
| ttcgataaga tccgcttcat gatcagctac aacctggtta aggagactgg catcgaaatc | 1020 |
| ccacactcac aggacgtctg caacgatgag accgccgctc aaaactgcaa gaagtgtcac | 1080 |
| ttcgtggacg tccaccacac attcaaggcc gctctgacct cctacttcaa cctcgatatg | 1140 |
| tactacgctc agacaacctt cgtgaccttg ctgcaatcac tcggcgagcg taagtgtgga | 1200 |
| ttcctcttgt cgaagttgta cgagatgtac caggacaaga acctcttcac tttgcccatc | 1260 |
| atgctgagcc gcaaggaatc aaacgagatc gaaaccgcct ctaacaactt cttcgtctcg | 1320 |
| ccatacgttt cccagatcct caagtactcg gagtccgtcc aattcccgga caaccctccc | 1380 |
| aacaagtacg tcgttgataa cctgaacctc atcgtgaaca agaagagcac tctgacatac | 1440 |
| aagtactcgt ccgtcgctaa cctgctcttc aacaactaca agtaccacga caacatcgct | 1500 |
| tctaacaaca cgccgagaa cctcaagaag gtcaagaagg aagacggaag catgcacatc | 1560 |
| gttgagcagt acttgactca aaacgtcgat aacgttaagg gtcacaactt catcgtgttg | 1620 |
| tccttcaaga cgaggaaag gctgaccatc gctaagaaga caaggagtt ctactggatc | 1680 |
| tctggcgaaa tcaaggacgt tgatgtgagc caggtcatcc aaaagtacaa cagattcaag | 1740 |
| caccacatgt tcgtgatcgg caaggtcaac cgtcgcgagt caactacact gcacaacaac | 1800 |
| ttgctgaagc tcttggcctt gatcctgcag ggactggtgc cactctccga cgccatcaca | 1860 |
| ttcgccgagc aaaagctcaa ctgcaagtac aagaagttcg agttcaacta a | 1911 |

```
<210> SEQ ID NO 2
<211> LENGTH: 1749
<212> TYPE: DNA
<213> ORGANISM: Autographa californica nucleopolyhedrovirus

<400> SEQUENCE: 2
```

| | |
|---|---|
| atgactcaaa tcaacttcaa cgcttcctac acctctgcca gcactccctc tcgtgctagc | 60 |
| ttcgacaact catactcgga gttctgcgac aagcaaccta acgattactt gtcttactac | 120 |
| aaccacccaa ccccggacgg agctgatact gtcatctccg actctgaaac cgctgccgct | 180 |
| agcaacttcc tcgcctcagt taactcgctc actgacaacg attggtgga gtgtctgctc | 240 |
| aagaccactg acaacctgga ggaagctgtg tcctctgcct actacagcga gtcactcgaa | 300 |
| cagccagtgg tcgaacaacc ctctcctagc tcagcttacc acgccgagtc cttcgaacac | 360 |
| tctgctggtg tcaaccagcc gtcggccaca ggcaccaaga ggaagttgga cgagtacctg | 420 |
| gataactccc agggagttgt gggtcaattc aacaagatca agttgagacc taagtacaag | 480 |
| aagagccacca tccagtcatg cgctacactg gaacaaacca tcaaccacaa cactaacatc | 540 |
| tgtacagtgg cttccacca ggagatcact cactacttca caaacgactt cgcccctac | 600 |
| ctgatgaggt cgacgataa cgactacaac tcgaacagat tctccgatca catgtctgaa | 660 |
| accggttact acatgttcgt cgttaagaag tccgaggtga agccttcga atcatcttc | 720 |
| gccaagtacg tctctaacgt ggtctacgag tacacaaaca actactacat ggttgacaac | 780 |
| cgtgtgttcg ttgtgacctt cgataagatc cgcttcatga tcagctacaa cctggttaag | 840 |
| gagactggca tcgaaatccc acactcacag gacgtctgca cgatgagac cgccgctcaa | 900 |
| aactgcaaga gtgtcactt cgtggacgtc caccacacat tcaaggccgc tctgacctcc | 960 |
| tacttcaacc tcgatatgta ctacgctcag acaaccttcg tgaccttgct gcaatcactc | 1020 |
| ggcgagcgta agtgtggatt cctcttgtcg aagttgtacg agatgtacca ggacaagaac | 1080 |
| ctcttcactt tgcccatcat gctgagccgc aaggaatcaa acgagatcga aaccgcctct | 1140 |
| aacaacttct tcgtctcgcc atacgtttcc cagatcctca agtactcgga gtccgtccaa | 1200 |

```
ttcccggaca accctcccaa caagtacgtc gttgataacc tgaacctcat cgtgaacaag    1260
aagagcactc tgacatacaa gtactcgtcc gtcgctaacc tgctcttcaa caactacaag    1320
taccacgaca acatcgcttc taacaacaac gccgagaacc tcaagaaggt caagaaggaa    1380
gacggaagca tgcacatcgt tgagcagtac ttgactcaaa cgtcgataa cgttaagggt    1440 cacaacttca tcgtgttgtc cttcaagaac gaggaaaggc tgaccatcgc taagaagaac    1500
aaggagttct actggatctc tggcgaaatc aaggacgttg atgtgagcca ggtcatccaa    1560
aagtacaaca gattcaagca ccacatgttc gtgatcggca aggtcaaccg tcgcgagtca    1620
actacactgc acaacaactt gctgaagctc ttggccttga tcctgcaggg actggtgcca    1680
ctctccgacg ccatcacatt cgccgagcaa aagctcaact gcaagtacaa gaagttcgag    1740
ttcaactaa                                                            1749

<210> SEQ ID NO 3
<211> LENGTH: 1911
<212> TYPE: DNA
<213> ORGANISM: Autographa californica nucleopolyhedrovirus

<400> SEQUENCE: 3
atgatccgta catccagcca cgtcctgaac gtccaagaaa acatcatgac ttccaactgt      60
gcttccagcc cctactcctg tgaggccact tcagcctgcg ctgaggccca gcaactgcag     120
gtggacacag gtggcgataa gatcgtgaac aaccaggtca ccatgactca aatcaacttc     180
aacgcttcct acacctctgc cagcactccc tctcgtgcta gcttcgacaa ctcatactcg     240
gagttctgcg acaagcaacc taacgattac ttgtcttact acaaccaccc aaccccggac     300
ggagctgata ctgtcatctc cgactctgaa accgctgccg ctagcaactt cctcgcctca     360
gttaactcgc tcactgacaa cgatttggtg gagtgtctgc tcaagaccac tgacaacctg     420
gaggaagctg tgtcctctgc ctactacagc gagtcactcg aacagccagt ggtcgaacaa     480
ccctctccta gctcagctta ccacgccgag tccttcgaac actctgctgg tgtcaaccag     540
ccgtcggcca caggcaccaa gaggaagttg acgagtacc tggataactc ccagggagtt     600
gtgggtcaat tcaacaagat caagttgaga cctaagtaca agaagagcac catccagtca     660
tgcgctacac tggaacaaac catcaaccac aacactaaca tctgtacagt ggcttccacc     720
caggagatca ctcactactt cacaaacgac ttcgcccct acctgatgag gttcgacgat     780
aacgactaca actcgaacag attctccgat cacatgtctg aaaccggtta ctacatgttc     840
gtcgttaaga agtccgaggt gaagcctttc gaaatcatct tcgccaagta cgtctctaac     900
gtggtctacg agtacacaaa caactactac atggttgaca accgtgtgtt cgttgtgacc     960
ttcgataaga tccgcttcat gatcagctac aacctggtta aggagactgg catcgaaatc    1020
ccacactcac aggacgtctg caacgatgag accgccgctc aaaactgcaa gaagtgtcac    1080
ttcgtggacg tccaccacac attcaaggcc gctctgacct cctacttcaa cctcgatatg    1140
tactacgctc agacaacctt cgtgaccttg ctgcaatcac tcggcgagcg taagtgtgga    1200
ttcctcttgt cgaagttgta cgagatgtac caggacaaga acctcttcac tttgcccatc    1260
atgctgagcc gcaaggaatc aaacgagatc gaaaccgcct ctaacaactt cttcgtctcg    1320
ccatacgttt cccagatcct caagtactcg gagtccgtcc aattcccgga caaccctccc    1380
aacaagtacg tcgttgataa cctgaacctc atcgtgaaca agaagagcac tctgacatac    1440
aagtactcgt ccgtcgctaa cctgctcttc aacaactaca agtaccacga caacatcgct    1500
```

| | |
|---|---|
| tctaacaaca acgccgagaa cctcaagaag gtcaagaagg aagacggaag catgcacatc | 1560 |
| gttgagcagt acttgactca aaacgtcgat aacgttaagg gtcacaactt catcgtgttg | 1620 |
| tccttcaaga acgaggaaag gctgaccatc gctaagaaga caaggagtt ctactggatc | 1680 |
| tctggcgaaa tcaaggacgt tgatgtgagc caggtcatcc aaaagtacaa cagattcaag | 1740 |
| caccacatgt tcgtgatcgg caaggtcaac cgtcgcgagt caactacact gcacaacaac | 1800 |
| ttgctgaagc tcttggcctt gatcctgcag ggactggtgc cactctccga cgccatcaca | 1860 |
| ttcgccgagc aaaagctcaa ctgcaagtac aagaagttcg agttcaacta a | 1911 |

<210> SEQ ID NO 4
<211> LENGTH: 666
<212> TYPE: DNA
<213> ORGANISM: Autographa californica nucleopolyhedrovirus

<400> SEQUENCE: 4

| | |
|---|---|
| atgactcaaa tcaacttcaa cgcttcctac acctctgcca gcactccctc tcgtgctagc | 60 |
| ttcgacaact catactcgga gttctgcgac aagcaaccta cgattactt gtcttactac | 120 |
| aaccacccaa ccccggacgg agctgatact gtcatctccg actctgaaac cgctgccgct | 180 |
| agcaacttcc tcgcctcagt taactcgctc actgacaacg atttggtgga gtgtctgctc | 240 |
| aagaccactg acaacctgga ggaagctgtg tcctctgcct actacagcga gtcactcgaa | 300 |
| cagccagtgg tcgaacaacc ctctcctagc tcagcttacc acgccgagtc cttcgaacac | 360 |
| tctgctggtg tcaaccagcc gtcggccaca ggcaccaaga ggaagttgga cgagtacctg | 420 |
| gataactccc agggagttgt gggtcaattc aacaagatca agttgagacc taagtacaag | 480 |
| aagagcacca tccagtcatg cgctacactg gaacaaacca tcaaccacaa cactaacatc | 540 |
| tgtacagtgg cttccaccca ggagatcact cactacttca caaacgactt cgcccccctac | 600 |
| ctgatgaggt tcgacgataa cgactacaac tcgaacagat tctccgatca catgtctgaa | 660 |
| accggt | 666 |

<210> SEQ ID NO 5
<211> LENGTH: 828
<212> TYPE: DNA
<213> ORGANISM: Autographa californica nucleopolyhedrovirus

<400> SEQUENCE: 5

| | |
|---|---|
| atgatccgta catccagcca cgtcctgaac gtccaagaaa acatcatgac ttccaactgt | 60 |
| gcttccagcc cctactcctg tgaggccact tcagcctgcg ctgaggccca gcaactgcag | 120 |
| gtggacacag gtggcgataa gatcgtgaac aaccaggtca ccatgactca aatcaacttc | 180 |
| aacgcttcct acacctctgc cagcactccc tctcgtgcta gcttcgacaa ctcatactcg | 240 |
| gagttctgcg acaagcaacc taacgattac ttgtcttact acaaccaccc aaccccggac | 300 |
| ggagctgata ctgtcatctc cgactctgaa accgctgccg ctagcaactt cctcgcctca | 360 |
| gttaactcgc tcactgacaa cgatttggtg gagtgtctgc tcaagaccac tgacaacctg | 420 |
| gaggaagctg tgtcctctgc ctactacagc gagtcactcg aacagccagt ggtcgaacaa | 480 |
| ccctctccta gctcagctta ccacgccgag tccttcgaac actctgctgg tgtcaaccag | 540 |
| ccgtcggcca caggcaccaa gaggaagttg gacgagtacc tggataactc ccagggagtt | 600 |
| gtgggtcaat tcaacaagat caagttgaga cctaagtaca agaagagcac catccagtca | 660 |
| tgcgctacac tggaacaaac catcaaccac aacactaaca tctgtacagt ggcttccacc | 720 |
| caggagatca ctcactactt cacaaacgac ttcgcccccct acctgatgag gttcgacgat | 780 |

```
aacgactaca actcgaacag attctccgat cacatgtctg aaaccggt                    828
```

<210> SEQ ID NO 6
<211> LENGTH: 582
<212> TYPE: PRT
<213> ORGANISM: Autographa californica nucleopolyhedrovirus

<400> SEQUENCE: 6

```
Met Thr Gln Ile Asn Phe Asn Ala Ser Tyr Thr Ser Ala Ser Thr Pro
 1               5                  10                  15

Ser Arg Ala Ser Phe Asp Asn Ser Tyr Ser Glu Phe Cys Asp Lys Gln
            20                  25                  30

Pro Asn Asp Tyr Leu Ser Tyr Tyr Asn His Pro Thr Pro Asp Gly Ala
        35                  40                  45

Asp Thr Val Ile Ser Asp Ser Glu Thr Ala Ala Ala Ser Asn Phe Leu
    50                  55                  60

Ala Ser Val Asn Ser Leu Thr Asp Asn Asp Leu Val Glu Cys Leu Leu
65                  70                  75                  80

Lys Thr Thr Asp Asn Leu Glu Glu Ala Val Ser Ser Ala Tyr Tyr Ser
                85                  90                  95

Glu Ser Leu Glu Gln Pro Val Val Glu Gln Pro Ser Pro Ser Ser Ala
            100                 105                 110

Tyr His Ala Glu Ser Phe Glu His Ser Ala Gly Val Asn Gln Pro Ser
        115                 120                 125

Ala Thr Gly Thr Lys Arg Lys Leu Asp Glu Tyr Leu Asp Asn Ser Gln
    130                 135                 140

Gly Val Val Gly Gln Phe Asn Lys Ile Lys Leu Arg Pro Lys Tyr Lys
145                 150                 155                 160

Lys Ser Thr Ile Gln Ser Cys Ala Thr Leu Glu Gln Thr Ile Asn His
                165                 170                 175

Asn Thr Asn Ile Cys Thr Val Ala Ser Thr Gln Glu Ile Thr His Tyr
            180                 185                 190

Phe Thr Asn Asp Phe Ala Pro Tyr Leu Met Arg Phe Asp Asp Asn Asp
        195                 200                 205

Tyr Asn Ser Asn Arg Phe Ser Asp His Met Ser Glu Thr Gly Tyr Tyr
    210                 215                 220

Met Phe Val Val Lys Lys Ser Glu Val Lys Pro Phe Glu Ile Ile Phe
225                 230                 235                 240

Ala Lys Tyr Val Ser Asn Val Val Tyr Glu Tyr Thr Asn Asn Tyr Tyr
                245                 250                 255

Met Val Asp Asn Arg Val Phe Val Val Thr Phe Asp Lys Ile Arg Phe
            260                 265                 270

Met Ile Ser Tyr Asn Leu Val Lys Glu Thr Gly Ile Glu Ile Pro His
        275                 280                 285

Ser Gln Asp Val Cys Asn Asp Glu Thr Ala Ala Gln Asn Cys Lys Lys
    290                 295                 300

Cys His Phe Val Asp Val His His Thr Phe Lys Ala Ala Leu Thr Ser
305                 310                 315                 320

Tyr Phe Asn Leu Asp Met Tyr Tyr Ala Gln Thr Thr Phe Val Thr Leu
                325                 330                 335

Leu Gln Ser Leu Gly Glu Arg Lys Cys Gly Phe Leu Leu Ser Lys Leu
            340                 345                 350

Tyr Glu Met Tyr Gln Asp Lys Asn Leu Phe Thr Leu Pro Ile Met Leu
        355                 360                 365
```

```
Ser Arg Lys Glu Ser Asn Glu Ile Glu Thr Ala Ser Asn Asn Phe Phe
        370                 375                 380

Val Ser Pro Tyr Val Ser Gln Ile Leu Lys Tyr Ser Glu Ser Val Gln
385                 390                 395                 400

Phe Pro Asp Asn Pro Asn Lys Tyr Val Asp Asn Leu Asn Leu
                405                 410                 415

Ile Val Asn Lys Lys Ser Thr Leu Thr Tyr Lys Tyr Ser Ser Val Ala
                420                 425                 430

Asn Leu Leu Phe Asn Asn Tyr Lys Tyr His Asp Asn Ile Ala Ser Asn
        435                 440                 445

Asn Asn Ala Glu Asn Leu Lys Lys Val Lys Lys Glu Asp Gly Ser Met
450                 455                 460

His Ile Val Glu Gln Tyr Leu Thr Gln Asn Val Asp Asn Val Lys Gly
465                 470                 475                 480

His Asn Phe Ile Val Leu Ser Phe Lys Asn Glu Glu Arg Leu Thr Ile
                485                 490                 495

Ala Lys Lys Asn Lys Glu Phe Tyr Trp Ile Ser Gly Glu Ile Lys Asp
                500                 505                 510

Val Asp Val Ser Gln Val Ile Gln Lys Tyr Asn Arg Phe Lys His His
        515                 520                 525

Met Phe Val Ile Gly Lys Val Asn Arg Arg Glu Ser Thr Thr Leu His
        530                 535                 540

Asn Asn Leu Leu Lys Leu Leu Ala Leu Ile Leu Gln Gly Leu Val Pro
545                 550                 555                 560

Leu Ser Asp Ala Ile Thr Phe Ala Glu Gln Lys Leu Asn Cys Lys Tyr
                565                 570                 575

Lys Lys Phe Glu Phe Asn
                580

<210> SEQ ID NO 7
<211> LENGTH: 636
<212> TYPE: PRT
<213> ORGANISM: Autographa californica nucleopolyhedrovirus

<400> SEQUENCE: 7

Met Ile Arg Thr Ser Ser His Val Leu Asn Val Gln Glu Asn Ile Met
1               5                   10                  15

Thr Ser Asn Cys Ala Ser Ser Pro Tyr Ser Cys Glu Ala Thr Ser Ala
                20                  25                  30

Cys Ala Glu Ala Gln Gln Leu Gln Val Asp Thr Gly Gly Asp Lys Ile
            35                  40                  45

Val Asn Asn Gln Val Thr Met Thr Gln Ile Asn Phe Asn Ala Ser Tyr
50                  55                  60

Thr Ser Ala Ser Thr Pro Ser Arg Ala Ser Phe Asp Asn Ser Tyr Ser
65                  70                  75                  80

Glu Phe Cys Asp Lys Gln Pro Asn Asp Tyr Leu Ser Tyr Tyr Asn His
                85                  90                  95

Pro Thr Pro Asp Gly Ala Asp Thr Val Ile Ser Asp Ser Glu Thr Ala
            100                 105                 110

Ala Ala Ser Asn Phe Leu Ala Ser Val Asn Ser Leu Thr Asp Asn Asp
                115                 120                 125

Leu Val Glu Cys Leu Leu Lys Thr Thr Asp Asn Leu Glu Glu Ala Val
        130                 135                 140

Ser Ser Ala Tyr Tyr Ser Glu Ser Leu Glu Gln Pro Val Val Glu Gln
```

```
                145                 150                 155                 160
        Pro Ser Pro Ser Ser Ala Tyr His Ala Glu Ser Phe Glu His Ser Ala
                        165                 170                 175
        Gly Val Asn Gln Pro Ser Ala Thr Gly Thr Lys Arg Lys Leu Asp Glu
                        180                 185                 190
        Tyr Leu Asp Asn Ser Gln Gly Val Val Gly Gln Phe Asn Lys Ile Lys
                        195                 200                 205
        Leu Arg Pro Lys Tyr Lys Lys Ser Thr Ile Gln Ser Cys Ala Thr Leu
                        210                 215                 220
        Glu Gln Thr Ile Asn His Asn Thr Asn Ile Cys Thr Val Ala Ser Thr
        225                 230                 235                 240
        Gln Glu Ile Thr His Tyr Phe Thr Asn Asp Phe Ala Pro Tyr Leu Met
                        245                 250                 255
        Arg Phe Asp Asp Asn Asp Tyr Asn Ser Asn Arg Phe Ser Asp His Met
                        260                 265                 270
        Ser Glu Thr Gly Tyr Tyr Met Phe Val Val Lys Lys Ser Glu Val Lys
                        275                 280                 285
        Pro Phe Glu Ile Ile Phe Ala Lys Tyr Val Ser Asn Val Val Tyr Glu
                        290                 295                 300
        Tyr Thr Asn Asn Tyr Tyr Met Val Asp Asn Arg Val Phe Val Val Thr
        305                 310                 315                 320
        Phe Asp Lys Ile Arg Phe Met Ile Ser Tyr Asn Leu Val Lys Glu Thr
                        325                 330                 335
        Gly Ile Glu Ile Pro His Ser Gln Asp Val Cys Asn Asp Glu Thr Ala
                        340                 345                 350
        Ala Gln Asn Cys Lys Lys Cys His Phe Val Asp Val His His Thr Phe
                        355                 360                 365
        Lys Ala Ala Leu Thr Ser Tyr Phe Asn Leu Asp Met Tyr Tyr Ala Gln
                        370                 375                 380
        Thr Thr Phe Val Thr Leu Leu Gln Ser Leu Gly Glu Arg Lys Cys Gly
        385                 390                 395                 400
        Phe Leu Leu Ser Lys Leu Tyr Glu Met Tyr Gln Asp Lys Asn Leu Phe
                        405                 410                 415
        Thr Leu Pro Ile Met Leu Ser Arg Lys Glu Ser Asn Glu Ile Glu Thr
                        420                 425                 430
        Ala Ser Asn Asn Phe Phe Val Ser Pro Tyr Val Ser Gln Ile Leu Lys
                        435                 440                 445
        Tyr Ser Glu Ser Val Gln Phe Pro Asp Asn Pro Asn Lys Tyr Val
                        450                 455                 460
        Val Asp Asn Leu Asn Leu Ile Val Asn Lys Lys Ser Thr Leu Thr Tyr
        465                 470                 475                 480
        Lys Tyr Ser Ser Val Ala Asn Leu Leu Phe Asn Tyr Lys Tyr His
                        485                 490                 495
        Asp Asn Ile Ala Ser Asn Asn Ala Glu Asn Leu Lys Lys Val Lys
                        500                 505                 510
        Lys Glu Asp Gly Ser Met His Ile Val Glu Gln Tyr Leu Thr Gln Asn
                        515                 520                 525
        Val Asp Asn Val Lys Gly His Asn Phe Ile Val Leu Ser Phe Lys Asn
                        530                 535                 540
        Glu Glu Arg Leu Thr Ile Ala Lys Lys Asn Lys Glu Phe Tyr Trp Ile
        545                 550                 555                 560
        Ser Gly Glu Ile Lys Asp Val Asp Val Ser Gln Val Ile Gln Lys Tyr
                        565                 570                 575
```

```
Asn Arg Phe Lys His His Met Phe Val Ile Gly Lys Val Asn Arg Arg
            580                 585                 590

Glu Ser Thr Thr Leu His Asn Leu Leu Lys Leu Leu Ala Leu Ile
            595                 600                 605

Leu Gln Gly Leu Val Pro Leu Ser Asp Ala Ile Thr Phe Ala Glu Gln
            610                 615                 620

Lys Leu Asn Cys Lys Tyr Lys Lys Phe Glu Phe Asn
625                 630                 635

<210> SEQ ID NO 8
<211> LENGTH: 222
<212> TYPE: PRT
<213> ORGANISM: Autographa californica nucleopolyhedrovirus

<400> SEQUENCE: 8

Met Thr Gln Ile Asn Phe Asn Ala Ser Tyr Thr Ser Ala Ser Thr Pro
1               5                   10                  15

Ser Arg Ala Ser Phe Asp Asn Ser Tyr Ser Glu Phe Cys Asp Lys Gln
            20                  25                  30

Pro Asn Asp Tyr Leu Ser Tyr Tyr Asn His Pro Thr Pro Asp Gly Ala
            35                  40                  45

Asp Thr Val Ile Ser Asp Ser Glu Thr Ala Ala Ala Ser Asn Phe Leu
50                  55                  60

Ala Ser Val Asn Ser Leu Thr Asp Asn Asp Leu Val Glu Cys Leu Leu
65                  70                  75                  80

Lys Thr Thr Asp Asn Leu Glu Glu Ala Val Ser Ser Ala Tyr Tyr Ser
            85                  90                  95

Glu Ser Leu Glu Gln Pro Val Val Gln Pro Ser Pro Ser Ser Ala
            100                 105                 110

Tyr His Ala Glu Ser Phe Glu His Ser Ala Gly Val Asn Gln Pro Ser
            115                 120                 125

Ala Thr Gly Thr Lys Arg Lys Leu Asp Glu Tyr Leu Asp Asn Ser Gln
            130                 135                 140

Gly Val Val Gly Gln Phe Asn Lys Ile Lys Leu Arg Pro Lys Tyr Lys
145                 150                 155                 160

Lys Ser Thr Ile Gln Ser Cys Ala Thr Leu Glu Gln Thr Ile Asn His
            165                 170                 175

Asn Thr Asn Ile Cys Thr Val Ala Ser Thr Gln Glu Ile Thr His Tyr
            180                 185                 190

Phe Thr Asn Asp Phe Ala Pro Tyr Leu Met Arg Phe Asp Asp Asn Asp
            195                 200                 205

Tyr Asn Ser Asn Arg Phe Ser Asp His Met Ser Glu Thr Gly
    210                 215                 220

<210> SEQ ID NO 9
<211> LENGTH: 276
<212> TYPE: PRT
<213> ORGANISM: Autographa californica nucleopolyhedrovirus

<400> SEQUENCE: 9

Met Ile Arg Thr Ser Ser His Val Leu Asn Val Gln Glu Asn Ile Met
1               5                   10                  15

Thr Ser Asn Cys Ala Ser Ser P

Val Asn Asn Gln Val Thr Met Thr Gln Ile Asn Phe Asn Ala Ser Tyr
        50                  55                  60

Thr Ser Ala Ser Thr Pro Ser Arg Ala Ser Phe Asp Asn Ser Tyr Ser
 65                  70                  75                  80

Glu Phe Cys Asp Lys Gln Pro Asn Asp Tyr Leu Ser Tyr Tyr Asn His
                 85                  90                  95

Pro Thr Pro Asp Gly Ala Asp Thr Val Ile Ser Asp Ser Glu Thr Ala
                100                 105                 110

Ala Ala Ser Asn Phe Leu Ala Ser Val Asn Ser Leu Thr Asp Asn Asp
            115                 120                 125

Leu Val Glu Cys Leu Leu Lys Thr Thr Asp Asn Leu Glu Glu Ala Val
130                 135                 140

Ser Ser Ala Tyr Tyr Ser Glu Ser Leu Glu Gln Pro Val Val Glu Gln
145                 150                 155                 160

Pro Ser Pro Ser Ser Ala Tyr His Ala Glu Ser Phe Glu His Ser Ala
                165                 170                 175

Gly Val Asn Gln Pro Ser Ala Thr Gly Thr Lys Arg Lys Leu Asp Glu
                180                 185                 190

Tyr Leu Asp Asn Ser Gln Gly Val Val Gly Phe Asn Lys Ile Lys
            195                 200                 205

Leu Arg Pro Lys Tyr Lys Lys Ser Thr Ile Gln Ser Cys Ala Thr Leu
210                 215                 220

Glu Gln Thr Ile Asn His Asn Thr Asn Ile Cys Thr Val Ala Ser Thr
225                 230                 235                 240

Gln Glu Ile Thr His Tyr Phe Thr Asn Asp Phe Ala Pro Tyr Leu Met
            245                 250                 255

Arg Phe Asp Asp Asn Asp Tyr Asn Ser Asn Arg Phe Ser Asp His Met
                260                 265                 270

Ser Glu Thr Gly
        275

<210> SEQ ID NO 10
<211> LENGTH: 128
<212> TYPE: DNA
<213> ORGANISM: Autographa californica nucleopolyhedrovirus

<400> SEQUENCE: 10
atcatggaga taattaaaat gataaccatc tcgcaaataa ataagtattt tactgttttc      60
gtaacagttt tgtaataaaa aaacctataa atattccgga ttattcatac cgtcccacca     120
tcgggcgc                                                             128

<210> SEQ ID NO 11
<211> LENGTH: 122
<212> TYPE: DNA
<213> ORGANISM: Autographa californica nucleopolyhedrovirus

<400> SEQUENCE: 11
atacggacct taattcaac ccaacacaat atattatagt taaataagaa ttattatcaa      60
atcatttgta tattaattaa aatactatac tgtaaattac attttattta caatcactcg     120
ac                                                                   122

<210> SEQ ID NO 12
<211> LENGTH: 571
<212> TYPE: DNA
<213> ORGANISM: Artificial Sequence
<220> FEATURE:
<223> OTHER INFORMATION: Recombinant chimeric promoter

<400> SEQUENCE: 12

```
aaaaacatcg attagggtga ctgaaggtta cattggggta ggttatggtt aatacgtaat      60
ggtttaacac caaaacgata tcatggattt tatataaggt gtaataatat ttttaatgag     120
tggacgcgtc gggtcaatgt cctgcctatt gacgtcataa catattaggt gattatatta    180
aaaatagttt aaactcaaat attacttgca agtttaagtt tcatcataat ctgatcataa    240
gtttcaccca aacagaaacc aaaagcataa ctatcgaata tctttagctt cccatgaaga    300
aagattaccg taaccatcac taggatttta tacgattgta gaaaataaag tattctcagt    360
ctcttttcag agcgctataa aaaggggtgc attctcggta agagtacagt tgaactcaca    420
tcgagttaac tccacgctgc agtctcgaga tacggacctt taattcaacc caacacaata    480
tattatagtt aaataagaat tattatcaaa tcatttgtat attaattaaa atactatact    540
gtaaattaca ttttatttac aatcactcga c                                   571
```

<210> SEQ ID NO 13
<211> LENGTH: 465
<212> TYPE: DNA
<213> ORGANISM: Artificial Sequence
<220> FEATURE:
<223> OTHER INFORMATION: Recombinant chimeric promoter

<400> SEQUENCE: 13

```
ggtaccaaat tccgttttgc gacgatgcag agtttttgaa caggctgctc aaacacatag     60
atccgtaccc gctcagtcgg atgtattaca atgcagccaa taccatgttt tacacgacta    120
tggaaaacta tgccgtgtcc aattgcaagt tcaacattga ggattacaat aacatattta    180
aggtgatgga aaatattagg aaacacagca acaaaaattc aaacgaccaa gacgagttaa    240
acatatattt gggagttcag tcgtcgaatg caaagcgtaa aaaatattaa taaggtaaaa    300
attacagcta cataaattac acaatttaaa ctgcagtctg gagatacgga cctttaattc    360
aacccaacac aatatattat agttaaataa gaattattat caaatcattt gtatattaat    420
taaaatacta tactgtaaat tacattttat ttacaatcac tcgac                    465
```

<210> SEQ ID NO 14
<211> LENGTH: 436
<212> TYPE: DNA
<213> ORGANISM: Autographa californica nucleopolyhedrovirus

<400> SEQUENCE: 14

```
aaaaacatcg attagggtga ctgaaggtta cattggggta ggttatggtt aatacgtaat     60
ggtttaacac caaaacgata tcatggattt tatataaggt gtaataatat ttttaatgag    120
tggacgcgtc gggtcaatgt cctgcctatt gacgtcataa catattaggt gattatatta    180
aaaatagttt aaactcaaat attacttgca agtttaagtt tcatcataat ctgatcataa    240
gtttcaccca aacagaaacc aaaagcataa ctatcgaata tctttagctt cccatgaaga    300
aagattaccg taaccatcac taggatttta tacgattgta gaaaataaag tattctcagt    360
ctcttttcag agcgctataa aaaggggtgc attctcggta agagtacagt tgaactcaca    420
tcgagttaac tccacg                                                    436
```

<210> SEQ ID NO 15
<211> LENGTH: 1199
<212> TYPE: DNA

<213> ORGANISM: Artificial Sequence
<220> FEATURE:
<223> OTHER INFORMATION: Recombinant chimeric promoter

<400> SEQUENCE: 15

```
cttgaatgtt agtgaaaccc cctgcgacac aagtattaca ttccttagtg cttgaatcct      60
ttaggaaaga aaagccaatt ttcaaaatct tagcacttgt taactcgcga aaaagaccaa     120
cagatttccc atactacaat tcgacattag aaatgtaaac ccattatcat tatttacgcc     180
tcatttccat ccaataataa gtttaagtac gttgagataa aactggctta cctagaactt     240
gacatggcga cctcttgcac tctgtatctc aagtcaactt tctctatcca aatatttgat     300
aacatttgac atgatattga agtaagattg ttactaaggc ttacattgta atattactga     360
cgcaagttct ttatcaataa aatagctgaa acaaaaaaaa aaaacatcga ttagggtgac     420
tgaaggttac attggggtag gttatggtta atacgtaatg gtttaacacc aaaacgatat     480
catggattga ctttataaat tttatataag gtgtaataat attttaatg agtggacgcg       540
tcgggtcaat gtcctgccta ttgacgtcat aacatattag gtgattatat taaaaatact     600
caaatattac ttgcaagttt aagtttcatc ataatctgat cataagtttc acccaaacag     660
aaaccaaaag cataactatc tgctatttga atatcttag cttcccatga agaaagatta      720
ccgtaaccat cactaggatt ttatacgatt gtagaaaata agtattctc agtctctttt      780
cagtttaaaa tctgctggca tttttacaag tcgctgtatc agtcaatgtt tatacaatat     840
gtcaatgtac tttcgtatta atcagaaaaa aatattctac tagttttgat aagctatcac     900
ttttgttaca ttgtactgcc ctttacagtt catcaggtat ttatgaatga catattggag     960
aaacatcgta atcagtccag tataaaaagg ggtgcattct cggtaagagt acagttgaac    1020
tcacatcgag ttaactccac gaatcactag tgaattcgcg gccgctgcag tctcgagata    1080
cggacccttta attcaaccca acacaatata ttatagttaa ataagaatta ttatcaaatc    1140
atttgtatat taattaaaat actatactgt aaattacatt ttatttacaa tcactcgac    1199
```

<210> SEQ ID NO 16
<211> LENGTH: 250
<212> TYPE: DNA
<213> ORGANISM: Artificial Sequence
<220> FEATURE:
<223> OTHER INFORMATION: Recombinant chimeric promoter

<400> SEQUENCE: 16

```
atcatggaga taattaaaat gataaccatc tcgcaaataa ataagtattt tactgttttc      60
gtaacagttt tgtaataaaa aaacctataa atattccgga ttattcatac cgtcccacca     120
tcgggcgcat acggaccttt aattcaaccc aacacaatat attatagtta aataagaatt     180
attatcaaat catttgtata ttaattaaaa tactatactg taaattacat tttatttaca     240
atcactcgac                                                           250
```

<210> SEQ ID NO 17
<211> LENGTH: 3163
<212> TYPE: DNA
<213> ORGANISM: Artificial Sequence
<220> FEATURE:
<223> OTHER INFORMATION: Recombinant expression cassette

<400> SEQUENCE: 17

```
ttagttgaac tcgaacttct tgtacttgca gttgagcttt gctcggcga atgtgatggc      60
gtcggagagt ggcaccagtc cctgcaggat caaggccaag agcttcagca agttgttgtg    120
```

```
cagtgtagtt gactcgcgac ggttgacctt gccgatcacg aacatgtggt gcttgaatct    180
gttgtacttt tggatgacct ggctcacatc aacgtccttg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcagacgaa     600 gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg taggggcga agtcgtttgt gaagtagtga gtgatctcct gggtggaagc    1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg gttgttcgac   1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccggggt   1620
tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatt   1920
gggtcatcta gattcgaaag cggccgcgac tagtgagctc gtcgacgtag gcctttgaat   1980
tccgcgcgct tcggaccggg atccgcgccc gatggtggga cggtatgaat aatccggaat   2040
atttataggt tttttattca aaaactgtt acgaaaacag taaatactt atttatttgc     2100 gagatggtta tcattttaat tatctccatg atctattaat attccggagt atacatcgat   2160 gttgaccccca acaaaagatt tataattaat cataatcacg aacaacaaca agtcaatgaa   2220
acaaataaac aagttgtcga taaaacattc ataaatgaca cagcaacata caattcttgc   2280
ataataaaaa tttaaatgac atcatatttg agaataacaa atgacattat ccctcgattg   2340
tgttttacaa gtagaattct acccgtaaag cgagtttagt tttgaaaaac aaatgacatc   2400
atttgtataa tgacatcatc ccctgattgt gttttacaag tagaattcta tccgtaaagc   2460
```

| | |
|---|---:|
| gagttcagtt ttgaaaacaa atgagtcata cctaaacacg ttaataatct tctgatatca | 2520 |
| gcttatgact caagttatga gccgtgtgca aaacatgaga taagtttatg acatcatcca | 2580 |
| ctgatcgtgc gttacaagta gaattctact cgtaaagcca gttcggttat gagccgtgtg | 2640 |
| caaaacatga catcagctta tgactcatac ttgattgtgt tttacgcgta gaattctact | 2700 |
| cgtaaagcga gttcggttat gagccgtgtg caaaacatga catcagctta tgagtcataa | 2760 |
| ttaatcgtgc gttacaagta gaattctact cgtaaagcga gttgaaggat catatttagt | 2820 |
| tgcgtttatg agataagatt gaaagcacgt gtaaaatgtt tcccgcgcgt tggcacaact | 2880 |
| atttacaatg cggccaagtt ataaaagatt ctaatctgat atgttttaaa acacctttgc | 2940 |
| ggcccgagtt gtttgcgtac gtgactagcg aagaagatgt gtggaccgca gaacagatag | 3000 |
| taaaacaaaa ccctagtatt ggagcaataa tcgatgagct catacggacc tttaattcaa | 3060 |
| cccaacacaa tatattatag ttaaataaga attattatca aatcatttgt atattaatta | 3120 |
| aaatactata ctgtaaatta cattttattt acaatcactc gac | 3163 |

<210> SEQ ID NO 18
<211> LENGTH: 3656
<212> TYPE: DNA
<213> ORGANISM: Artificial Sequence
<220> FEATURE:
<223> OTHER INFORMATION: Recombinant expression cassette

<400> SEQUENCE: 18

| | |
|---|---:|
| ttagttgaac tcgaacttct tgtacttgca gttgagcttt tgctcggcga atgtgatggc | 60 |
| gtcggagagt ggcaccagtc cctgcaggat caaggccaag agcttcagca agttgttgtg | 120 |
| cagtgtagtt gactcgcgac ggttgacctt gccgatcacg aacatgtggt gcttgaatct | 180 |
| gttgtacttt tggatgacct ggctcacatc aacgtccttg atttcgccag agatccagta | 240 |
| gaactccttg ttcttcttag cgatggtcag cctttcctcg ttcttgaagg acaacacgat | 300 |
| gaagttgtga cccttaacgt tatcgacgtt ttgagtcaag tactgctcaa cgatgtgcat | 360 |
| gcttccgtct tccttcttga ccttcttgag gttctcggcg ttgttgttag aagcgatgtt | 420 |
| gtcgtggtac ttgtagttgt tgaagagcag gttagcgacg gacgagtact tgtatgtcag | 480 |
| agtgctcttc ttgttcacga tgaggttcag gttatcaacg acgtacttgt tgggagggtt | 540 |
| gtccgggaat tggacggact ccgagtactt gaggatctgg gaaacgtatg gcagacgaa | 600 |
| gaagttgtta gaggcggttt cgatctcgtt tgattccttg cggctcagca tgatgggcaa | 660 |
| agtgaagagg ttcttgtcct ggtacatctc gtacaacttc gacaagagga atccacactt | 720 |
| acgctcgccg agtgattgca gcaaggtcac gaaggttgtc tgagcgtagt acatatcgag | 780 |
| gttgaagtag gaggtcagag cggccttgaa tgtgtggtgg acgtccacga agtgacactt | 840 |
| cttgcagttt tgagcggcgg tctcatcgtt gcagacgtcc tgtgagtgtg ggatttcgat | 900 |
| gccagtctcc ttaaccaggt tgtagctgat catgaagcgg atcttatcga aggtcacaac | 960 |
| gaacacacgg ttgtcaacca tgtagtagtt gtttgtgtac tcgtagacca cgttagagac | 1020 |
| gtacttggcg aagatgattt cgaaaggctt cacctcggac ttcttaacga cgaacatgta | 1080 |
| gtaaccggtt tcagacatgt gatcggagaa tctgttcgag ttgtagtcgt tatcgtcgaa | 1140 |
| cctcatcagg taggggcga agtcgtttgt gaagtagtga gtgatctcct gggtggaagc | 1200 |
| cactgtacag atgttagtgt tgtggttgat ggtttgttcc agtgtagcgc atgactggat | 1260 |
| ggtgctcttc ttgtacttag gtctcaactt gatcttgttg aattgaccca caactccctg | 1320 |
| ggagttatcc aggtactcgt ccaacttcct cttggtgcct gtggccgacg gctggttgac | 1380 |

```
accagcagag tgttcgaagg actcggcgtg gtaagctgag ctaggagagg gttgttcgac  1440
cactggctgt tcgagtgact cgctgtagta ggcagaggac acagcttcct ccaggttgtc  1500
agtggtcttg agcagacact ccaccaaatc gttgtcagtg agcgagttaa ctgaggcgag  1560
gaagttgcta gcggcagcgg tttcagagtc ggagatgaca gtatcagctc cgtccggggt  1620
tgggtggttg tagtaagaca agtaatcgtt aggttgcttg tcgcagaact ccgagtatga  1680
gttgtcgaag ctagcacgag agggagtgct ggcagaggtg taggaagcgt tgaagttgat  1740
ttgagtcatg gtgacctggt tgttcacgat cttatcgcca cctgtgtcca cctgcagttg  1800
ctgggcctca gcgcaggctg aagtggcctc acaggagtag gggctggaag cacagttgga  1860
agtcatgatg ttttcttgga cgttcaggac gtggctggat gtacggatca tagatctatt  1920
gggtcatcta gattcgaaag cggccgcgac tagtgagctc gtcgacgtag gcctttgaat  1980
tccgcgcgct tcggaccggg atccgcgccc gatggtggga cggtatgaat aatccggaat  2040
atttataggt ttttttatta caaaactgtt acgaaaacag taaatactt atttatttgc  2100 gagatggtta tcatttttaat tatctccatg atctattaat attccggagt atacatcgat  2160 gttgaccccca acaaaagatt tataattaat cataatcacg aacaacaaca agtcaatgaa  2220
acaaataaac aagttgtcga taaaacattc ataaatgaca cagcaacata caattcttgc  2280
ataataaaaa tttaaatgac atcatatttg agaataacaa atgacattat ccctcgattg  2340
tgttttacaa gtagaattct acccgtaaag cgagtttagt tttgaaaaac aaatgacatc  2400
atttgtataa tgacatcatc ccctgattgt gttttacaag tagaattcta tccgtaaagc  2460
gagttcagtt ttgaaaacaa atgagtcata cctaaacacg ttaataatct tctgatatca  2520
gcttatgact caagttatga gccgtgtgca aaacatgaga taagtttatg acatcatcca  2580
ctgatcgtgc gttacaagta gaattctact cgtaaagcca gttcggttat gagccgtgtg  2640
caaaacatga catcagctta tgactcatac ttgattgtgt tttacgcgta gaattctact  2700
cgtaaagcga gttcggttat gagccgtgtg caaaacatga catcagctta tgagtcataa  2760
ttaatcgtgc gttacaagta gaattctact cgtaaagcga gttgaaggat catatttagt  2820
tgcgtttatg agataagatt gaaagcacgt gtaaaatgtt tcccgcgcgt tggcacaact  2880
atttacaatg cggccaagtt ataaaagatt ctaatctgat atgttttaaa acacctttgc  2940
ggcccgagtt gtttgcgtac gtgactagcg aagaagatgt gtggaccgca gaacagatag  3000
taaaacaaaa ccctagtatt ggagcaataa tcgatgagct cgtcgacgta ggcctttgaa  3060
ttccgcgcgc ttcggaccgg gatccaaaaa catcgattag ggtgactgaa ggttacattg  3120
gggtaggtta tggttaatac gtaatggttt aacaccaaaa cgatatcatg gattttatat  3180
aaggtgtaat aatatttttta atgagtggac gcgtcgggtc aatgtcctgc ctattgacgt  3240
cataacatat taggtgatta tattaaaaat agtttaaact caaatattac ttgcaagttt  3300
aagtttcatc ataatctgat cataagtttc acccaaacag aaaccaaaag cataactatc  3360
gaatatcttt agcttcccat gaagaaagat taccgtaacc atcactagga ttttatacga  3420
ttgtagaaaa taaagtattc tcagtctctt ttcagagcgc tataaaaagg ggtgcattct  3480
cggtaagagt acagttgaac tcacatcgag ttaactccac gctgcagtct cgagatacgg  3540
acctttaatt caacccaaca caatatatta tagttaaata agaattatta tcaaatcatt  3600
tgtatattaa ttaaaatact atactgtaaa ttacatttta tttacaatca ctcgac       3656
```

<210> SEQ ID NO 19

<211> LENGTH: 3541
<212> TYPE: DNA
<213> ORGANISM: Artificial Sequence
<220> FEATURE:
<223> OTHER INFORMATION: Recombinant expression cassette

<400> SEQUENCE: 19

| | |
|---|---|
| ttagttgaac tcgaacttct tgtacttgca gttgagcttt tgctcggcga atgtgatggc | 60 |
| gtcggagagt ggcaccagtc cctgcaggat caaggccaag agcttcagca agttgttgtg | 120 |
| cagtgtagtt gactcgcgac ggttgacctt gccgatcacg aacatgtggt gcttgaatct | 180 |
| gttgtacttt tggatgacct ggctcacatc aacgtccttg atttcgccag agatccagta | 240 |
| gaactccttg ttcttcttag cgatggtcag cctttcctcg ttcttgaagg acaacacgat | 300 |
| gaagttgtga cccttaacgt tatcgacgtt ttgagtcaag tactgctcaa cgatgtgcat | 360 |
| gcttccgtct tccttcttga ccttcttgag gttctcggcg ttgttgttag aagcgatgtt | 420 |
| gtcgtggtac ttgtagttgt tgaagagcag gttagcgacg gacgagtact tgtatgtcag | 480 |
| agtgctcttc ttgttcacga tgaggttcag gttatcaacg acgtacttgt tgggagggtt | 540 |
| gtccgggaat tggacggact ccgagtactt gaggatctgg gaaacgtatg gcgagacgaa | 600 |
| gaagttgtta gaggcggttt cgatctcgtt tgattccttg cggctcagca tgatgggcaa | 660 |
| agtgaagagg ttcttgtcct ggtacatctc gtacaacttc gacaagagga atccacactt | 720 |
| acgctcgccg agtgattgca gcaaggtcac gaaggttgtc tgagcgtagt acatatcgag | 780 |
| gttgaagtag gaggtcagag cggccttgaa tgtgtggtgg acgtccacga agtgacactt | 840 |
| cttgcagttt tgagcggcgg tctcatcgtt gcagacgtcc tgtgagtgtg ggatttcgat | 900 |
| gccagtctcc ttaaccaggt tgtagctgat catgaagcgg atcttatcga aggtcacaac | 960 |
| gaacacacgg ttgtcaacca tgtagtagtt gtttgtgtac tcgtagacca cgttagagac | 1020 |
| gtacttggcg aagatgattt cgaaaggctt cacctcggac ttcttaacga cgaacatgta | 1080 |
| gtaaccggtt tcagacatgt gatcggagaa tctgttcgag ttgtagtcgt tatcgtcgaa | 1140 |
| cctcatcagg taggggcga agtcgtttgt gaagtagtga gtgatctcct gggtggaagc | 1200 |
| cactgtacag atgttagtgt tgtggttgat ggtttgttcc agtgtagcgc atgactggat | 1260 |
| ggtgctcttc ttgtacttag gtctcaactt gatcttgttg aattgaccca caactccctg | 1320 |
| ggagttatcc aggtactcgt ccaacttcct cttggtgcct gtggccgacg gctggttgac | 1380 |
| accagcagag tgttcgaagg actcggcgtg gtaagctgag ctaggagagg gttgttcgac | 1440 |
| cactggctgt tcgagtgact cgctgtagta ggcagaggac acagcttcct ccaggttgtc | 1500 |
| agtggtcttg agcagacact ccaccaaatc gttgtcagtg agcgagttaa ctgaggcgag | 1560 |
| gaagttgcta gcggcagcgg tttcagagtc ggagatgaca gtatcagctc cgtccgggt | 1620 |
| tgggtggttg tagtaagaca agtaatcgtt aggttgcttg tcgcagaact ccgagtatga | 1680 |
| gttgtcgaag ctagcacgag agggagtgct ggcagaggtg taggaagcgt tgaagttgat | 1740 |
| ttgagtcatg gtgacctggt tgttcacgat cttatcgcca cctgtgtcca cctgcagttg | 1800 |
| ctgggcctca gcgcaggctg aagtggcctc acaggagtag gggctggaag cacagttgga | 1860 |
| agtcatgatg ttttcttgga cgttcaggac gtggctggat gtacggatca tagatctatc | 1920 |
| tagattcgaa agcggccgcg actagtgagc tcgtcgacgt aggcctttga attccgcgcg | 1980 |
| cttcggaccg ggatccgcgc ccgatggtgg gacggtatga ataatccgga atatttatag | 2040 |
| gtttttttat tacaaaactg ttacgaaaac agtaaaatac ttatttatttt gcagatggt | 2100 |
| tatcatttta attatctcca tgatctatta atattccgga gtatacatcg atgttgaccc | 2160 |

```
caacaaaaga tttataatta atcataatca cgaacaacaa caagtcaatg aaacaaataa    2220
acaagttgtc gataaaacat tcataaatga cacagcaaca tacaattctt gcataataaa    2280
aatttaaatg acatcatatt tgagaataac aaatgacatt atccctcgat tgtgttttac    2340
aagtagaatt ctacccgtaa agcgagttta gttttgaaaa acaaatgaca tcatttgtat    2400
aatgacatca tccctgatt gtgttttaca agtagaattc tatccgtaaa gcgagttcag    2460
ttttgaaaac aaatgagtca tacctaaaca cgttaataat cttctgatat cagcttatga    2520
ctcaagttat gagccgtgtg caaaacatga gataagttta tgacatcatc cactgatcgt    2580
gcgttacaag tagaattcta ctcgtaaagc cagttcggtt atgagccgtg tgcaaaacat    2640
gacatcagct tatgactcat acttgattgt gttttacgcg tagaattcta ctcgtaaagc    2700
gagttcggtt atgagccgtg tgcaaaacat gacatcagct tatgagtcat aattaatcgt    2760
gcgttacaag tagaattcta ctcgtaaagc gagttgaagg atcatattta gttgcgttta    2820
tgagataaga ttgaaagcac gtgtaaaatg tttcccgcgc gttggcacaa ctatttacaa    2880
tgcggccaag ttataaaaga ttctaatctg atatgtttta aaacaccttt gcggcccgag    2940
ttgtttgcgt acgtgactag cgaagaagat gtgtggaccg cagaacagat agtaaaacaa    3000
aaccctagta ttggagcaat aatcgatgag ctcgtcgacg taggcctttg aattccgcgc    3060
gcttcggacc gggatcggta ccaaattccg ttttgcgacg atgcagagtt tttgaacagg    3120
ctgctcaaac acatagatcc gtacccgctc agtcggatgt attacaatgc agccaatacc    3180
atgttttaca cgactatgga aaactatgcc gtgtccaatt gcaagttcaa cattgaggat    3240
tacaataaca tatttaaggt gatggaaaat attaggaaac acagcaacaa aaattcaaac    3300
gaccaagacg agttaaacat atatttggga gttcagtcgt cgaatgcaaa gcgtaaaaaa    3360
tattaataag gtaaaaatta cagctacata aattacacaa tttaaactgc agtctggaga    3420
tacggacctt taattcaacc caacacaata tattatagtt aaataagaat tattatcaaa    3480
tcatttgtat attaattaaa atactatact gtaaattaca ttttatttac aatcactcga    3540
c                                                                   3541

<210> SEQ ID NO 20
<211> LENGTH: 3512
<212> TYPE: DNA
<213> ORGANISM: Artificial Sequence
<220> FEATURE:
<223> OTHER INFORMATION: Recombinant expression cassette

<400> SEQUENCE: 20
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg acgagtact  tgtatgtcag     480 agtgctcttc ttgttcacga tgaggttcag gttatcaacg acgtacttgt tgggagggtt     540
gtccgggaat tggacggact ccgagtactt gaggatctgg gaaacgtatg gcgagacgaa     600
```

```
gaagttgtta gaggcggttt cgatctcgtt tgattccttg cggctcagca tgatgggcaa      660
agtgaagagg ttcttgtcct ggtacatctc gtacaacttc gacaagagga atccacactt      720
acgctcgccg agtgattgca gcaaggtcac gaaggttgtc tgagcgtagt acatatcgag      780
gttgaagtag gaggtcagag cggccttgaa tgtgtggtgg acgtccacga agtgacactt      840
cttgcagttt tgagcggcgg tctcatcgtt gcagacgtcc tgtgagtgtg ggatttcgat      900
gccagtctcc ttaaccaggt tgtagctgat catgaagcgg atcttatcga aggtcacaac      960
gaacacacgg ttgtcaacca tgtagtagtt gtttgtgtac tcgtagacca cgttagagac     1020
gtacttggcg aagatgattt cgaaaggctt cacctcggac ttcttaacga cgaacatgta     1080
gtaaccggtt tcagacatgt gatcggagaa tctgttcgag ttgtagtcgt tatcgtcgaa     1140
cctcatcagg taggggcga agtcgtttgt gaagtagtga gtgatctcct gggtggaagc     1200
cactgtacag atgttagtgt tgtggttgat ggtttgttcc agtgtagcgc atgactggat     1260
ggtgctcttc ttgtacttag gtctcaactt gatcttgttg aattgaccca caactccctg     1320
ggagttatcc aggtactcgt ccaacttcct cttggtgcct gtggccgacg gctggttgac     1380
accagcagag tgttcgaagg actcggcgtg gtaagctgag ctaggagagg gttgttcgac     1440
cactggctgt tcgagtgact cgctgtagta ggcagaggac acagcttcct ccaggttgtc     1500
agtggtcttg agcagacact ccaccaaatc gttgtcagtg agcgagttaa ctgaggcgag     1560
gaagttgcta gcgcagcgg tttcagagtc ggagatgaca gtatcagctc cgtccggggt      1620
tgggtggttg tagtaagaca agtaatcgtt aggttgcttg tcgcagaact ccgagtatga     1680
gttgtcgaag ctagcacgag agggagtgct ggcagaggtg taggaagcgt tgaagttgat     1740
ttgagtcatg gtgacctggt tgttcacgat cttatcgcca cctgtgtcca cctgcagttg     1800
ctgggcctca gcgcaggctg aagtggcctc acaggagtag gggctggaag cacagttgga     1860
agtcatgatg ttttcttgga cgttcaggac gtggctggat gtacggatca tagatctatc     1920
tagatgcatt cgcgaggtac cgagctcgaa ttcactggcc gtcgttttac aacgtcgtga     1980
ctgggaaaac cctggcgtta cccaacttaa tcgccttgca gcacatcccc ctttcgccag     2040
ctgctagcac catggctcga gcgtggagtt aactcgatgt gagttcaact gtactcttac     2100
cgagaatgca cccctttta tagcgctctg aaaagagact gagaatactt tattttctac      2160
aatcgtataa atcctagtg atggttacgg taatctttct tcatgggaag ctaaagatat      2220
tcgatagtta tgcttttggt ttctgtttgg gtgaaactta tgatcagatt atgatgaaac     2280
ttaaacttgc aagtaatatt tgagtttaaa ctatttttaa tataatcacc taatatgtta     2340
tgacgtcaat aggcaggaca ttgacccgac gcgtccactc attaaaaata ttattacacc     2400
ttatataaaa tccatgatat cgttttggtg ttaaaccatt acgtattaac cataacctac     2460
cccaatgtaa ccttcagtca ccctaatcga tgttttgta tacatcgatg ttgaccccaa      2520
caaaagattt ataattaatc ataatcacga acaacaacaa gtcaatgaaa caaataaaca     2580
agttgtcgat aaaacattca taatgacac agcaacatac aattcttgca taataaaaat      2640
ttaaatgaca tcatatttga gaataacaaa tgacattatc cctcgattgt gttttacaag     2700
tagaattcta cccgtaaagc gagtttagtt ttgaaaaaca aatgacatca tttgtataat     2760
gacatcatcc cctgattgtg ttttacaagt agaattctat ccgtaaagcg agttcagttt     2820
tgaaaacaaa tgagtcatac ctaaacacgt taataatctt ctgatatcag cttatgactc     2880
aagttatgag ccgtgtgcaa aacatgagat aagtttatga catcatccac tgatcgtgcg     2940
ttacaagtag aattctactc gtaaagccag ttcggttatg agccgtgtgc aaaacatgac     3000
```

```
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaaatgttt cccgcgcgtt ggcacaacta tttacaatgc    3240
ggccaagtta taaaagattc taatctgata tgttttaaaa cacctttgcg gcccgagttg    3300
tttgcgtacg tgactagcga agaagatgtg tggaccgcag aacagatagt aaaacaaaac    3360
cctagtattg gagcaataat cgatgagctc atacggacct taattcaac ccaacacaat     3420 atattatagt taaataagaa ttattatcaa atcatttgta tattaattaa aatactatac    3480
tgtaaattac attttattta caatcactcg ac                                  3512

<210> SEQ ID NO 21
<211> LENGTH: 4005
<212> TYPE: DNA
<213> ORGANISM: Artificial Sequence
<220> FEATURE:
<223> OTHER INFORMATION: Recombinant expression cassette

<400> SEQUENCE: 21
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg gacgagtact tgtatgtcag     480
agtgctcttc ttgttcacga tgaggttcag gttatcaacg acgtacttgt tgggagggtt     540
gtccgggaat tggacggact ccgagtactt gaggatctgg gaaacgtatg gcgagacgaa     600
gaagttgtta gaggcggttt cgatctcgtt tgattccttg cggctcagca tgatgggcaa     660
agtgaagagg ttcttgtcct ggtacatctc gtacaacttc gacaagagga atccacactt     720
acgctcgccg agtgattgca gcaaggtcac gaaggttgtc tgagcgtagt acatatcgag     780
gttgaagtag gaggtcagag cggccttgaa tgtgtggtgg acgtccacga agtgacactt     840
cttgcagttt tgagcggcgg tctcatcgtt gcagacgtcc tgtgagtgtg ggatttcgat     900
gccagtctcc ttaaccaggt tgtagctgat catgaagcgg atcttatcga aggtcacaac     960
gaacacacgt tgtcaaccat gtagtagtt gtttgtgtac tcgtagacca cgttagagac    1020
gtacttggcg aagatgattt cgaaaggctt cacctcggac ttcttaacga cgaacatgta    1080
gtaaccggtt tcagacatgt gatcggagaa tctgttcgag ttgtagtcgt tatcgtcgaa    1140
cctcatcagg tagggggcga agtcgtttgt gaagtagtga gtgatctcct gggtggaagc    1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg gctggttgac    1380
accagcagag tgttcgaagg actcggcgtg taagctgag ctaggagagg ttgttcgac     1440 cactggctgt tcgagtgact cgctgtagta ggcagaggac acagcttcct ccaggttgtc    1500
```

```
agtggtcttg agcagacact ccaccaaatc gttgtcagtg agcgagttaa ctgaggcgag    1560
gaagttgcta gcggcagcgg tttcagagtc ggagatgaca gtatcagctc cgtccgggt    1620 tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatctatc    1920
tagatgcatt cgcgaggtac cgagctcgaa ttcactggcc gtcgttttac aacgtcgtga    1980
ctgggaaaac cctggcgtta cccaacttaa tcgccttgca gcacatcccc ctttcgccag    2040
ctgctagcac catggctcga gcgtggagtt aactcgatgt gagttcaact gtactcttac    2100
cgagaatgca cccctttta tagcgctctg aaaagagact gagaatactt tattttctac    2160
aatcgtataa atcctagtg atggttacgg taatctttct tcatgggaag ctaaagatat    2220
tcgatagtta tgcttttggt ttctgttttgg gtgaaactta tgatcagatt atgatgaaac    2280
ttaaacttgc aagtaatatt tgagtttaaa ctattttaa tataatcacc taatatgtta    2340
tgacgtcaat aggcaggaca ttgacccgac gcgtccactc attaaaaata ttattacacc    2400
ttatataaaa tccatgatat cgttttggtg ttaaaccatt acgtattaac cataacctac    2460
cccaatgtaa ccttcagtca ccctaatcga tgttttttgta tacatcgatg ttgaccccaa    2520
caaaagattt ataattaatc ataatcacga acaacaacaa gtcaatgaaa caaataaaca    2580
agttgtcgat aaaacattca taatgacac agcaacatac aattcttgca taataaaaat    2640
ttaaatgaca tcatatttga gaataacaaa tgacattatc cctcgattgt gttttacaag    2700
tagaattcta cccgtaaagc gagtttagtt ttgaaaaaca aatgacatca tttgtataat    2760
gacatcatcc cctgattgtg ttttacaagt agaattctat ccgtaaagcg agttcagttt    2820
tgaaaacaaa tgagtcatac ctaaacacgt taataatctt ctgatatcag cttatgactc    2880
aagttatgag ccgtgtgcaa acatgagat aagtttatga catcatccac tgatcgtgcg    2940
ttacaagtag aattctactc gtaaagccag ttcggttatg agccgtgtgc aaaacatgac    3000
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaaatgttt cccgcgcgtt ggcacaacta tttacaatgc    3240
ggccaagtta taaaagattc taatctgata tgttttaaaa caccttttgcg gcccgagttg    3300 tttgcgtacg tgactagcga agaagatgtg tggaccgcag aacagatagt aaaacaaaac    3360
cctagtattg gagcaataat cgatgagctc gtcgacgtag gcctttgaat tccgcgcgct    3420
tcggaccggg atccaaaaac atcgattagg gtgactgaag gttacattgg ggtaggttat    3480
ggttaatacg taatggttta acaccaaaac gatatcatgg atttatata aggtgtaata    3540 atatttttaa tgagtggacg cgtcgggtca atgtcctgcc tattgacgtc ataacatatt    3600
aggtgattat attaaaaata gtttaaactc aaatattact tgcaagttta agtttcatca    3660
taatctgatc ataagtttca cccaaacaga aaccaaaagc ataactatcg aatatcttta    3720
gcttcccatg aagaaagatt accgtaacca tcactaggat tttatacgat tgtagaaaat    3780
aaagtattct cagtctcttt tcagagcgct ataaaaaggg gtgcattctc ggtaagagta    3840
cagttgaact cacatcgagt taactccacg ctgcagtctc gagatacgga cctttaattc    3900
```
aacccaacac aatatattat agttaaataa gaattattat caaatcattt gtatattaat    3960
taaaatacta tactgtaaat tacattttat ttacaatcac tcgac    4005

<210> SEQ ID NO 22
<211> LENGTH: 3898
<212> TYPE: DNA
<213> ORGANISM: Artificial Sequence
<220> FEATURE:
<223> OTHER INFORMATION: Recombinant expression cassette

<400> SEQUENCE: 22
ttagttgaac tcgaacttct tgtacttgca gttgagcttt tgctcggcga atgtgatggc    60
gtcggagagt ggcaccagtc cctgcaggat caaggccaag agcttcagca agttgttgtg    120
cagtgtagtt gactcgcgac ggttgacctt gccgatcacg aacatgtggt gcttgaatct    180
gttgtacttt tggatgacct ggctcacatc aacgtccttg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg acgagtact tgtatgtcag    480 agtgctcttc ttgttcacga tgaggttcag gttatcaacg acgtacttgt tgggagggtt    540
gtccgggaat tggacggact ccgagtactt gaggatctgg gaaacgtatg gcgagacgaa    600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac    1020
gtacttggcg aagatgattt cgaaaggctt cacctcggac ttcttaacga cgaacatgta    1080
gtaaccggtt tcagacatgt gatcggagaa tctgttcgag ttgtagtcgt tatcgtcgaa    1140
cctcatcagg taggggcga agtcgtttgt gaagtagtga gtgatctcct gggtggaagc    1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg gctggttgac    1380
accagcagag tgttcgaagg actcggcgtg gtaagctgag ctaggagagg gttgttcgac    1440
cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcggcagcgg tttcagagtc ggagatgaca gtatcagctc cgtccgggt    1620 tgggtggttg tagtaagaca agtaatcgtt aggttgcttg tcgcagaact ccgagtatga    1680
gttgtcgaag ctagcacgag agggagtgct ggcagaggta taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatctatc    1920

```
tagatgcatt cgcgaggtac cgagctcgaa ttcactggcc gtcgttttac aacgtcgtga    1980
ctgggaaaac cctggcgtta cccaacttaa tcgccttgca gcacatcccc ctttcgccag    2040
ctgctagcac catggctcga gcgtggagtt aactcgatgt gagttcaact gtactcttac    2100
cgagaatgca ccccttttta tagcgctctg aaaagagact gagaatactt tattttctac    2160
aatcgtataa atcctagtg atggttacgg taatctttct tcatgggaag ctaaagatat    2220
tcgatagtta tgcttttggt ttctgtttgg gtgaaactta tgatcagatt atgatgaaac    2280
ttaaacttgc aagtaatatt tgagtttaaa ctattttttaa tataatcacc taatatgtta    2340
tgacgtcaat aggcaggaca ttgacccgac gcgtccactc attaaaaata ttattacacc    2400
ttatataaaa tccatgatat cgttttggtg ttaaaccatt acgtattaac cataacctac    2460
cccaatgtaa ccttcagtca ccctaatcga tgttttttgta tacatcgatg ttgaccccaa    2520
caaaagattt ataattaatc ataatcacga acaacaacaa gtcaatgaaa caaataaaca    2580
agttgtcgat aaaacattca taatgacac agcaacatac aattcttgca taataaaaat    2640
ttaaatgaca tcatatttga gaataacaaa tgacattatc cctcgattgt gttttacaag    2700
tagaattcta cccgtaaagc gagtttagtt ttgaaaaaca aatgacatca tttgtataat    2760
gacatcatcc cctgattgtg ttttacaagt agaattctat ccgtaaagcg agttcagttt    2820
tgaaaacaaa tgagtcatac ctaaacacgt taataatctt ctgatatcag cttatgactc    2880
aagttatgag ccgtgtgcaa acatgagat aagtttatga catcatccac tgatcgtgcg    2940
ttacaagtag aattctactc gtaaagccag ttcggttatg agccgtgtgc aaaacatgac    3000
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaaatgttt cccgcgcgtt ggcacaacta tttacaatgc    3240
ggccaagtta taaagattc taatctgata tgttttaaaa cacctttgcg gcccgagttg    3300
tttgcgtacg tgactagcga agaagatgtg tggaccgcag aacagatagt aaaacaaaac    3360
cctagtattg gagcaataat cgatgagctc gtcgacgtag gcctttgaat tccgcgcgct    3420
tcggaccggg atcggtacca aattccgttt tgcgacgatg cagagttttt gaacaggctg    3480
ctcaaacaca tagatccgta cccgctcagt cggatgtatt acaatgcagc caataccatg    3540
ttttacacga ctatggaaaa ctatgccgtg tccaattgca agttcaacat tgaggattac    3600
aataacatat ttaaggtgat ggaaaatatt aggaaacaca gcaacaaaaa ttcaaacgac    3660
caagacgagt taaacatata tttgggagtt cagtcgtcga atgcaaagcg taaaaaatat    3720
taataaggta aaaattacag ctacataaat tacacaattt aaactgcagt ctggagatac    3780
ggacctttaa ttcaacccaa cacaatatat tatagttaaa taagaattat tatcaaatca    3840
tttgtatatt aattaaaata ctatactgta aattacattt tatttacaat cactcgac     3898
```

<210> SEQ ID NO 23
<211> LENGTH: 3179
<212> TYPE: DNA
<213> ORGANISM: Artificial Sequence
<220> FEATURE:
<223> OTHER INFORMATION: Recombinant expression cassette

<400> SEQUENCE: 23

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
```

-continued

```
cagtgtagtt gactcgcgac ggttgacctt gccgatcacg aacatgtggt gcttgaatct    180
gttgtacttt tggatgacct ggctcacatc aacgtccttg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcagacgaa     600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg taggggcga agtcgtttgt gaagtagtga gtgatctcct gggtggaagc    1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg ttgttcgac    1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccgggt    1620
tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatt   1920
gggtcatcta gattcgaaag cggccgcgac tagtgagctc gtcgacgtag gcctttgaat   1980
tccgcgcgct tcggaccggg atccgcgccc gatggtggga cggtatgaat aatccggaat   2040
atttataggt tttttattta caaaactgtt acgaaaacag taaatactt atttatttgc    2100
gagatggtta tcattttaat tatctccatg atctattaat attccggagt atacatcgat   2160
gttgaccca acaaaagatt tataattaat cataatcacg aacaacaaca agtcaatgaa    2220
acaaataaac aagttgtcga taaaacattc ataaatgaca cagcaacata caattcttgc   2280
ataataaaaa tttaaatgac atcatatttg agaataacaa atgacattat ccctcgattg   2340
tgttttacaa gtagaattct acccgtaaag cgagtttagt tttgaaaaac aaatgacatc   2400
atttgtataa tgacatcatc ccctgattgt gttttacaag tagaattcta tccgtaaagc   2460
```

```
gagttcagtt ttgaaaacaa atgagtcata cctaaacacg ttaataatct tctgatatca    2520
gcttatgact caagttatga gccgtgtgca aaacatgaga taagtttatg acatcatcca    2580
ctgatcgtgc gttacaagta gaattctact cgtaaagcca gttcggttat gagccgtgtg    2640
caaaacatga catcagctta tgactcatac ttgattgtgt tttacgcgta gaattctact    2700
cgtaaagcga gttcggttat gagccgtgtg caaaacatga catcagctta tgagtcataa    2760
ttaatcgtgc gttacaagta gaattctact cgtaaagcga gttgaaggat catatttagt    2820
tgcgtttatg agataagatt gaaagcacgt gtaaaatgtt tcccgcgcgt tggcacaact    2880
atttacaatg cggccaagtt ataaaagatt ctaatctgat atgttttaaa acacctttgc    2940
ggcccgagtt gtttgcgtac gtgactagcg aagaagatgt gtggaccgca gaacagatag    3000
taaaacaaaa ccctagtatt ggagcaataa tcgattccgg aatattaata gatcatggag    3060
ataattaaaa tgataaccat ctcgcaaata aataagtatt ttactgtttt cgtaacagtt    3120
ttgtaataaa aaaacctata aatattccgg attattcata ccgtcccacc atcgggcgc     3179
```

<210> SEQ ID NO 24
<211> LENGTH: 3528
<212> TYPE: DNA
<213> ORGANISM: Artificial Sequence
<220> FEATURE:
<223> OTHER INFORMATION: Recombinant expression cassette

<400> SEQUENCE: 24

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg gacgagtact tgtatgtcag     480
agtgctcttc ttgttcacga tgaggttcag gttatcaacg acgtacttgt tgggagggtt     540
gtccgggaat tggacggact ccgagtactt gaggatctgg gaaacgtatg gcagacgaa     600 gaagttgtta gaggcggttt cgatctcgtt tgattccttg cggctcagca tgatgggcaa     660
agtgaagagg ttcttgtcct ggtacatctc gtacaacttc acaagagga atccacactt     720 acgctcgccg agtgattgca gcaaggtcac gaaggttgtc tgagcgtagt acatatcgag     780
gttgaagtag gaggtcagag cggccttgaa tgtgtggtgg acgtccacga agtgacactt     840
cttgcagttt tgagcggcgg tctcatcgtt gcagacgtcc tgtgagtgtg ggatttcgat     900
gccagtctcc ttaaccaggt tgtagctgat catgaagcgg atcttatcga aggtcacaac     960
gaacacacgg ttgtcaacca tgtagtagtt gtttgtgtac tcgtagacca cgttagagac    1020
gtacttggcg aagatgattt cgaaaggctt cacctcggac ttcttaacga cgaacatgta    1080
gtaaccggtt tcagacatgt gatcggagaa tctgttcgag ttgtagtcgt tatcgtcgaa    1140
cctcatcagg taggggcga agtcgtttgt gaagtagtga gtgatctcct gggtggaagc    1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg gctggttgac    1380
```

```
accagcagag tgttcgaagg actcggcgtg gtaagctgag ctaggagagg gttgttcgac    1440
cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcggcagcgg tttcagagtc ggagatgaca gtatcagctc cgtccgggt    1620
tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatctatc    1920
tagatgcatt cgcgaggtac cgagctcgaa ttcactggcc gtcgttttac aacgtcgtga    1980
ctgggaaaac cctggcgtta cccaacttaa tcgccttgca gcacatcccc ctttcgccag    2040
ctgctagcac catggctcga gcgtggagtt aactcgatgt gagttcaact gtactcttac    2100
cgagaatgca ccccttttta tagcgctctg aaaagagact gagaatactt tattttctac    2160
aatcgtataa atcctagtg atggttacgg taatctttct tcatgggaag ctaaagatat    2220
tcgatagtta tgcttttggt ttctgtttgg gtgaaactta tgatcagatt atgatgaaac    2280
ttaaacttgc aagtaatatt tgagtttaaa ctatttttaa tataatcacc taatatgtta    2340
tgacgtcaat aggcaggaca ttgacccgac gcgtccactc attaaaaata ttattacacc    2400
ttatataaaa tccatgatat cgttttggtg ttaaaccatt acgtattaac cataacctac    2460
cccaatgtaa ccttcagtca ccctaatcga tgttttgta tacatcgatg ttgaccccaa    2520
caaaagattt ataattaatc ataatcacga acaacaacaa gtcaatgaaa caaataaaca    2580
agttgtcgat aaaacattca taatgacac agcaacatac aattcttgca taataaaaat    2640
ttaaatgaca tcatatttga gaataacaaa tgacattatc cctcgattgt gttttacaag    2700
tagaattcta cccgtaaagc gagtttagtt ttgaaaaaca aatgacatca tttgtataat    2760
gacatcatcc cctgattgtg ttttacaagt agaattctat ccgtaaagcg agttcagttt    2820
tgaaaacaaa tgagtcatac ctaaacacgt taataatctt ctgatatcag cttatgactc    2880
aagttatgag ccgtgtgcaa acatgagat aagtttatga catcatccac tgatcgtgcg    2940
ttacaagtag aattctactc gtaaagccag ttcggttatg agccgtgtgc aaaacatgac    3000
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagatta aaagcacgtg taaaatgttt cccgcgcgtt ggcacaacta tttcaatgc    3240
ggccaagtta taaagattc taatctgata tgttttaaaa cacctttgcg gcccgagttg    3300
tttgcgtacg tgactagcga agaagatgtg tggaccgcag aacagatagt aaaacaaaac    3360
cctagtattg gagcaataat cgattccgga atattaatag atcatggaga taattaaaat    3420
gataaccatc tcgcaaataa ataagtattt tactgttttc gtaacagttt tgtaataaaa    3480
aaacctataa atattccgga ttattcatac cgtcccacca tcgggcgc              3528
```

<210> SEQ ID NO 25
<211> LENGTH: 3291
<212> TYPE: DNA
<213> ORGANISM: Artificial Sequence
<220> FEATURE:

<223> OTHER INFORMATION: Recombinant expression cassette

<400> SEQUENCE: 25

```
ttagttgaac tcgaacttct tgtacttgca gttgagcttt tgctcggcga atgtgatggc        60
gtcggagagt ggcaccagtc cctgcaggat caaggccaag agcttcagca agttgttgtg       120
cagtgtagtt gactcgcgac ggttgacctt gccgatcacg aacatgtggt gcttgaatct       180
gttgtacttt tggatgacct ggctcacatc aacgtccttg atttcgccag agatccagta       240
gaactccttg ttcttcttag cgatggtcag cctttcctcg ttcttgaagg acaacacgat       300
gaagttgtga cccttaacgt tatcgacgtt ttgagtcaag tactgctcaa cgatgtgcat       360
gcttccgtct tccttcttga ccttcttgag gttctcggcg ttgttgttag aagcgatgtt       420
gtcgtggtac ttgtagttgt tgaagagcag gttagcgacg gacgagtact tgtatgtcag       480
agtgctcttc ttgttcacga tgaggttcag gttatcaacg acgtacttgt tgggagggtt       540
gtccgggaat tggacggact ccgagtactt gaggatctgg gaaacgtatg gcgagacgaa       600
gaagttgtta gaggcggttt cgatctcgtt tgattccttg cggctcagca tgatgggcaa       660
agtgaagagg ttcttgtcct ggtacatctc gtacaacttc gacaagagga atccacactt       720
acgctcgccg agtgattgca gcaaggtcac gaaggttgtc tgagcgtagt acatatcgag       780
gttgaagtag gaggtcagag cggccttgaa tgtgtggtgg acgtccacga agtgacactt       840
cttgcagttt tgagcggcgg tctcatcgtt gcagacgtcc tgtgagtgtg ggatttcgat       900
gccagtctcc ttaaccaggt tgtagctgat catgaagcgg atcttatcga aggtcacaac       960
gaacacacgg ttgtcaacca tgtagtagtt gtttgtgtac tcgtagacca cgttagagac      1020
gtacttggcg aagatgattt cgaaaggctt cacctcggac ttcttaacga cgaacatgta      1080
gtaaccggtt tcagacatgt gatcggagaa tctgttcgag ttgtagtcgt tatcgtcgaa      1140
cctcatcagg taggggcga agtcgtttgt gaagtagtga gtgatctcct gggtggaagc      1200
cactgtacag atgttagtgt tgtggttgat ggtttgttcc agtgtagcgc atgactggat      1260
ggtgctcttc ttgtacttag gtctcaactt gatcttgttg aattgaccca caactccctg      1320
ggagttatcc aggtactcgt ccaacttcct cttggtgcct gtggccgacg gctggttgac      1380
accagcagag tgttcgaagg actcggcgtg gtaagctgag ctaggagagg ttgttcgac       1440
cactggctgt tcgagtgact cgctgtagta ggcagaggac acagcttcct ccaggttgtc      1500
agtggtcttg agcagacact ccaccaaatc gttgtcagtg agcgagttaa ctgaggcgag      1560
gaagttgcta gcggcagcgg tttcagagtc ggagatgaca gtatcagctc cgtccggggt      1620
tgggtggttg tagtaagaca agtaatcgtt aggttgcttg tcgcagaact ccgagtatga      1680
gttgtcgaag ctagcacgag agggagtgct ggcagaggtg taggaagcgt tgaagttgat      1740
ttgagtcatg gtgacctggt tgttcacgat cttatcgcca cctgtgtcca cctgcagttg      1800
ctgggcctca gcgcaggctg aagtggcctc acaggagtag gggctggaag cacagttgga      1860
agtcatgatg ttttcttgga cgttcaggac gtggctggat gtacggatca tagatctatt      1920
gggtcatcta gattcgaaag cggccgcgac tagtgagctc gtcgacgtag gcctttgaat      1980
tccgcgcgct tcggacccgg atccgcgccc gatggtggga cggtatgaat aatccggaat      2040
atttataggt ttttttatta caaaactgtt acgaaaacag taaatactt atttatttgc       2100
gagatggtta tcatttaat tatctccatg atctattaat attccggagt atacatcgat      2160
gttgacccca acaaaagatt tataattaat cataatcacg aacaacaaca agtcaatgaa      2220
acaaataaac aagttgtcga taaaacattc ataaatgaca cagcaacata caattcttgc      2280
```

```
ataataaaaa tttaaatgac atcatatttg agaataacaa atgacattat ccctcgattg      2340
tgttttacaa gtagaattct acccgtaaag cgagtttagt tttgaaaaac aaatgacatc      2400
atttgtataa tgacatcatc ccctgattgt gttttacaag tagaattcta tccgtaaagc      2460
gagttcagtt ttgaaaacaa atgagtcata cctaaacacg ttaataatct tctgatatca      2520
gcttatgact caagttatga gccgtgtgca aaacatgaga taagtttatg acatcatcca      2580
ctgatcgtgc gttacaagta gaattctact cgtaaagcca gttcggttat gagccgtgtg      2640
caaaacatga catcagctta tgactcatac ttgattgtgt tttacgcgta gaattctact      2700
cgtaaagcga gttcggttat gagccgtgtg caaaacatga catcagctta tgagtcataa      2760
ttaatcgtgc gttacaagta gaattctact cgtaaagcga gttgaaggat catatttagt      2820
tgcgtttatg agataagatt gaaagcacgt gtaaaatgtt tcccgcgcgt tggcacaact      2880
atttacaatg cggccaagtt ataaaagatt ctaatctgat atgttttaaa cacctttgc      2940 ggcccgagtt gtttgcgtac gtgactagcg aagaagatgt gtggaccgca gaacagatag      3000
taaaacaaaa ccctagtatt ggagcaataa tcgatgagct catcatggag ataattaaaa      3060
tgataaccat ctcgcaaata aataagtatt ttactgtttt cgtaacagtt ttgtaataaa      3120
aaaacctata aatattccgg attattcata ccgtcccacc atcgggcgca tacggacctt      3180
taattcaacc caacacaata tattatagtt aaataagaat tattatcaaa tcatttgtat      3240
attaattaaa atactatact gtaaattaca ttttatttac aatcactcga c              3291
```

<210> SEQ ID NO 26
<211> LENGTH: 3640
<212> TYPE: DNA
<213> ORGANISM: Artificial Sequence
<220> FEATURE:
<223> OTHER INFORMATION: Recombinant expression cassette

<400> SEQUENCE: 26

```
ttagttgaac tcgaacttct tgtacttgca gttgagcttt tgctcggcga atgtgatggc        60
gtcggagagt ggcaccagtc cctgcaggat caaggccaag agcttcagca agttgttgtg       120
cagtgtagtt gactcgcgac ggttgacctt gccgatcacg aacatgtggt gcttgaatct       180
gttgtacttt tggatgacct ggctcacatc aacgtccttg atttcgccag agatccagta       240
gaactccttg ttcttcttag cgatggtcag cctttcctcg ttcttgaagg acaacacgat       300
gaagttgtga cccttaacgt tatcgacgtt ttgagtcaag tactgctcaa cgatgtgcat       360
gcttccgtct tccttcttga ccttcttgag gttctcggcg ttgttgttag aagcgatgtt       420
gtcgtggtac ttgtagttgt tgaagagcag gttagcgacg gacgagtact tgtatgtcag       480
agtgctcttc ttgttcacga tgaggttcag gttatcaacg acgtacttgt tgggagggtt       540
gtccgggaat tggacggact ccgagtactt gaggatctgg aaacgtatg gcgagacgaa        600 gaagttgtta gaggcggttt cgatctcgtt tgattccttg cggctcagca tgatgggcaa       660
agtgaagagg ttcttgtcct ggtacatctc gtacaacttc gacaagagga atccacactt       720
acgctcgccg agtgattgca gcaaggtcac gaaggttgtc tgagcgtagt acatatcgag       780
gttgaagtag gaggtcagag cggccttgaa tgtgtggtgg acgtccacga agtgacactt       840
cttgcagttt tgagcggcgg tctcatcgtt gcagacgtcc tgtgagtgtg ggatttcgat       900
gccagtctcc ttaaccaggt tgtagctgat catgaagcgg atcttatcga aggtcacaac       960
gaacacacgg ttgtcaacca tgtagtagtt gtttgtgtac tcgtagacca cgttagagac      1020
```

```
gtacttggcg aagatgattt cgaaaggctt cacctcggac ttcttaacga cgaacatgta    1080
gtaaccggtt tcagacatgt gatcggagaa tctgttcgag ttgtagtcgt tatcgtcgaa    1140
cctcatcagg tagggggcga agtcgtttgt gaagtagtga gtgatctcct gggtggaagc    1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg gctggttgac    1380
accagcagag tgttcgaagg actcggcgtg gtaagctgag ctaggagagg gttgttcgac    1440
cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcgcagcgg tttcagagtc ggagatgaca gtatcagctc cgtccgggt    1620 tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatctatc    1920
tagatgcatt cgcgaggtac cgagctcgaa ttcactggcc gtcgttttac aacgtcgtga    1980
ctgggaaaac cctggcgtta cccaacttaa tcgccttgca gcacatcccc ctttcgccag    2040
ctgctagcac catggctcga gcgtggagtt aactcgatgt gagttcaact gtactcttac    2100
cgagaatgca ccccttttta tagcgctctg aaaagagact gagaatactt tattttctac    2160
aatcgtataa aatcctagtg atggttacgg taatctttct tcatgggaag ctaaagatat    2220
tcgatagtta tgcttttggt ttctgtttgg gtgaaactta tgatcagatt atgatgaaac    2280
ttaaacttgc aagtaatatt tgagtttaaa ctattttaa tataatcacc taatatgtta    2340
tgacgtcaat aggcaggaca ttgacccgac gcgtccactc attaaaaata ttattacacc    2400
ttatataaaa tccatgatat cgttttggtg ttaaaccatt acgtattaac cataacctac    2460
cccaatgtaa ccttcagtca ccctaatcga tgtttttgta tacatcgatg ttgaccccaa    2520
caaaagattt ataattaatc ataatcacga acaacaacaa gtcaatgaaa caaataaaca    2580
agttgtcgat aaaacattca taaatgacac agcaacatac aattcttgca taataaaaat    2640
ttaaatgaca tcatatttga gaataacaaa tgacattatc cctcgattgt gttttacaag    2700
tagaattcta cccgtaaagc gagtttagtt ttgaaaaaca aatgacatca tttgtataat    2760
gacatcatcc cctgattgtg ttttacaagt agaattctat ccgtaaagcg agttcagttt    2820
tgaaaacaaa tgagtcatac ctaaacacgt taataatctt ctgatatcag cttatgactc    2880
aagttatgag ccgtgtgcaa acatgagat aagtttatga catcatccac tgatcgtgcg    2940
ttacaagtag aattctactc gtaaagccag ttcggttatg agccgtgtgc aaaacatgac    3000
atcagcttat gactcatact tgattgtgtt ttacgcgtag aattctactc gtaaagcgag    3060
ttcggttatg agccgtgtgc aaaacatgac atcagcttat gagtcataat taatcgtgcg    3120
ttacaagtag aattctactc gtaaagcgag ttgaaggatc atatttagtt gcgtttatga    3180
gataagattg aaagcacgtg taaatgtttt cccgcgcgtt ggcacaacta tttacaatgc    3240
ggccaagtta taaagattc taatctgata tgttttaaaa caccttgcg gcccgagttg    3300 tttgcgtacg tgactagcga agaagatgtg tggaccgcag aacagatagt aaaacaaaac    3360
cctagtattg gagcaataat cgatgagctc atcatggaga taattaaaat gataaccatc    3420
```

-continued

```
tcgcaaataa ataagtattt tactgttttc gtaacagttt tgtaataaaa aaacctataa    3480
atattccgga ttattcatac cgtcccacca tcgggcgcat acggaccttt aattcaaccc    3540
aacacaatat attatagtta ataagaatt attatcaaat catttgtata ttaattaaaa    3600
tactatactg taaattacat tttatttaca atcactcgac                          3640
```

<210> SEQ ID NO 27
<211> LENGTH: 881
<212> TYPE: DNA
<213> ORGANISM: Autographa californica nucleopolyhedrovirus

<400> SEQUENCE: 27

```
atcgatgttg accccaacaa aagatttata attaatcata atcacgaaca acaacaagtc      60
aatgaaacaa ataaacaagt tgtcgataaa acattcataa atgacacagc aacatacaat    120
tcttgcataa taaaaattta atgacatca tatttgagaa taacaaatga cattatccct    180
cgattgtgtt ttacaagtag aattctaccc gtaaagcgag tttagttttg aaaaacaaat    240
gacatcattt gtataatgac atcatcccct gattgtgttt tacaagtaga attctatccg    300
taaagcgagt tcagttttga aaacaaatga gtcatacta aacacgttaa taatcttctg    360
atatcagctt atgactcaag ttatgagccg tgtgcaaaac atgagataag tttatgacat    420
catccactga tcgtgcgtta caagtagaat tctactcgta aagccagttc ggttatgagc    480
cgtgtgcaaa acatgacatc agcttatgac tcatacttga ttgtgtttta cgcgtagaat    540
tctactcgta aagcgagttc ggttatgagc cgtgtgcaaa acatgacatc agcttatgag    600
tcataattaa tcgtgcgtta caagtagaat tctactcgta aagcgagttg aaggatcata    660
tttagttgcg tttatgagat aagattgaaa gcacgtgtaa aatgtttccc cgcgcgttggc    720 acaactattt acaatgcggc caagttataa aagattctaa tctgatatgt tttaaaacac    780
ctttgcggcc cgagttgttt gcgtacgtga ctagcgaaga agatgtgtgg accgcagaac    840
agatagtaaa acaaaaccct agtattggag caataatcga t                        881
```

<210> SEQ ID NO 28
<211> LENGTH: 2124
<212> TYPE: DNA
<213> ORGANISM: Artificial Sequence
<220> FEATURE:
<223> OTHER INFORMATION: Recombinant DNA construct fusing the Ac-ie-01
      cDNA to the polh promoter

<400> SEQUENCE: 28

```
atcatggaga taattaaaat gataaccatc tcgcaaataa ataagtattt tactgttttc     60
gtaacagttt tgtaataaaa aaacctataa atattccgga ttattcatac cgtcccacca    120
tcgggcgcgg atcccggtcc gaagcgcgcg gaattcaaag gcctacgtcg acgagctcac    180
tagtcgcggc cgctttcgaa tctagataga tctatgatcc gtacatccag ccacgtcctg    240
aacgtccaag aaaacatcat gacttccaac tgtgcttcca gcccctactc ctgtgaggcc    300
acttcagcct gcgctgaggc ccagcaactg caggtggaca caggtggcga taagatcgtg    360
aacaaccagg tcaccatgac tcaaatcaac ttcaacgctt cctacacctc tgccagcact    420
ccctctcgtg ctagcttcga caactcatac tcggagttct gcgacaagca acctaacgat    480
tacttgtctt actacaacca cccaaccccg gacggagctg atactgtcat ctccgactct    540
gaaaccgctg ccgctagcaa cttcctcgcc tcagttaact cgctcactga caacgatttg    600
gtggagtgtc tgctcaagac cactgacaac ctggaggaag ctgtgtcctc tgcctactac    660
```

```
agcgagtcac tcgaacagcc agtggtcgaa caaccctctc ctagctcagc ttaccacgcc    720
gagtccttcg aacactctgc tggtgtcaac cagccgtcgg ccacaggcac caagaggaag    780
ttggacgagt acctggataa ctcccaggga gttgtgggtc aattcaacaa gatcaagttg    840
agacctaagt acaagaagag caccatccag tcatgcgcta cactggaaca aaccatcaac    900
cacaacacta acatctgtac agtggcttcc acccaggaga tcactcacta cttcacaaac    960
gacttcgccc cctacctgat gaggttcgac gataacgact acaactcgaa cagattctcc   1020
gatcacatgt ctgaaaccgg ttactacatg ttcgtcgtta agaagtccga ggtgaagcct   1080
ttcgaaatca tcttcgccaa gtacgtctct aacgtggtct acgagtacac aaacaactac   1140
tacatggttg acaaccgtgt gttcgttgtg accttcgata agatccgctt catgatcagc   1200
tacaacctgg ttaaggagac tggcatcgaa atcccacact cacaggacgt ctgcaacgat   1260
gagaccgccg ctcaaaactg caagaagtgt cacttcgtgg acgtccacca cacattcaag   1320
gccgctctga cctcctactt caacctcgat atgtactacg ctcagacaac cttcgtgacc   1380
ttgctgcaat cactcggcga gcgtaagtgt ggattcctct tgtcgaagtt gtacgagatg   1440
taccaggaca agaacctctt cactttgccc atcatgctga ccgcaaggaa atcaaacgag   1500
atcgaaaccg cctctaacaa cttcttcgtc tcgccatacg tttcccagat cctcaagtac   1560
tcggagtccc tccaattccc ggacaaccct cccaacaagt acgtcgttga taacctgaac   1620
ctcatcgtga acaagaagag cactctgaca tacaagtact cgtccgtcgc taacctgctc   1680
ttcaacaact acaagtacca cgacaacatc gcttctaaca caacgccga gaacctcaag   1740 aaggtcaaga aggaagacgg aagcatgcac atcgttgagc agtacttgac tcaaaacgtc   1800
gataacgtta agggtcacaa cttcatcgtg ttgtccttca agaacgagga aaggctgacc   1860
atcgctaaga agaacaagga gttctactgg atctctggcg aaatcaagga cgttgatgtg   1920
agccaggtca tccaaaagta caacagattc aagcaccaca tgttcgtgat cggcaaggtc   1980
aaccgtcgcg agtcaactac actgcacaac aacttgctga agctcttggc cttgatcctg   2040
cagggactgg tgccactctc cgacgccatc acattcgccg agcaaaagct caactgcaag   2100
tacaagaagt tcgagttcaa ctaa                                          2124
```

<210> SEQ ID NO 29
<211> LENGTH: 911
<212> TYPE: DNA
<213> ORGANISM: Artificial Sequence
<220> FEATURE:
<223> OTHER INFORMATION: Recombinant DNA construct fusing the GFP cDNA
    to the polh promoter

<400> SEQUENCE: 29

```
atcatggaga taattaaaat gataaccatc tcgcaaataa ataagtattt tactgttttc     60
gtaacagttt tgtaataaaa aaacctataa atattccgga ttattcatac cgtcccacca    120
tcgggcgcgg atccaaggcc actagtgcgg ccgctctgca gtctcgagca tgcggtacca    180
agcttgaatt catggtgagc aagggcgagg agctgttcac cggggtggtg cccatcctgg    240
tcgagctgga cggcgacgta aacggccaca agttcagcgt gtccggcgag ggcgagggcg    300
atgccaccta cggcaagctg accctgaagt tcatctgcac caccggcaag ctgcccgtgc    360
cctggcccac cctcgtgacc accctgacct acggcgtgca gtgcttcagc cgctaccccg    420
accacatgaa gcagcacgac ttcttcaagt ccgccatgcc cgaaggctac gtccaggagc    480
gcaccatctt cttcaaggac gacggcaact acaagacccg cgccgaggtg aagttcgagg    540
```

```
gcgacaccct ggtgaaccgc atcgagctga agggcatcga cttcaaggag gacggcaaca    600
tcctggggca aagctggag tacaactaca acagccacaa cgtctatatc atggccgaca    660
agcagaagaa cggcatcatg gtgaacttca agatccgcca caacatcgag gacggcagcg    720
tgcagctcgc cgaccactac cagcagaaca cccccatcgg cgacggcccc gtgctgctgc    780
ccgacaacca ctacctgagc acccagtccg ccctgagcaa agaccccaac gagaagcgcg    840
atcacatggt cctgctggag ttcgtgaccg ccgccgggat cactctcggc atggacgagc    900
tgtacaagta a                                                          911
```

<210> SEQ ID NO 30
<211> LENGTH: 3873
<212> TYPE: DNA
<213> ORGANISM: Artificial Sequence
<220> FEATURE:
<223> OTHER INFORMATION: Recombinant expression cassette

<400> SEQUENCE: 30

```
ttagttgaac tcgaacttct tgtacttgca gttgagcttt tgctcggcga atgtgatggc     60
gtcggagagt ggcaccagtc cctgcaggat caaggccaag agcttcagca agttgttgtg    120
cagtgtagtt gactcgcgac ggttgacctt gccgatcacg aacatgtggt gcttgaatct    180 gttgtactt tggatgacct ggctcacatc aacgtcctg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcagacgaa    600 gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgt tgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg tagggggcga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg ttgttcgac   1440 cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccgggt   1620
```

```
tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatctatc    1920
tagattcgaa agcggccgcg actagtgagc tcgtcgacgt aggcctttga attccgcgcg    1980
cttcggaccg ggatccgcgc ccgatggtgg gacggtatga ataatccgga atatttatag    2040
gtttttttat tacaaaactg ttacgaaaac agtaaaatac ttatttattt gcgagatggt    2100
tatcatttta attatctcca tgatctatta atattccgga gtatacctac ccgtaaagcg    2160
agtttagttt tgaaaaacaa atgacatcat ttgtataatg acatcatccc ctgattgtgt    2220
tttacaagta gaattctatc cgtaaagcga gttcagtttt gaaaacaaat gagtcatacc    2280
taaacacgtt aataatcttc tgatatcagc ttatgactca agttatgagc cgtgtgcaaa    2340
acatgagata agtttatgac atcatccact gatcgtgcgt tacaagtaga attctactcg    2400
taaagccagt tcggttatga gccgtgtgca aaacatgaca tcagcttatg actcatactt    2460
gattgtgttt tacgcgtaga attctactcg taaagcgagt tcggttatga gccgtgtgca    2520
aaacatgaca tcagcttatg agtcataatt aatcgtgcgt tacaagtaga attctactcg    2580
taaagcgagt tgaaggatca tatttagttg cgtttatgag ataagattga aagcacgtgt    2640
aaaatgtttc cgagctcgtc gacgtaggcc tttgaattcc gcgcgcttcg gaccgggatc    2700
ggtaccaaat tccgttttgc gacgatgcag agttttttgaa caggctgctc aaacacatag    2760
atccgtaccc gctcagtcgg atgtattaca atgcagccaa taccatgttt tacacgacta    2820
tggaaaacta tgccgtgtcc aattgcaagt tcaacattga ggattacaat aacatattta    2880
aggtgatgga aaatattagg aaacacagca acaaaaattc aaacgaccaa gacgagttaa    2940
acatatattt gggagttcag tcgtcgaatg caaagcgtaa aaaatattaa taaggtaaaa    3000
attacagcta cataaattac acaatttaaa ctgcagtctg gagatacgga cctttaattc    3060
aacccaacac aatatattat agttaaataa gaattattat caaatcattt gtatattaat    3120
taaaatacta tactgtaaat tacatttat ttacaatcac tcgacctcga gatgacgtat     3180
ccaaggaggc gtttccgcag acgaagacac cgcccccgca gccatcttgg ccagatcctc    3240
cgccgccgcc cctggctcgt ccaccccgc caccgttacc gctggagaag gaaaaatggc    3300
atcttcaaca cccgcctctc ccgcaccttc ggatatactg tcaaggctac cacagtcaca    3360
acgccctcct gggcggtgga catgatgaga tttaatatta cgactttgt tccccgggga    3420 gggggacca acaaaatctc tatacccttt gaatactaca gaataagaaa ggttaaggtt    3480
gaattctggc cctgctcccc aatcacccag ggtgacaggg gagtgggctc cactgctgtt    3540
attctagatg ataactttgt aacaaaggcc acagccctaa cctatgaccc ctatgtaaac    3600
tactcctccc gccatacaat ccccaaccc ttctcctacc actcccgtta cttcacaccc     3660
aaacctgtac tggatagaac tattgattac ttccagccaa acaacaaaaa aaatcagctt    3720
tggctgaggc tacaaacctc tgcaaatgta gaccacgtag gcctcggcac tgcgttcgaa    3780
aacagtaaat acgaccagga ctacaatatc cgtgtaacca tgtatgtaca attcagagaa    3840
tttaatctta aagaccccccc acttaaaccc taa                                3873
```

<210> SEQ ID NO 31
<211> LENGTH: 702

-continued

<212> TYPE: DNA
<213> ORGANISM: Porcine circovirus type 2

<400> SEQUENCE: 31

```
atgacgtatc caaggaggcg tttccgcaga cgaagacacc gcccccgcag ccatcttggc     60
cagatcctcc gccgccgccc ctggctcgtc cacccccgcc accgttaccg ctggagaagg    120
aaaaatggca tcttcaacac ccgcctctcc cgcaccttcg gatatactgt caaggctacc    180
acagtcacaa cgccctcctg ggcggtggac atgatgagat ttaatattaa cgactttgtt    240
cccccgggag gggggaccaa caaaatctct ataccctttg aatactacag aataagaaag    300
gttaaggttg aattctggcc ctgctcccca atcacccagg gtgacagggg agtgggctcc    360
actgctgtta ttctagatga taactttgta acaaaggcca cagccctaac ctatgacccc    420
tatgtaaact actcctcccg ccatacaatc ccccaaccct tctcctacca ctcccgttac    480
ttcacaccca aacctgtact ggatagaact attgattact tccagccaaa caacaaaaaa    540
aatcagcttt ggctgaggct acaaacctct gcaaatgtag accacgtagg cctcggcact    600
gcgttcgaaa acagtaaata cgaccaggac tacaatatcc gtgtaaccat gtatgtacaa    660
ttcagagaat ttaatcttaa agaccccca cttaaaccct aa                        702
```

<210> SEQ ID NO 32
<211> LENGTH: 233
<212> TYPE: PRT
<213> ORGANISM: Porcine circovirus type 2

<400> SEQUENCE: 32

```
Met Thr Tyr Pro Arg Arg Arg Phe Arg Arg Arg Arg His Arg Pro Arg
1               5                   10                  15

Ser His Leu Gly Gln Ile Leu Arg Arg Arg Pro Trp Leu Val His Pro
            20                  25                  30

Arg His Arg Tyr Arg Trp Arg Arg Lys Asn Gly Ile Phe Asn Thr Arg
        35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asn Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Arg Thr Ile Asp Tyr Phe Gln Pro
                165                 170                 175

Asn Asn Lys Lys Asn Gln Leu Trp Leu Arg Leu Gln Thr Ser Ala Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230

<210> SEQ ID NO 33
<211> LENGTH: 836
<212> TYPE: DNA
<213> ORGANISM: Artificial Sequence
<220> FEATURE:
<223> OTHER INFORMATION: Recombinant DNA construct fusing the Cap cDNA
      to the polh promoter

<400> SEQUENCE: 33

```
atcatggaga taattaaaat gataaccatc tcgcaaataa ataagtattt tactgttttc      60
gtaacagttt tgtaataaaa aaacctataa atattccgga ttattcatac cgtcccacca     120
tcgggcgcgg atccatgacg tatccaagga ggcgtttccg cagacgaaga caccgccccc     180
gcagccatct tggccagatc ctccgccgcc gcccctggct cgtccacccc cgccaccgtt     240
accgctggag aaggaaaaat ggcatcttca cacccgcct ctcccgcacc ttcggatata      300
ctgtcaaggc taccacagtc acaacgccct cctgggcggt ggacatgatg agatttaata     360
ttaacgactt tgttccccg ggagggggga ccaacaaaat ctctataccc tttgaatact      420
acagaataag aaaggttaag gttgaattct ggccctgctc cccaatcacc cagggtgaca     480
ggggagtggg ctccactgct gttattctag atgataactt tgtaacaaag gccacagccc     540
taacctatga cccctatgta aactactcct cccgccatac aatcccccaa cccttctcct     600
accactcccg ttacttcaca cccaaacctg tactggatag aactattgat tacttccagc     660
caaacaacaa aaaaaatcag ctttggctga ggctacaaac ctctgcaaat gtagaccacg     720
taggcctcgg cactgcgttc gaaaacagta atacgacca ggactacaat atccgtgtaa      780
ccatgtatgt acaattcaga gaattaatc ttaaagaccc cccacttaaa ccctaa          836
```

<210> SEQ ID NO 34
<211> LENGTH: 3891
<212> TYPE: DNA
<213> ORGANISM: Artificial Sequence
<220> FEATURE:
<223> OTHER INFORMATION: Recombinant expression cassette

<400> SEQUENCE: 34

```
ttagttgaac tcgaacttct tgtacttgca gttgagcttt tgctcggcga atgtgatggc      60
gtcggagagt ggcaccagtc cctgcaggat caaggccaag agcttcagca gttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag ccttttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg gacgagtact tgtatgtcag     480
agtgctcttc ttgttcacga tgaggttcag gttatcaacg acgtacttgt tgggagggtt     540
gtccgggaat tggacggact ccgagtactc gaggatctgg gaaacgtatg gcagacgaa      600
gaagttgtta gaggcggttt cgatctcgtt tgattccttg cggctcagca tgatgggcaa     660
agtgaagagg ttcttgtcct ggtacatctc gtacaacttc gacaagagga atccacactt     720
acgctcgccg agtgattgca gcaaggtcac gaaggttgtc tgagcgtagt acatatcgag     780
gttgaagtag gaggtcagag cggccttgaa tgtgtggtgg acgtccacga agtgacactt     840
```

```
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg taggggcga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg gttgttcgac   1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccggggt   1620
tgggtggtta tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatc   1920
tagattcgaa agcggccgcg actagtgagc tcgtcgacgt aggcctttga attccgcgcg   1980
cttcggaccg ggatccgcgc ccgatggtgg gacggtatga ataatccgga atatttatag   2040 gttttttat tacaaaactg ttacgaaaac agtaaaatac ttatttattt gcgagatggt   2100
tatcatttta attatctcca tgatctatta atattccgga gtataccctac ccgtaaagcg   2160 agtttagttt tgaaaaacaa atgacatcat ttgtataatg acatcatccc ctgattgtgt   2220
tttacaagta gaattctatc cgtaaagcga gttcagtttt gaaaacaaat gagtcatacc   2280
taaacacgtt aataatcttc tgatatcagc ttatgactca agttatgagc cgtgtgcaaa   2340
acatgagata agtttatgac atcatccact gatcgtgcgt tacaagtaga attctactcg   2400
taaagccagt tcggttatga gccgtgtgca aaacatgaca tcagcttatg actcatactt   2460
gattgtgttt tacgcgtaga attctactcg taaagcgagt tcggttatga gccgtgtgca   2520
aaacatgaca tcagcttatg agtcataatt aatcgtgcgt tacaagtaga attctactcg   2580
taaagcgagt tgaaggatca tatttagttg cgtttatgag ataagattga agcacgtgt   2640 aaaatgtttc cgagctcgtc gacgtaggcc tttgaattcc gcgcgcttcg gacccgggatc   2700 ggtaccaaat tccgttttgc gacgatgcag agttttgaa caggctgctc aaacacatag   2760
atccgtaccc gctcagtcgg atgtattaca atgcagccaa taccatgttt tacacgacta   2820
tggaaaacta tgccgtgtcc aattgcaagt tcaacattga ggattacaat aacatattta   2880
aggtgatgga aaatattagg aaacacagca acaaaaattc aaacgaccaa gacgagttaa   2940
acatatattt gggagttcag tcgtcgaatg caaagcgtaa aaaatattaa taaggtaaaa   3000
attacagcta cataaattac acaatttaaa ctgcagtctg gagatacgga ccttaattc    3060 aacccaacac aatatattat agttaaataa gaattattat caaatcattt gtatattaat   3120
taaaatacta tactgtaaat tacatttat ttacaatcac tcgacctcga gatggtgagc   3180
```

| | |
|---|---|
| aagggcgagg agctgttcac cggggtggtg cccatcctgg tcgagctgga cggcgacgta | 3240 |
| aacggccaca agttcagcgt gtccggcgag ggcgagggcg atgccaccta cggcaagctg | 3300 |
| accctgaagt tcatctgcac caccggcaag ctgcccgtgc cctggcccac cctcgtgacc | 3360 |
| accctgacct acggcgtgca gtgcttcagc cgctaccccg accacatgaa gcagcacgac | 3420 |
| ttcttcaagt ccgccatgcc cgaaggctac gtccaggagc gcaccatctt cttcaaggac | 3480 |
| gacggcaact acaagacccg cgccgaggtg aagttcgagg gcgacaccct ggtgaaccgc | 3540 |
| atcgagctga agggcatcga cttcaaggag gacggcaaca tcctgggcca caagctggag | 3600 |
| tacaactaca acagccacaa cgtctatatc atggccgaca gcagaagaa cggcatcatg | 3660 |
| gtgaacttca agatccgcca caacatcgag gacggcagcg tgcagctcgc cgaccactac | 3720 |
| cagcagaaca cccccatcgg cgacggcccc gtgctgctgc ccgacaacca ctacctgagc | 3780 |
| acccagtccg ccctgagcaa agaccccaac gagaagcgcg atcacatggt cctgctggag | 3840 |
| ttcgtgaccg ccgccgggat cactctcggc atggacgagc tgtacaagta a | 3891 |

<210> SEQ ID NO 35
<211> LENGTH: 3618
<212> TYPE: DNA
<213> ORGANISM: Artificial Sequence
<220> FEATURE:
<223> OTHER INFORMATION: Recombinant expression cassette

<400> SEQUENCE: 35

| | |
|---|---|
| ttagttgaac tcgaacttct tgtacttgca gttgagcttt tgctcggcga atgtgatggc | 60 |
| gtcggagagt ggcaccagtc cctgcaggat caaggccaag agcttcagca agttgttgtg | 120 |
| cagtgtagtt gactcgcgac ggttgacctt gccgatcacg aacatgtggt gcttgaatct | 180 |
| gttgtacttt tggatgacct ggctcacatc aacgtccttg atttcgccag agatccagta | 240 |
| gaactccttg ttcttcttag cgatggtcag cctttcctcg ttcttgaagg acaacacgat | 300 |
| gaagttgtga cccttaacgt tatcgacgtt ttgagtcaag tactgctcaa cgatgtgcat | 360 |
| gcttccgtct tccttcttga ccttcttgag gttctcggcg ttgttgttag aagcgatgtt | 420 |
| gtcgtggtac ttgtagttgt tgaagagcag gttagcgacg gacgagtact tgtatgtcag | 480 |
| agtgctcttc ttgttcacga tgaggttcag gttatcaacg acgtacttgt tgggagggtt | 540 |
| gtccgggaat tggacggact ccgagtactt gaggatctgg aaacgtatg gcagacgaa | 600 |
| gaagttgtta gaggcggttt cgatctcgtt tgattccttg cggctcagca tgatgggcaa | 660 |
| agtgaagagg ttcttgtcct ggtacatctc gtacaacttc gacaagagga atccacactt | 720 |
| acgctcgccg agtgattgca gcaaggtcac gaaggttgtc tgagcgtagt acatatcgag | 780 |
| gttgaagtag gaggtcagag cggccttgaa tgtgtggtgg acgtccacga agtgacactt | 840 |
| cttgcagttt tgagcggcgg tctcatcgtt gcagacgtcc tgtgagtgtg ggatttcgat | 900 |
| gccagtctcc ttaaccaggt tgtagctgat catgaagcgg atcttatcga aggtcacaac | 960 |
| gaacacacgg ttgtcaacca tgtagtagtt gtttgtgtac tcgtagacca cgttagagac | 1020 |
| gtacttggcg aagatgattt cgaaaggctt cacctcggac ttcttaacga cgaacatgta | 1080 |
| gtaaccggtt tcagacatgt gatcggagaa tctgttcgag ttgtagtcgt tatcgtcgaa | 1140 |
| cctcatcagg taggggcga agtcgtttgt gaagtagtga gtgatctcct gggtggaagc | 1200 |
| cactgtacag atgttagtgt tgtggttgat ggtttgttcc agtgtagcgc atgactggat | 1260 |
| ggtgctcttc ttgtacttag gtctcaactt gatcttgttg aattgaccca caactccctg | 1320 |
| ggagttatcc aggtactcgt ccaacttcct cttggtgcct gtggccgacg gctggttgac | 1380 |

```
accagcagag tgttcgaagg actcggcgtg gtaagctgag ctaggagagg gttgttcgac    1440
cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcggcagcgg tttcagagtc ggagatgaca gtatcagctc cgtccggggt    1620
tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatccgcg    1920
cccgatggtg ggacggtatg aataatccgg aatatttata ggttttttta ttacaaaact    1980
gttacgaaaa cagtaaaata cttatttatt tgcgagatgg ttatcatttt aattatctcc    2040
atgatctatt aatattccgg agtataccta cccgtaaagc gagtttagtt ttgaaaaaca    2100
aatgacatca tttgtataat gacatcatcc cctgattgtg ttttacaagt agaattctat    2160
ccgtaaagcg agttcagttt tgaaaacaaa tgagtcatac ctaaacacgt taataatctt    2220
ctgatatcag cttatgactc aagttatgag ccgtgtgcaa acatgagat aagtttatga    2280 catcatccac tgatcgtgcg ttacaagtag aattctactc gtaaagccag ttcggttatg    2340
agccgtgtgc aaaacatgac atcagcttat gactcatact tgattgtgtt ttacgcgtag    2400
aattctactc gtaaagcgag ttcggttatg agccgtgtgc aaaacatgac atcagcttat    2460
gagtcataat taatcgtgcg ttacaagtag aattctactc gtaaagcgag ttgaaggatc    2520
atatttagtt gcgtttatga gataagattg aaagcacgtg taaatgtttt ccgagctcat    2580
catggagata attaaaatga taaccatctc gcaaataaat aagtatttta ctgttttcgt    2640
aacagttttg taataaaaaa acctataaat attccggatt attcataccg tcccaccatc    2700
gggcgcgagc tcatacggac ctttaattca acccaacaca atatattata gttaaataag    2760
aattattatc aaatcatttg tatattaatt aaaatactat actgtaaatt acattttatt    2820
tacaatcact cgacctcgag ccatggttct agacagctga tgcatactag agcctgcagt    2880
ctcgacaagc ttgaattcat ggtgagcaag ggcgaggagc tgttcaccgg ggtggtgccc    2940
atcctggtcg agctggacgg cgacgtaaac ggccacaagt tcagcgtgtc cggcgagggc    3000
gagggcgatg ccacctacgg caagctgacc ctgaagttca tctgcaccac cggcaagctg    3060
cccgtgccct ggcccaccct cgtgaccacc ctgacctacg gcgtgcagtg cttcagccgc    3120
taccccgacc acatgaagca gcacgacttc ttcaagtccg ccatgcccga aggctacgtc    3180
caggagcgca ccatcttctt caaggacgac ggcaactaca agacccgcgc cgaggtgaag    3240
ttcgagggcg acaccctggt gaaccgcatc gagctgaagg gcatcgactt caaggaggac    3300
ggcaacatcc tggggcacaa gctggagtac aactacaaca gccacaacgt ctatatcatg    3360
gccgacaagc agaagaacgg catcatggtg aacttcaaga tccgccacaa catcgaggac    3420
ggcagcgtgc agctcgccga ccactaccag cagaacaccc ccatcggcga cggccccgtg    3480
ctgctgcccg acaaccacta cctgagcacc cagtccgccc tgagcaaaga ccccaacgag    3540
aagcgcgatc acatggtcct gctggagttc gtgaccgccg ccgggatcac tctcggcatg    3600
gacgagctgt acaagtaa                                                  3618
```

<210> SEQ ID NO 36

<211> LENGTH: 3950
<212> TYPE: DNA
<213> ORGANISM: Artificial Sequence
<220> FEATURE:
<223> OTHER INFORMATION: Recombinant expression cassette

<400> SEQUENCE: 36

| | | | | | |
|---|---|---|---|---|---|
| ttagttgaac | tcgaacttct | tgtacttgca | gttgagcttt | tgctcggcga | atgtgatggc | 60 |
| gtcggagagt | ggcaccagtc | cctgcaggat | caaggccaag | agcttcagca | agttgttgtg | 120 |
| cagtgtagtt | gactcgcgac | ggttgacctt | gccgatcacg | aacatgtggt | gcttgaatct | 180 |
| gttgtacttt | tggatgacct | ggctcacatc | aacgtccttg | atttcgccag | agatccagta | 240 |
| gaactccttg | ttcttcttag | cgatggtcag | cctttcctcg | ttcttgaagg | acaacacgat | 300 |
| gaagttgtga | cccttaacgt | tatcgacgtt | ttgagtcaag | tactgctcaa | cgatgtgcat | 360 |
| gcttccgtct | tccttcttga | ccttcttgag | gttctcggcg | ttgttgttag | aagcgatgtt | 420 |
| gtcgtggtac | ttgtagttgt | tgaagagcag | gttagcgacg | gacgagtact | tgtatgtcag | 480 |
| agtgctcttc | ttgttcacga | tgaggttcag | gttatcaacg | acgtacttgt | tgggaggggtt | 540 |
| gtccgggaat | tggacggact | ccgagtactt | gaggatctgg | gaaacgtatg | gcgagacgaa | 600 |
| gaagttgtta | gaggcggttt | cgatctcgtt | tgattccttg | cggctcagca | tgatgggcaa | 660 |
| agtgaagagg | ttcttgtcct | ggtacatctc | gtacaacttc | gacaagagga | atccacactt | 720 |
| acgctcgccg | agtgattgca | gcaaggtcac | gaaggttgtc | tgagcgtagt | acatatcgag | 780 |
| gttgaagtag | gaggtcagag | cggccttgaa | tgtgtggtgg | acgtccacga | agtgacactt | 840 |
| cttgcagttt | tgagcggcgg | tctcatcgtt | gcagacgtcc | tgtgagtgtg | ggatttcgat | 900 |
| gccagtctcc | ttaaccaggt | tgtagctgat | catgaagcgg | atcttatcga | aggtcacaac | 960 |
| gaacacacgg | ttgtcaacca | tgtagtagtt | gtttgtgtac | tcgtagacca | cgttagagac | 1020 |
| gtacttggcg | aagatgattt | cgaaaggctt | cacctcggac | ttcttaacga | cgaacatgta | 1080 |
| gtaaccggtt | tcagacatgt | gatcggagaa | tctgttcgag | ttgtagtcgt | tatcgtcgaa | 1140 |
| cctcatcagg | taggggggcga | agtcgtttgt | gaagtagtga | gtgatctcct | gggtggaagc | 1200 |
| cactgtacag | atgttagtgt | tgtggttgat | ggtttgttcc | agtgtagcgc | atgactggat | 1260 |
| ggtgctcttc | ttgtacttag | gtctcaactt | gatcttgttg | aattgaccca | caactccctg | 1320 |
| ggagttatcc | aggtactcgt | ccaacttcct | cttggtgcct | gtggccgacg | gctggttgac | 1380 |
| accagcagag | tgttcgaagg | actcggcgtg | gtaagctgag | ctaggagagg | gttgttcgac | 1440 |
| cactggctgt | tcgagtgact | cgctgtagta | ggcagaggac | acagcttcct | ccaggttgtc | 1500 |
| agtggtcttg | agcagacact | ccaccaaatc | gttgtcagtg | agcgagttaa | ctgaggcgag | 1560 |
| gaagttgcta | gcggcagcgg | tttcagagtc | ggagatgaca | gtatcagctc | cgtccgggt | 1620 |
| tgggtggttg | tagtaagaca | agtaatcgtt | aggttgcttg | tcgcagaact | ccgagtatga | 1680 |
| gttgtcgaag | ctagcacgag | agggagtgct | ggcagaggtg | taggaagcgt | tgaagttgat | 1740 |
| ttgagtcatg | gtgacctggt | tgttcacgat | cttatcgcca | cctgtgtcca | cctgcagttg | 1800 |
| ctgggcctca | gcgcaggctg | aagtggcctc | acaggagtag | gggctggaag | cacagttgga | 1860 |
| agtcatgatg | ttttcttgga | cgttcaggac | gtggctggat | gtacggatca | tagatctatc | 1920 |
| tagattcgaa | agcggccgcg | actagtgagc | tcgtcgacgt | aggcctttga | attccgcgcg | 1980 |
| cttcggaccg | ggatccgcgc | ccgatggtgg | gacggtatga | ataatccgga | atatttatag | 2040 |
| gtttttttat | tacaaaactg | ttacgaaaac | agtaaaatac | ttatttattt | gcagatggt | 2100 |
| tatcatttta | attatctcca | tgatctatta | atattccgga | gtataccta | ccgtaaagcg | 2160 |

```
agtttagttt tgaaaaacaa atgacatcat ttgtataatg acatcatccc ctgattgtgt    2220
tttacaagta gaattctatc cgtaaagcga gttcagtttt gaaaacaaat gagtcatacc    2280
taaacacgtt aataatcttc tgatatcagc ttatgactca agttatgagc cgtgtgcaaa    2340
acatgagata agtttatgac atcatccact gatcgtgcgt tacaagtaga attctactcg    2400
taaagccagt tcggttatga gccgtgtgca aaacatgaca tcagcttatg actcatactt    2460
gattgtgttt tacgcgtaga attctactcg taaagcgagt tcggttatga gccgtgtgca    2520
aaacatgaca tcagcttatg agtcataatt aatcgtgcgt tacaagtaga attctactcg    2580
taaagcgagt tgaaggatca tatttagttg cgtttatgag ataagattga aagcacgtgt    2640
aaaatgtttc caaaacatc gattagggtg actgaaggtt acattggggt aggttatggt    2700
taatacgtaa tggtttaaca ccaaaacgat atcatggatt ttatataagg tgtaataata    2760 ttttttaatga gtggacgcgt cgggtcaatg tcctgcctat tgacgtcata acatattagg    2820
tgattatatt aaaaatagtt taaactcaaa tattacttgc aagtttaagt ttcatcataa    2880
tctgatcata agtttcaccc aaacagaaac caaaagcata actatcgaat atctttagct    2940
tcccatgaag aaagattacc gtaaccatca ctaggatttt atacgattgt agaaaataaa    3000
gtattctcag tctcttttca gagcgctata aaaagggtg cattctcggt aagagtacag    3060
ttgaactcac atcgagttaa ctccacgctg caggaccttt aattcaaccc aacacaatat    3120
attatagtta aataagaatt attatcaaat catttgtata ttaattaaaa tactatactg    3180
taaattacat tttatttaca atcactcgac ggatcccccg ggatctcgag atggtgagca    3240
agggcgagga gctgttcacc ggggtggtgc ccatcctggt cgagctggac ggcgacgtaa    3300
acggccacaa gttcagcgtg tccggcgagg gcgagggcga tgccacctac ggcaagctga    3360
ccctgaagtt catctgcacc accggcaagc tgcccgtgcc ctggcccacc ctcgtgacca    3420
ccctgaccta cggcgtgcag tgcttcagcc gctaccccga ccacatgaag cagcacgact    3480
tcttcaagtc cgccatgccc gaaggctacg tccaggagcg caccatcttc ttcaaggacg    3540
acggcaacta caagacccgc gccgaggtga agttcgaggg cgacaccctg gtgaaccgca    3600
tcgagctgaa gggcatcgac ttcaaggagg acggcaacat cctggggcac aagctggagt    3660
acaactacaa cagccacaac gtctatatca tggccgacaa gcagaagaac ggcatcatgg    3720
tgaacttcaa gatccgccac aacatcgagg acggcagcgt gcagctcgcc gaccactacc    3780
agcagaacac ccccatcggc gacggccccg tgctgctgcc cgacaaccac tacctgagca    3840
cccagtccgc cctgagcaaa gaccccaacg agaagcgcga tcacatggtc ctgctggagt    3900
tcgtgaccgc cgccgggatc actctcggca tggacgagct gtacaagtaa                 3950
```

<210> SEQ ID NO 37
<211> LENGTH: 3791
<212> TYPE: DNA
<213> ORGANISM: Artificial Sequence
<220> FEATURE:
<223> OTHER INFORMATION: Recombinant expression cassette

<400> SEQUENCE: 37

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
```

```
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcagacgaa     600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg taggggcga agtcgttgt gaagtagtga gtgatctcct gggtggaagc    1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg ttgttcgac    1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccgggt    1620
tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatc   1920
tagattcgaa agcggccgcg actagtgagc tcgtcgacgt aggcctttga attccgcgcg   1980
cttcggaccg ggatccgcgc ccgatggtgg gacggtatga ataatccgga atatttatag   2040
gttttttat tacaaaactg ttacgaaaac agtaaaatac ttatttattt gcgagatggt    2100
tatcatttta attatctcca tgatctatta atattccgga gtataccttac ccgtaaagcg   2160
agtttagttt tgaaaaacaa atgacatcat ttgtataatg acatcatccc ctgattgtgt   2220
tttacaagta gaattctatc cgtaaagcga gttcagtttt gaaaacaaat gagtcatacc   2280
taaacacgtt aataatcttc tgatatcagc ttatgactca agtttatgagc cgtgtgcaaa   2340
acatgagata agtttatgac atcatccact gatcgtgcgt tacaagtaga attctactcg   2400
taaagccagt tcggttatga gccgtgtgca aaacatgaca tcagcttatg actcatactt   2460
gattgtgttt tacgcgtaga attctactcg taaagcgagt tcggttatga gccgtgtgca   2520
aaacatgaca tcagcttatg agtcataatt aatcgtgcgt tacaagtaga attctactcg   2580
taaagcgagt tgaaggatca tatttagttg cgtttatgag ataagattga aagcacgtgt   2640
```

```
aaaatgtttc cgagctcgtc gacgtaggcc tttgaattcc gcgcgcttcg gaccgggatc    2700
ggtaccaaat tccgttttgc gacgatgcag agttttgaa caggctgctc aaacacatag    2760
atccgtaccc gctcagtcgg atgtattaca atgcagccaa taccatgttt tacacgacta    2820
tggaaaacta tgccgtgtcc aattgcaagt tcaacattga ggattacaat aacatattta    2880
aggtgatgga aaatattagg aaacacagca acaaaaattc aaacgaccaa gacgagttaa    2940
acatatattt gggagttcag tcgtcgaatg caaagcgtaa aaaatattaa taaggtaaaa    3000
attacagcta cataaattac acaatttaaa ctgcagtctg gagatacgct cgagcatgca    3060
agcttgaatt catggtgagc aagggcgagg agctgttcac cggggtggtg cccatcctgg    3120
tcgagctgga cggcgacgta aacggccaca gttcagcgt gtccggcgag gcgagggcg     3180 atgccaccta cggcaagctg accctgaagt tcatctgcac caccggcaag ctgcccgtgc    3240
cctggcccac cctcgtgacc accctgacct acggcgtgca gtgcttcagc cgctaccccg    3300
accacatgaa gcagcacgac ttcttcaagt ccgccatgcc cgaaggctac gtccaggagc    3360
gcaccatctt cttcaaggac gacggcaact acaagacccg cgccgaggtg aagttcgagg    3420
gcgacaccct ggtgaaccgc atcgagctga agggcatcga cttcaaggag gacggcaaca    3480
tcctggggca caagctggag tacaactaca acagccacaa cgtctatatc atggccgaca    3540
agcagaagaa cggcatcatg gtgaacttca agatccgcca caacatcgag gacggcagcg    3600
tgcagctcgc cgaccactac cagcagaaca cccccatcgg cgacggcccc gtgctgctgc    3660
ccgacaacca ctacctgagc acccagtccg ccctgagcaa agaccccaac gagaagcgcg    3720
atcacatggt cctgctggag ttcgtgaccg ccgccgggat cactctcggc atggacgagc    3780
tgtacaagta a                                                        3791

<210> SEQ ID NO 38
<211> LENGTH: 3530
<212> TYPE: DNA
<213> ORGANISM: Artificial Sequence
<220> FEATURE:
<223> OTHER INFORMATION: Recombinant expression cassette

<400> SEQUENCE: 38
ttagttgaac tcgaacttct tgtacttgca gttgagcttt tgctcggcga atgtgatggc      60
gtcggagagt ggcaccagtc cctgcaggat caaggcaag agcttcagca agttgttgtg     120
cagtgtagtt gactcgcgac ggttgacctt gccgatcacg aacatgtggt gcttgaatct    180
gttgtacttt tggatgacct ggctcacatc aacgtccttg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcgagacgaa    600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
```

| | |
|---|---|
| cttgcagttt tgagcggcgg tctcatcgtt gcagacgtcc tgtgagtgtg ggatttcgat | 900 |
| gccagtctcc ttaaccaggt tgtagctgat catgaagcgg atcttatcga aggtcacaac | 960 |
| gaacacacgg ttgtcaacca tgtagtagtt gtttgtgtac tcgtagacca cgttagagac | 1020 |
| gtacttggcg aagatgattt cgaaaggctt cacctcggac ttcttaacga cgaacatgta | 1080 |
| gtaaccggtt tcagacatgt gatcggagaa tctgttcgag ttgtagtcgt tatcgtcgaa | 1140 |
| cctcatcagg taggggcga agtcgtttgt gaagtagtga gtgatctcct gggtggaagc | 1200 |
| cactgtacag atgttagtgt tgtggttgat ggtttgttcc agtgtagcgc atgactggat | 1260 |
| ggtgctcttc ttgtacttag gtctcaactt gatcttgttg aattgaccca caactccctg | 1320 |
| ggagttatcc aggtactcgt ccaacttcct cttggtgcct gtggccgacg gctggttgac | 1380 |
| accagcagag tgttcgaagg actcggcgtg gtaagctgag ctaggagagg gttgttcgac | 1440 |
| cactggctgt tcgagtgact cgctgtagta ggcagaggac acagcttcct ccaggttgtc | 1500 |
| agtggtcttg agcagacact ccaccaaatc gttgtcagtg agcgagttaa ctgaggcgag | 1560 |
| gaagttgcta gcggcagcgg tttcagagtc ggagatgaca gtatcagctc cgtccggggt | 1620 |
| tgggtggttg tagtaagaca agtaatcgtt aggttgcttg tcgcagaact ccgagtatga | 1680 |
| gttgtcgaag ctagcacgag agggagtgct ggcagaggtg taggaagcgt tgaagttgat | 1740 |
| ttgagtcatg gtgacctggt tgttcacgat cttatcgcca cctgtgtcca cctgcagttg | 1800 |
| ctgggcctca gcgcaggctg aagtggcctc acaggagtag ggctggaag cacagttgga | 1860 |
| agtcatgatg ttttcttgga cgttcaggac gtggctggat gtacggatca tagatctatt | 1920 |
| gggtcatcta gattcgaaag cggccgcgac tagtgagctc gtcgacgtag gcctttgaat | 1980 |
| tccgcgcgct tcggaccggg atccgcgccc gatggtggga cggtatgaat aatccggaat | 2040 |
| atttataggt ttttttatta caaaactgtt acgaaaacag taaatactt atttatttgc | 2100 |
| gagatggtta tcattttaat tatctccatg atctattaat attccggagt atacctaccc | 2160 |
| gtaaagcgag tttagttttg aaaaacaaat gacatcattt gtataatgac atcatccccct | 2220 |
| gattgtgttt tacaagtaga attctatccg taaagcgagt tcagttttga aaacaaatga | 2280 |
| gtcataccta aacacgttaa taatcttctg atatcagctt atgactcaag ttatgagccg | 2340 |
| tgtgcaaaac atgagataag tttatgacat catccactga tcgtgcgtta caagtagaat | 2400 |
| tctactcgta aagccagttc ggttatgagc cgtgtgcaaa acatgacatc agcttatgac | 2460 |
| tcatacttga ttgtgttta cgcgtagaat tctactcgta aagcgagttc ggttatgagc | 2520 |
| cgtgtgcaaa acatgacatc agcttatgag tcataattaa tcgtgcgtta caagtagaat | 2580 |
| tctactcgta aagcgagttg aaggatcata tttagttgcg tttatgagat aagattgaaa | 2640 |
| gcacgtgtaa aatgtttccg agctcatacg gaccttttaat tcaacccaac acaatatatt | 2700 |
| atagttaaat aagaattatt atcaaatcat ttgtatatta attaaaatac tatactgtaa | 2760 |
| attacatttt atttcaaatc actcgacctc gagcatgcaa gcttgaattc atggtgagca | 2820 |
| agggcgagga gctgttcacc ggggtggtgc ccatcctggt cgagctggac ggcgacgtaa | 2880 |
| acggccacaa gttcagcgtg tccggcgagg gcgagggcga tgccacctac ggcaagctga | 2940 |
| ccctgaagtt catctgcacc accggcaagc tgcccgtgcc ctggcccacc ctcgtgacca | 3000 |
| ccctgaccta cggcgtgcag tgcttcagcc gctaccccga ccacatgaag cagcacgact | 3060 |
| tcttcaagtc cgccatgccc gaaggctacg tccaggagcg caccatcttc ttcaaggacg | 3120 |
| acggcaacta caagacccgc gccgaggtga agttcgaggg cgacaccctg gtgaaccgca | 3180 |
| tcgagctgaa gggcatcgac ttcaaggagg acggcaacat cctggggcac aagctggagt | 3240 |

-continued

```
acaactacaa cagccacaac gtctatatca tggccgacaa gcagaagaac ggcatcatgg    3300
tgaacttcaa gatccgccac aacatcgagg acggcagcgt gcagctcgcc gaccactacc    3360
agcagaacac ccccatcggc gacggccccg tgctgctgcc cgacaaccac tacctgagca    3420
cccagtccgc cctgagcaaa gaccccaacg agaagcgcga tcacatggtc ctgctggagt    3480
tcgtgaccgc cgccgggatc actctcggca tggacgagct gtacaagtaa               3530
```

<210> SEQ ID NO 39
<211> LENGTH: 3515
<212> TYPE: DNA
<213> ORGANISM: Artificial Sequence
<220> FEATURE:
<223> OTHER INFORMATION: Recombinant expression cassette

<400> SEQUENCE: 39

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgaccct gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
gtcgtggtac ttgtagttgt tgaagagcag gttagcgacg gacgagtact tgtatgtcag     480
agtgctcttc ttgttcacga tgaggttcag gttatcaacg acgtacttgt tgggagggtt     540
gtccgggaat tggacggact ccgagtactt gaggatctgg gaaacgtatg gcagacgaa      600 gaagttgtta gaggcggttt cgatctcgtt tgattccttg cggctcagca tgatgggcaa     660
agtgaagagg ttcttgtcct ggtacatctc gtacaacttc gacaagagga atccacactt     720
acgctcgccg agtgattgca gcaaggtcac gaaggttgtc tgagcgtagt acatatcgag     780
gttgaagtag gaggtcagag cggccttgaa tgtgtggtgg acgtccacga agtgacactt     840
cttgcagttt tgagcggcgg tctcatcgtt gcagacgtcc tgtgagtgtg ggatttcgat     900
gccagtctcc ttaaccaggt tgtagctgat catgaagcgg atcttatcga aggtcacaac     960
gaacacacgg ttgtcaacca tgtagtagtt gtttgtgtac tcgtagacca cgttagagac    1020
gtacttggcg aagatgattt cgaaaggctt cacctcggac ttcttaacga cgaacatgta    1080
gtaaccggtt tcagacatgt gatcggagaa tctgttcgag ttgtagtcgt tatcgtcgaa    1140
cctcatcagg taggggcga agtcgtttgt gaagtagtga gtgatctcct gggtggaagc    1200
cactgtacag atgttagtgt tgtggttgat ggtttgttcc agtgtagcgc atgactggat    1260
ggtgctcttc ttgtacttag gtctcaactt gatcttgttg aattgaccca caactccctg    1320
ggagttatcc aggtactcgt ccaacttcct cttggtgcct gtggccgacg gctggttgac    1380
accagcagag tgttcgaagg actcggcgtg gtaagctgag ctaggagagg ttgttcgac     1440 cactggctgt tcgagtgact cgctgtagta ggcagaggac acagcttcct ccaggttgtc    1500
agtggtcttg agcagacact ccaccaaatc gttgtcagtg agcgagttaa ctgaggcgag    1560
gaagttgcta gcggcagcgg tttcagagtc ggagatgaca gtatcagctc cgtccgggt     1620 tgggtggttg tagtaagaca agtaatcgtt aggttgcttg tcgcagaact ccgagtatga    1680
gttgtcgaag ctagcacgag agggagtgct ggcagaggtg taggaagcgt tgaagttgat    1740
```

```
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg ttttcttgga cgttcaggac gtggctggat gtacggatca tagatccgcg    1920
cccgatggtg ggacggtatg aataatccgg aatatttata ggttttttta ttacaaaact    1980
gttacgaaaa cagtaaaata cttatttatt tgcgagatgg ttatcatttt aattatctcc    2040
atgatctatt aatattccgg agtactgcta cccgtaaagc gagtttagtt ttgaaaaaca    2100
aatgacatca tttgtataat gacatcatcc cctgattgtg ttttacaagt agaattctat    2160
ccgtaaagcg agttcagttt tgaaaacaaa tgagtcatac ctaaacacgt taataatctt    2220
ctgatatcag cttatgactc aagttatgag ccgtgtgcaa acatgagat aagtttatga     2280 catcatccac tgatcgtgcg ttacaagtag aattctactc gtaaagccag ttcggttatg    2340
agccgtgtgc aaaacatgac atcagcttat gactcatact tgattgtgtt ttacgcgtag    2400
aattctactc gtaaagcgag ttcggttatg agccgtgtgc aaaacatgac atcagcttat    2460
gagtcataat taatcgtgcg ttacaagtag aattctactc gtaaagcgag ttgaaggatc    2520
atatttagtt gcgtttatga gataagattg aaagcacgtg taaatgtttt cctccggaat    2580
attaatagat catggagata attaaaatga taaccatctc gcaaataaat aagtatttta   2640
ctgttttcgt aacagttttg taataaaaaa acctataaat attccggatt attcataccg    2700
tcccaccatc gggcgcggga tcccccggga tctcgagcc tggttctaga cagctgatgc     2760
atactagagc ctgcagtctc gacaagcttg aattcatggt gagcaagggc gaggagctgt    2820
tcaccggggt ggtgcccatc ctggtcgagc tggacggcga cgtaaacggc cacaagttca    2880
gcgtgtccgg cgagggcgag ggcgatgcca cctacggcaa gctgaccctg aagttcatct    2940
gcaccaccgg caagctgccc gtgccctggc ccaccctcgt gaccaccctg acctacggcg    3000
tgcagtgctt cagccgctac cccgaccaca tgaagcagca cgacttcttc aagtccgcca    3060
tgcccgaagg ctacgtccag gagcgcacca tcttcttcaa ggacgacggc aactacaaga    3120
cccgcgccga ggtgaagttc gagggcgaca cccctggtgaa ccgcatcgag ctgaagggca   3180
tcgacttcaa ggaggacggc aacatcctgg ggcacaagct ggagtacaac tacaacagcc    3240
acaacgtcta tatcatggcc gacaagcaga agaacggcat catggtgaac ttcaagatcc    3300
gccacaacat cgaggacggc agcgtgcagc tcgccgacca ctaccagcag aacacccca    3360 tcggcgacgg ccccgtgctg ctgcccgaca ccactacct gagcacccag tccgccctga    3420
gcaaagaccc caacgagaag cgcgatcaca tggtcctgct ggagttcgtg accgccgccg    3480
ggatcactct cggcatggac gagctgtaca agtaa                               3515
```

<210> SEQ ID NO 40
<211> LENGTH: 1097
<212> TYPE: DNA
<213> ORGANISM: Artificial Sequence
<220> FEATURE:
<223> OTHER INFORMATION: Recombinant DNA construct fusing the GFP cDNA
      to the p6.9 promoter

<400> SEQUENCE: 40

```
ggtaccaaat tccgttttgc gacgatgcag agttttttgaa caggctgctc aaacacatag     60
atccgtaccc gctcagtcgg atgtattaca atgcagccaa taccatgttt tacacgacta    120
tggaaaacta tgccgtgtcc aattgcaagt tcaacattga ggattacaat aacatattta    180
aggtgatgga aaatattagg aaacacagca acaaaaaatt aaacgaccaa gacgagttaa    240
```

```
acatatattt gggagttcag tcgtcgaatg caaagcgtaa aaaatattaa taaggtaaaa       300
attacagcta cataaattac acaatttaaa ctgcagtctg gagatacgct cgagcatgcg       360
gtaccaagct tgaattcatg gtgagcaagg gcgaggagct gttcaccggg gtggtgccca       420
tcctggtcga gctggacggc gacgtaaacg gccacaagtt cagcgtgtcc ggcgagggcg       480
agggcgatgc cacctacggc aagctgaccc tgaagttcat ctgcaccacc ggcaagctgc       540
ccgtgccctg gcccaccctc gtgaccaccc tgacctacgg cgtgcagtgc ttcagccgct       600
accccgacca catgaagcag cacgacttct tcaagtccgc catgcccgaa ggctacgtcc       660
aggagcgcac catcttcttc aaggacgacg gcaactacaa gacccgcgcc gaggtgaagt       720
tcgagggcga caccctggtg aaccgcatcg agctgaaggg catcgacttc aaggaggacg       780
gcaacatcct ggggcacaag ctggagtaca actacaacag ccacaacgtc tatatcatgg       840
ccgacaagca gaagaacggc atcatggtga acttcaagat ccgccacaac atcgaggacg       900
gcagcgtgca gctcgccgac cactaccagc agaacacccc catcggcgac ggccccgtgc       960
tgctgcccga caaccactac ctgagcaccc agtccgccct gagcaaagac cccaacgaga      1020
agcgcgatca catggtcctg ctggagttcg tgaccgccgc cgggatcact ctcggcatgg      1080
acgagctgta caagtaa                                                     1097

<210> SEQ ID NO 41
<211> LENGTH: 1211
<212> TYPE: DNA
<213> ORGANISM: Artificial Sequence
<220> FEATURE:
<223> OTHER INFORMATION: Recombinant DNA construct fusing the GFP cDNA
      to the pB29 promoter

<400> SEQUENCE: 41
aaaaacatcg attagggtga ctgaaggtta cattggggta ggttatggtt aatacgtaat        60
ggtttaacac caaaacgata tcatggattt tatataaggt gtaataatat ttttaatgag       120
tggacgcgtc gggtcaatgt cctgcctatt gacgtcataa catattaggt gattatatta       180
aaaatagttt aaactcaaat attacttgca agtttaagtt tcatcataat ctgatcataa       240
gtttcaccca aacagaaacc aaaagcataa ctatcgaata tctttagctt cccatgaaga       300
aagattaccg taaccatcac taggattttta tacgattgta gaaataaag tattctcagt       360 ctcttttcag agcgctataa aaggggtgc attctcggta agagtacagt tgaactcaca       420
tcgagttaac tccacgctcg agccatggtg ctagcagctg atgcatagca tgcggtacca       480
agcttgaatt catggtgagc aagggcgagg agctgttcac cggggtggtg cccatcctgg       540
tcgagctgga cggcgacgta aacggccaca gttcagcgt gtccggcgag ggcgagggcg       600
atgccaccta cggcaagctg accctgaagt tcatctgcac caccggcaag ctgcccgtgc       660
cctggcccac cctcgtgacc accctgacct acggcgtgca gtgcttcagc cgctaccccg       720
accacatgaa gcagcacgac ttcttcaagt ccgccatgcc cgaaggctac gtccaggagc       780
gcaccatctt cttcaaggac gacggcaact acaagacccg cgccgaggtg aagttcgagg       840
gcgacaccct ggtgaaccgc atcgagctga agggcatcga cttcaaggag gacggcaaca       900
tcctggggca caagctggag tacaactaca acagccacaa cgtctatatc atggccgaca       960
agcagaagaa cggcatcatg gtgaacttca agatccgcca caacatcgag gacggcagcg      1020
tgcagctcgc cgaccactac cagcagaaca ccccatcgg cgacggcccc gtgctgctgc      1080
ccgacaacca ctacctgagc acccagtccg ccctgagcaa agaccccaac gagaagcgcg      1140
```

```
atcacatggt cctgctggag ttcgtgaccg ccgccgggat cactctcggc atggacgagc   1200
tgtacaagta a                                                        1211
```

<210> SEQ ID NO 42
<211> LENGTH: 865
<212> TYPE: DNA
<213> ORGANISM: Artificial Sequence
<220> FEATURE:
<223> OTHER INFORMATION: Recombinant DNA construct fusing the GFP cDNA to the p10 promoter

<400> SEQUENCE: 42

```
atacggacct ttaattcaac ccaacacaat atattatagt taaataagaa ttattatcaa     60
atcatttgta tattaattaa aatactatac tgtaaattac attttattta caatcactcg    120
acctcgagca tgcaagcttg aattcatggt gagcaagggc gaggagctgt tcaccggggt    180
ggtgcccatc ctggtcgagc tggacggcga cgtaaacggc cacaagttca gcgtgtccgg    240
cgagggcgag ggcgatgcca cctacggcaa gctgaccctg aagttcatct gcaccaccgg    300
caagctgccc gtgccctggc ccaccctcgt gaccaccctg acctacggcg tgcagtgctt    360
cagccgctac cccgaccaca tgaagcagca cgacttcttc aagtccgcca tgcccgaagg    420
ctacgtccag gagcgcacca tcttcttcaa ggacgacggc aactacaaga cccgcgccga    480
ggtgaagttc gagggcgaca ccctggtgaa ccgcatcgag ctgaagggca tcgacttcaa    540
ggaggacggc aacatcctgg ggcacaagct ggagtacaac tacaacagcc acaacgtcta    600
tatcatggcc gacaagcaga agaacggcat catggtgaac ttcaagatcc gccacaacat    660
cgaggacggc agcgtgcagc tcgccgacca ctaccagcag aacaccccca tcggcgacgg    720
ccccgtgctg ctgcccgaca accactacct gagcacccag tccgccctga gcaaagaccc    780
caacgagaag cgcgatcaca tggtcctgct ggagttcgtg accgccgccg ggatcactct    840
cggcatggac gagctgtaca agtaa                                          865
```

<210> SEQ ID NO 43
<211> LENGTH: 387
<212> TYPE: DNA
<213> ORGANISM: Artificial Sequence
<220> FEATURE:
<223> OTHER INFORMATION: Nucleic acid sequence encoding the single domain antibody (VHH) 3B2 from camelids, which is specific for the VP6 protein from rotavirus A

<400> SEQUENCE: 43

```
atggctgatg tgcagctgca ggcgtctggg ggaggtttgg cgcaggctgg ggactctctg     60
acactctcct gtgcagcctc tggacgcacc ttcagtggtt atgtcgtggg ctggttccgc    120
caggctccag ggcggagcg tgagtttgta ggagctatta gatggtcaga agatagcaca     180
tggtatggag actccatgaa gggccgaatt ctcatctcca gaaacaatat caagaacacg    240
gtgaatctgc aaatgttcaa tctaaaacct gaagacacgg ccgtgtacgt ctgtgcagca    300
ggggccgggg atatagtgac tactgagact tcttataatt actggggccg ggggacccag    360
gtcaccgtct cctcacgcgg ccgctaa                                        387
```

<210> SEQ ID NO 44
<211> LENGTH: 128
<212> TYPE: PRT
<213> ORGANISM: Artificial Sequence
<220> FEATURE:
<223> OTHER INFORMATION: Single domain antibody (VHH) 3B2 from camelids, which is specific for the VP6 protein from rotavirus A

<400> SEQUENCE: 44

Met Ala Asp Val Gln Leu Gln Ala Ser Gly Gly Gly Leu Ala Gln Ala
1               5                   10                  15

Gly Asp Ser Leu Thr Leu Ser Cys Ala Ala Ser Gly Arg Thr Phe Ser
            20                  25                  30

Gly Tyr Val Val Gly Trp Phe Arg Gln Ala Pro Gly Ala Glu Arg Glu
        35                  40                  45

Phe Val Gly Ala Ile Arg Trp Ser Glu Asp Ser Thr Trp Tyr Gly Asp
    50                  55                  60

Ser Met Lys Gly Arg Ile Leu Ile Ser Arg Asn Asn Ile Lys Asn Thr
65                  70                  75                  80

Val Asn Leu Gln Met Phe Asn Leu Lys Pro Glu Asp Thr Ala Val Tyr
                85                  90                  95

Val Cys Ala Ala Gly Ala Gly Asp Ile Val Thr Thr Glu Thr Ser Tyr
            100                 105                 110

Asn Tyr Trp Gly Arg Gly Thr Gln Val Thr Val Ser Ser Arg Gly Arg
        115                 120                 125

<210> SEQ ID NO 45
<211> LENGTH: 381
<212> TYPE: DNA
<213> ORGANISM: Artificial Sequence
<220> FEATURE:
<223> OTHER INFORMATION: Nucleic acid sequence encoding the single domain antibody (VHH) 2KD1 from camelids, which is specific for the VP6 protein from rotavirus A

<400> SEQUENCE: 45
atggctgatg tgcagctgca ggcgtctggg ggaggatttg tgcagcctgg agattctctg 60
agtctctcct gtgcagcctc tggaggcacc tttagtagct attccattgg ctggttccgc 120
cagggtccag ggaaggagcg tgagttcgtg gctactatca gttcgagtga tagtccgtgg 180
tatggagagc ccgcgaaggg ccgattcacc gtcgccagag ttaacgccaa gaatacggcg 240
tatctgcact tgaacaggtt gaaacctgag gacacggcca cttattattg tgcagccggt 300
agtgtacaac acatggcgaa tgagaatgag tatgtctatt ggggccaggg gacccaggtc 360
accgtctcca gcggccgcta a 381

<210> SEQ ID NO 46
<211> LENGTH: 126
<212> TYPE: PRT
<213> ORGANISM: Artificial Sequence
<220> FEATURE:
<223> OTHER INFORMATION: Single domain antibody (VHH) 2KD1 from camelids, which is specific for the VP6 protein from rotavirus A

<400> SEQUENCE: 46

Met Ala Asp Val Gln Leu Gln Ala Ser Gly Gly Gly Phe Val Gln Pro
1               5                   10                  15

Gly Asp Ser Leu Ser Leu Ser Cys Ala Ala Ser Gly Gly Thr Phe Ser
            20                  25                  30

Ser Tyr Ser Ile Gly Trp Phe Arg Gln Gly Pro Gly Lys Glu Arg Glu
        35                  40                  45

Phe Val Ala Thr Ile Ser Ser Ser Asp Ser Pro Trp Tyr Gly Glu Pro
    50                  55                  60

Ala Lys Gly Arg Phe Thr Val Ala Arg Val Asn Ala Lys Asn Thr Ala
65                  70                  75                  80

Tyr Leu His Leu Asn Arg Leu Lys Pro Glu Asp Thr Ala Thr Tyr Tyr
            85                  90                  95

Cys Ala Ala Gly Ser Val Gln His Met Ala Asn Glu Asn Glu Tyr Val
        100                 105                 110

Tyr Trp Gly Gln Gly Thr Gln Val Thr Val Ser Ser Gly Arg
    115                 120                 125

<210> SEQ ID NO 47
<211> LENGTH: 1518
<212> TYPE: DNA
<213> ORGANISM: Human papillomavirus type 16

<400> SEQUENCE: 47

```
atgtctcttt ggctgcctag cgaggccact gtctacttgc ctcctgtccc agtatctaaa      60
gttgtaagca cggatgaata tgttgcacgc acaaacatat attatcatgc aggaacatcc     120
agactacttg cagttggaca tccctatttt cctattaaaa acctaacaa taacaaaata     180
ttagttccta agtatcagg attacaatac agggtattta gaatatattt acctgacccc     240
aataagtttg gttttcctga cacctcattt tacaatccag atacacagcg ctggtttgg     300
gcctgtgtag gtgttgaggt aggccgtggt cagccattag gtgtgggcat tagtggccat     360
cctttattaa ataaattgga tgacacagaa atgctagtg cttatgcagc aaatgcaggt     420
gtggataata gagaatgtat atctatggat acaaacaaa cacaattgtg tttaattggt     480
tgcaaaccac ctataggga acactgggc aaaggatccc catgtaacaa tgttgcagta     540
aatccaggtg attgtccacc attagagtta ataaacacag ttattcagga tggtgatatg     600
gttgataccg gctttggtgc tatggacttt actacattac aggctaacaa agtgaagtt     660
ccactggata tttgtacgtc tatttgcaaa tatccagatt atattaaaat ggtgtcagaa     720
ccatatggcg acagcttatt ttttatttta cgaagggaac aaatgtttgt tagacattta     780
tttaataggg ctggtgctgt tggtgaaaat gtaccagacg atttatacat taaaggctct     840
gggtctactg caaatttagc cagttcaaat tattttccta cacctagtgg ttctatggtt     900
acctctgatg cccaaatatt taataaacca tattggttac aacgagcaca gggccacaat     960
aatggtattt gttggggtaa ccaactattt gttactgttg ttgatactac acgcagtaca    1020
aatatgtcat tatgtgctgc catatctact tcagaaacta catataaaaa tactaacttt    1080
aaagagtacc tacgacatgg ggaggaatat gatttacagt ttatttttca actgtgcaaa    1140
ataaccttaa ctgcagacgt tatgacatac atacattcta tgaattccac tattttggag    1200
gactggaatt ttggtttaca acctcccca ggaggcacac tagaagatac ttataggttt    1260
gtaacatccc aggcaattgc ttgtcaaaaa catacacctc cagcacctaa gaagatccc    1320
cttaaaaaat atactttttg ggaagtaaat ttaaagaaa gttttctgc agacctagat    1380
cagtttcctt taggacgcaa attttactaa caagcaggat ttaaggccaa accaaaattt    1440
acattaggaa aacgaaaagc tacacccacc acctcatcta cctctacaac tgctaaacgc    1500
aaaaaacgta agctgtaa                                                  1518
```

<210> SEQ ID NO 48
<211> LENGTH: 505
<212> TYPE: PRT
<213> ORGANISM: Human papillomavirus type 16

<400> SEQUENCE: 48

Met Ser Leu Trp Leu Pro Ser Glu Ala Thr Val Tyr Leu Pro Pro Val
1               5                   10                  15

```
Pro Val Ser Lys Val Ser Thr Asp Glu Tyr Val Ala Arg Thr Asn
         20              25              30

Ile Tyr Tyr His Ala Gly Thr Ser Arg Leu Leu Ala Val Gly His Pro
         35              40              45

Tyr Phe Pro Ile Lys Lys Pro Asn Asn Asn Lys Ile Leu Val Pro Lys
 50              55              60

Val Ser Gly Leu Gln Tyr Arg Val Phe Arg Ile Tyr Leu Pro Asp Pro
 65              70              75              80

Asn Lys Phe Gly Phe Pro Asp Thr Ser Phe Tyr Asn Pro Asp Thr Gln
             85              90              95

Arg Leu Val Trp Ala Cys Val Gly Val Glu Val Gly Arg Gly Gln Pro
             100             105             110

Leu Gly Val Gly Ile Ser Gly His Pro Leu Leu Asn Lys Leu Asp Asp
             115             120             125

Thr Glu Asn Ala Ser Ala Tyr Ala Ala Asn Ala Gly Val Asp Asn Arg
 130             135             140

Glu Cys Ile Ser Met Asp Tyr Lys Gln Thr Gln Leu Cys Leu Ile Gly
145             150             155             160

Cys Lys Pro Pro Ile Gly Glu His Trp Gly Lys Gly Ser Pro Cys Asn
                 165             170             175

Asn Val Ala Val Asn Pro Gly Asp Cys Pro Pro Leu Glu Leu Ile Asn
             180             185             190

Thr Val Ile Gln Asp Gly Asp Met Val Asp Thr Gly Phe Gly Ala Met
             195             200             205

Asp Phe Thr Thr Leu Gln Ala Asn Lys Ser Glu Val Pro Leu Asp Ile
         210             215             220

Cys Thr Ser Ile Cys Lys Tyr Pro Asp Tyr Ile Lys Met Val Ser Glu
225             230             235             240

Pro Tyr Gly Asp Ser Leu Phe Phe Tyr Leu Arg Arg Glu Gln Met Phe
                 245             250             255

Val Arg His Leu Phe Asn Arg Ala Gly Ala Val Gly Glu Asn Val Pro
             260             265             270

Asp Asp Leu Tyr Ile Lys Gly Ser Gly Ser Thr Ala Asn Leu Ala Ser
         275             280             285

Ser Asn Tyr Phe Pro Thr Pro Ser Gly Ser Met Val Thr Ser Asp Ala
 290             295             300

Gln Ile Phe Asn Lys Pro Tyr Trp Leu Gln Arg Ala Gln Gly His Asn
305             310             315             320

Asn Gly Ile Cys Trp Gly Asn Gln Leu Phe Val Thr Val Val Asp Thr
                 325             330             335

Thr Arg Ser Thr Asn Met Ser Leu Cys Ala Ala Ile Ser Thr Ser Glu
             340             345             350

Thr Thr Tyr Lys Asn Thr Asn Phe Lys Glu Tyr Leu Arg His Gly Glu
             355             360             365

Glu Tyr Asp Leu Gln Phe Ile Phe Gln Leu Cys Lys Ile Thr Leu Thr
         370             375             380

Ala Asp Val Met Thr Tyr Ile His Ser Met Asn Ser Thr Ile Leu Glu
385             390             395             400

Asp Trp Asn Phe Gly Leu Gln Pro Pro Pro Gly Gly Thr Leu Glu Asp
                 405             410             415

Thr Tyr Arg Phe Val Thr Ser Gln Ala Ile Ala Cys Gln Lys His Thr
             420             425             430
```

```
Pro Pro Ala Pro Lys Glu Asp Pro Leu Lys Lys Tyr Thr Phe Trp Glu
            435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Phe Lys Ala Lys Pro Lys Phe
465                 470                 475                 480

Thr Leu Gly Lys Arg Lys Ala Thr Pro Thr Thr Ser Ser Thr Ser Thr
                485                 490                 495

Thr Ala Lys Arg Lys Lys Arg Lys Leu
            500                 505

<210> SEQ ID NO 49
<211> LENGTH: 2133
<212> TYPE: DNA
<213> ORGANISM: Rabbit hemorrhagic disease virus

<400> SEQUENCE: 49
```

| | | | | | |
|---|---|---|---|---|---|
| atggagggca | aagcccgcac | agcgccgcaa | ggcgaagcag | caggcactgc | caccacagca | 60 |
| tcagtccctg | gaaccacaac | cgatggcatg | accccggcg | ttgtggccac | taccagcgtg | 120 |
| gtcactgcag | agaattcatc | cgcatcgatt | gcaacggcag | ggattggcgg | accaccccaa | 180 |
| caggtggacc | aacaagagac | atggagaacg | aactttattt | ataatgacgt | tttcacttgg | 240 |
| tcagtcgcgg | atgcccctgg | cagcatactt | tacaccgttc | aacattctcc | acagaacaac | 300 |
| ccattcacag | ccgtgctgag | ccagatgtat | gctggctggg | ctggtggcat | gcagtttcgc | 360 |
| ttcatagttg | ccggatcggg | tgtgtttggt | gggcggttgg | ttgcggccgt | gataccaccg | 420 |
| ggcatcgaga | ttggaccagg | gctggaggtc | aggcaattcc | cccatgttgt | catcgacgct | 480 |
| cgttcacttg | aacctgtcac | catcaccatg | ccagacttgc | gtcccaacat | gtaccatcca | 540 |
| actggtgacc | ctggccttgt | tcccacacta | gtccttagtg | tttataacaa | cctcatcaac | 600 |
| ccgtttggtg | ggtccaccag | cgcaatccag | gtgacagtgg | aaacaaggcc | aagtgaagat | 660 |
| tttgagttcg | tgatgattcg | agcccctcc | agcaagactg | ttgactcaat | tcacccgca | 720 |
| ggcctcctca | cgaccccagt | cctcactggg | gttggcaatg | acaacaggtg | gaatggccaa | 780 |
| atagtgggac | tgcaaccagt | aacctggaggg | ttctctacgt | gcaacaggca | ttggaacttg | 840 |
| aatggcagca | catatggctg | gtcaagcccc | cggtttgccg | acattgacca | tcgaagaggc | 900 |
| agtgcaagtt | accctggatc | caacgcaacc | aacgtgcttc | agttttggta | tgccaatgct | 960 |
| gggtctgcaa | tcgacaatcc | catctcccag | gttgcaccag | acggctttcc | tgatatgtcg | 1020 |
| ttcgtgccct | taacggccc | tggcattcca | gccgcgggt | gggtcggatt | tggtgcaatc | 1080 |
| tggaacagta | acagcggtgc | ccccaacgtt | acgactgtgc | aggcttatga | gttaggtttt | 1140 |
| gccactgggg | caccaggcaa | cctccagccc | accaccaaca | cttcaggttc | acagactgtc | 1200 |
| gccaagtcca | tatatgccgt | ggtaactggc | acagcccaaa | accccgccgg | attgtttgtg | 1260 |
| atggcctcgg | tgttatctc | cacccccaagt | gccaacgcca | tcatatacac | gcccaacca | 1320 |
| gacagaattg | taaccacacc | cggcactcct | gccgctgcac | ctgtgggtaa | gaacacaccc | 1380 |
| atcatgttcg | cgtctgtcgt | caggcgcacc | ggtgacgtca | acgccacagc | tgggtcagct | 1440 |
| aacgggaccc | agtacggcac | aggctctcaa | ccactgccag | taacaattgg | actttcgctc | 1500 |
| aacaactact | cgtcagcact | tatgcccgga | cagtttttcg | tttggcagtt | aacctttgca | 1560 |
| tctggtttca | tggagattgg | tttaagtgtg | gacgggtatt | tttatgcagg | aacaggagcc | 1620 |
| tcaaccacac | tcattgactt | gactgaactc | attgacgtac | gccctgtggg | acccaggcca | 1680 |

-continued

```
tccaagagca cactcgtgtt caacctgggg ggcacagcca atggctttc ttatgtctga   1740 attcatcgga ctgggacttg caggtgccag cgttttgagc aatgcattgc tccgcaggca   1800
agagctgcaa ctacaaagac aagctttgga gaatgggttg gttttgaaag ccgaccaatt   1860
aggtaggtta ggttttaatc caaatgaagt taagaatgtg attgtaggta atagttttag   1920
tagtaatgtt agattaagta atatgcataa tgatgctagt gtagttaatg cttataatgt   1980
gtataatcct gccagcaatg gcatcagaaa gaaaattaag agtttgaata atagtgttaa   2040
gatttataac accactgggg agtccagtgt ttaatttgat tttattggtt ttgaaatttg   2100
gtttaattgg gtttatagtt taaagtaagc tat                                2133
```

<210> SEQ ID NO 50
<211> LENGTH: 579
<212> TYPE: PRT
<213> ORGANISM: Rabbit hemorrhagic disease virus

<400> SEQUENCE: 50

```
Met Glu Gly Lys Ala Arg Thr Ala Pro Gln Gly Glu Ala Ala Gly Thr
1               5                   10                  15

Ala Thr Thr Ala Ser Val Pro Gly Thr Thr Thr Asp Gly Met Asp Pro
            20                  25                  30

Gly Val Val Ala Thr Thr Ser Val Val Thr Ala Glu Asn Ser Ser Ala
        35                  40                  45

Ser Ile Ala Thr Ala Gly Ile Gly Gly Pro Pro Gln Gln Val Asp Gln
    50                  55                  60

Gln Glu Thr Trp Arg Thr Asn Phe Tyr Tyr Asn Asp Val Phe Thr Trp
65                  70                  75                  80

Ser Val Ala Asp Ala Pro Gly Ser Ile Leu Tyr Thr Val Gln His Ser
                85                  90                  95

Pro Gln Asn Asn Pro Phe Thr Ala Val Leu Ser Gln Met Tyr Ala Gly
            100                 105                 110

Trp Ala Gly Gly Met Gln Phe Arg Phe Ile Val Ala Gly Ile Gly Val
        115                 120                 125

Phe Gly Gly Arg Leu Val Ala Ala Val Ile Pro Pro Gly Ile Glu Ile
    130                 135                 140

Gly Pro Gly Leu Glu Val Arg Gln Phe Pro His Val Val Ile Asp Ala
145                 150                 155                 160

Arg Ser Leu Glu Pro Val Thr Ile Thr Met Pro Asp Leu Arg Pro Asn
                165                 170                 175

Met Tyr His Pro Thr Gly Asp Pro Gly Leu Val Pro Thr Leu Val Leu
            180                 185                 190

Ser Val Tyr Asn Asn Leu Ile Asn Pro Phe Gly Gly Ser Thr Ser Ala
        195                 200                 205

Ile Gln Val Thr Val Glu Thr Arg Pro Ser Glu Asp Phe Glu Phe Val
    210                 215                 220

Met Ile Arg Ala Pro Ser Ser Lys Thr Val Asp Ser Ile Ser Pro Ala
225                 230                 235                 240

Gly Leu Leu Thr Thr Pro Val Leu Thr Gly Val Gly Asn Asp Asn Arg
                245                 250                 255

Trp Asn Gly Gln Ile Val Gly Leu Gln Pro Val Pro Gly Gly Phe Ser
            260                 265                 270

Thr Cys Asn Arg His Trp Asn Leu Asn Gly Ser Thr Tyr Gly Trp Ser
        275                 280                 285

Ser Pro Arg Phe Gly Asp Ile Gly His Arg Arg Gly Ser Ala Ser Tyr
```

|   |   |   | 290 |   |   |   | 295 |   |   |   | 300 |   |   |   |
|---|---|---|---|---|---|---|---|---|---|---|---|---|---|---|

Pro Gly Asn Asn Ala Thr Asn Val Leu Gln Phe Trp Tyr Ala Asn Ala
305                 310                 315                 320

Gly Ser Ala Ile Asp Asn Pro Ile Ser Gln Val Ala Pro Asp Gly Phe
            325                 330                 335

Pro Asp Met Ser Phe Val Pro Phe Asn Gly Pro Gly Ile Pro Ala Ala
            340                 345                 350

Gly Trp Val Gly Phe Gly Ala Ile Trp Asn Ser Asn Ser Gly Ala Pro
            355                 360                 365

Asn Val Thr Thr Val Gln Ala Tyr Glu Leu Gly Phe Ala Thr Gly Ala
            370                 375                 380

Pro Gly Asn Leu Gln Pro Thr Thr Asn Thr Ser Gly Ser Gln Thr Val
385                 390                 395                 400

Ala Lys Ser Ile Tyr Ala Val Val Thr Gly Thr Ala Gln Asn Pro Ala
            405                 410                 415

Gly Leu Phe Val Met Ala Ser Gly Val Ile Ser Thr Pro Ser Ala Asn
            420                 425                 430

Ala Ile Thr Tyr Thr Pro Gln Pro Asp Arg Ile Val Thr Thr Pro Gly
            435                 440                 445

Thr Pro Ala Ala Ala Pro Val Gly Lys Asn Thr Pro Ile Met Phe Ala
450                 455                 460

Ser Val Val Arg Arg Thr Gly Asp Val Asn Ala Thr Ala Gly Ser Ala
465                 470                 475                 480

Asn Gly Thr Gln Tyr Gly Thr Gly Ser Gln Pro Leu Pro Val Thr Ile
            485                 490                 495

Gly Leu Ser Leu Asn Asn Tyr Ser Ser Ala Leu Met Pro Gly Gln Phe
            500                 505                 510

Phe Val Trp Gln Leu Thr Phe Ala Ser Gly Phe Met Glu Ile Gly Leu
            515                 520                 525

Ser Val Asp Gly Tyr Phe Tyr Ala Gly Thr Gly Ala Ser Thr Thr Leu
            530                 535                 540

Ile Asp Leu Thr Glu Leu Ile Asp Val Arg Pro Val Gly Pro Arg Pro
545                 550                 555                 560

Ser Lys Ser Thr Leu Val Phe Asn Leu Gly Thr Ala Asn Gly Phe
            565                 570                 575

Ser Tyr Val

<210> SEQ ID NO 51
<211> LENGTH: 4550
<212> TYPE: DNA
<213> ORGANISM: Artificial Sequence
<220> FEATURE:
<223> OTHER INFORMATION: Recombinant expression cassette

<400> SEQUENCE: 51

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
gttgtacttt tggatgacct ggctcacatc aacgtccttg atttcgccag agatccagta     240
gaactccttg ttcttcttag cgatggtcag cctttcctcg ttcttgaagg acaacacgat     300
gaagttgtga cccttaacgt tatcgacgtt ttgagtcaag tactgctcaa cgatgtgcat     360
gcttccgtct tccttcttga ccttcttgag gttctcggcg ttgttgttag aagcgatgtt     420
```

```
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcgagacgaa    600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg taggggcga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg gttgttcgac   1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccggggt   1620
tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatc   1920
tagattcgaa agcggccgcg actagtgagc tcgtcgacgt aggcctttga attccgcgcg   1980
cttcggaccg ggatccgcgc ccgatggtgg gacggtatga ataatccgga atatttatag   2040 gttttttat tacaaaactg ttacgaaaac agtaaaatac ttatttattt gcgagatggt   2100
tatcatttta attatctcca tgatctatta atattccgga gtatacctac ccgtaaagcg   2160
agtttagttt tgaaaaacaa atgacatcat ttgtataatg acatcatccc ctgattgtgt   2220
tttacaagta gaattctatc cgtaaagcga gttcagtttt gaaaacaaat gagtcatacc   2280
taaacacgtt aataatcttc tgatatcagc ttatgactca agttatgagc cgtgtgcaaa   2340
acatgagata agtttatgac atcatccact gatcgtgcgt tacaagtaga attctactcg   2400
taaagccagt tcggttatga gccgtgtgca aaacatgaca tcagcttatg actcatactt   2460
gattgtgttt tacgcgtaga attctactcg taaagcgagt tcggttatga gccgtgtgca   2520
aaacatgaca tcagcttatg agtcataatt aatcgtgcgt tacaagtaga attctactcg   2580
taaagcgagt tgaaggatca tatttagttg cgtttatgag ataagattga agcacgtgt   2640 aaaatgtttc cgagctcgtc gacgtaggcc tttgaattcc gcgcgcttcg gaccgggatc   2700
ggtaccaaat tccgtttttgc gacgatgcag agttttttgaa caggctgctc aaacacatag   2760
atccgtaccc gctcagtcgg atgtattaca atgcagccaa taccatgttt tacacgacta   2820
```

```
tggaaaacta tgccgtgtcc aattgcaagt tcaacattga ggattacaat aacatattta      2880
aggtgatgga aaatattagg aaacacagca acaaaaattc aaacgaccaa gacgagttaa      2940
acatatattt gggagttcag tcgtcgaatg caaagcgtaa aaaatattaa taaggtaaaa      3000
attacagcta cataaattac acaatttaaa ctgcagtctg gagatacgga cctttaattc      3060
aacccaacac aatatattat agttaaataa gaattattat caaatcattt gtatattaat      3120
taaaatacta tactgtaaat tacattttat ttacaatcac tcgacctcga gatgacgtat      3180
ccaaggaggc gtttccgcag acgaagacac cgcccccgca gccatcttgg ccagatcctc      3240
cgccgccgcc cctggctcgt ccaccccgc  caccgttacc gctggagaag gaaaaatggc      3300
atcttcaaca cccgcctctc ccgcaccttc ggatatactg tcaaggctac cacagtcaca      3360
acgccctcct gggcggtgga catgatgaga tttaatatta cgactttgt  tccccgggga      3420 gggggggacca acaaaatctc tatacccttt gaatactaca gaataagaaa ggttaaggtt      3480
gaattctggc cctgctcccc aatcacccag ggtgacaggg gagtgggctc cactgctgtt      3540
attctagatg ataactttgt aacaaaggcc acagccctaa cctatgaccc ctatgtaaac      3600
tactcctccc gccatacaat ccccaaccc  ttctcctacc actccgtta  cttcacaccc      3660 aaacctgtac tggatagaac tattgattac ttccagccaa caacaaaaa  aaatcagctt      3720 tggctgaggc tacaaacctc tgcaaatgta gaccacgtag gcctcggcac tgcgttcgaa      3780
aacagtaaat acgaccagga ctacaatatc cgtgtaacca tgtatgtaca attcagagaa      3840
tttaatctta aagaccccc  acttaaaccc taaccatgga agcttatgaa tcgttttta     3900 aataacaaat caattgtttt ataatattcg tacgattctt tgattatgta ataaaatgtg      3960
atcattagga agattacgaa aaatataaaa aatatgagtt ctgtgtgtat aacaaatgct      4020
gtaaacgcca caattgtgtt tgttgcaaat aaacccatga ttatttgatt aaaattgttg      4080 tttttctttgt tcatagacaa tagtgtgttt tgcctaaacg tgtactgcat aaactccatg      4140
cgagtgtata gcgagctagt ggctaacgct tgccccacca agtagattc  gtcaaaatcc      4200 tcaatttcat caccctcctc caagtttaac atttggccgt cggaattaac ttctaaagat      4260
gccacataat ctaataaatg aaatagagat tcaaacgtgg cgtcatcgtc cgtttcgacc      4320
atttccgaaa agaactcggg cataaactct atgatttctc tggacgtggt gttgtcgaaa      4380
ctctcaaagt acgcagtcag gaacgtgcgc gacatgtcgt cgggaaactc gcgcggaaac      4440
atgttgttgt aaccgaacgg gtcccatagc gccaaaacca aatctgccag cgtcaataga      4500
atgagcacga tgccgacaat ggagctggct tggatagcga ttcgagttaa                 4550
```

<210> SEQ ID NO 52
<211> LENGTH: 5366
<212> TYPE: DNA
<213> ORGANISM: Artificial Sequence
<220> FEATURE:
<223> OTHER INFORMATION: Recombinant expression cassette

<400> SEQUENCE: 52

```
ttagttgaac tcgaacttct tgtacttgca gttgagcttt tgctcggcga atgtgatggc        60
gtcggagagt ggcaccagtc cctgcaggat caaggccaag agcttcagca agttgttgtg       120
cagtgtagtt gactcgcgac ggttgacctt gccgatcacg aacatgtggt gcttgaatct       180
gttgtacttt tggatgacct ggctcacatc aacgtccttg atttcgccag agatccagta       240
gaactccttg ttcttcttag cgatggtcag cctttcctcg ttcttgaagg acaacacgat       300
```

```
gaagttgtga cccttaacgt tatcgacgtt ttgagtcaag tactgctcaa cgatgtgcat      360
gcttccgtct tccttcttga cccttcttgag gttctcggcg ttgttgttag aagcgatgtt      420
gtcgtggtac ttgtagttgt tgaagagcag gttagcgacg gacgagtact tgtatgtcag      480
agtgctcttc ttgttcacga tgaggttcag gttatcaacg acgtacttgt tgggagggtt      540
gtccgggaat tggacggact ccgagtactt gaggatctgg gaaacgtatg gcgagacgaa      600
gaagttgtta gaggcggttt cgatctcgtt tgattccttg cggctcagca tgatgggcaa      660
agtgaagagg ttcttgtcct ggtacatctc gtacaacttc gacaagagga atccacactt      720
acgctcgccg agtgattgca gcaaggtcac gaaggttgtc tgagcgtagt acatatcgag      780
gttgaagtag gaggtcagag cggccttgaa tgtgtggtgg acgtccacga agtgacactt      840
cttgcagttt tgagcggcgg tctcatcgtt gcagacgtcc tgtgagtgtg ggatttcgat      900
gccagtctcc ttaaccaggt tgtagctgat catgaagcgg atcttatcga aggtcacaac      960
gaacacacgg ttgtcaacca tgtagtagtt gtttgtgtac tcgtagacca cgttagagac     1020
gtacttggcg aagatgattt cgaaaggctt cacctcggac ttcttaacga cgaacatgta     1080
gtaaccggtt tcagacatgt gatcggagaa tctgttcgag ttgtagtcgt tatcgtcgaa     1140
cctcatcagg taggggcga gtcgtttgt gaagtagtga gtgatctcct gggtggaagc     1200
cactgtacag atgttagtgt tgtggttgat ggtttgttcc agtgtagcgc atgactggat     1260
ggtgctcttc ttgtacttag gtctcaactt gatcttgttg aattgaccca caactccctg     1320
ggagttatcc aggtactcgt ccaacttcct cttggtgcct gtggccgacg gctggttgac     1380
accagcagag tgttcgaagg actcggcgtg gtaagctgag ctaggagagg gttgttcgac     1440
cactggctgt tcgagtgact cgctgtagta ggcagaggac acagcttcct ccaggttgtc     1500
agtggtcttg agcagacact ccaccaaatc gttgtcagtg agcgagttaa ctgaggcgag     1560
gaagttgcta gcggcagcgg tttcagagtc ggagatgaca gtatcagctc cgtccggggt     1620
tgggtggttg tagtaagaca agtaatcgtt aggttgcttg tcgcagaact ccgagtatga     1680
gttgtcgaag ctagcacgag agggagtgct ggcagaggtg taggaagcgt tgaagttgat     1740
ttgagtcatg gtgacctggt tgttcacgat cttatcgcca cctgtgtcca cctgcagttg     1800
ctgggcctca gcgcaggctg aagtggcctc acaggagtag gggctggaag cacagttgga     1860
agtcatgatg ttttcttgga cgttcaggac gtggctggat gtacggatca tagatctatc     1920
tagattcgaa agcggccgcg actagtgagc tcgtcgacgt aggcctttga attccgcgcg     1980
cttcggaccg ggatccgcgc ccgatggtgg gacggtatga ataatccgga atatttatag     2040 gttttttta tacaaaactg ttacgaaaac agtaaaatac ttatttattt gcgagatggt     2100
tatcatttta attatctcca tgatctatta atattccgga gtatacctac ccgtaaagcg     2160
agtttagttt tgaaaaacaa atgacatcat ttgtataatg acatcatccc ctgattgtgt     2220
tttacaagta gaattctatc cgtaaagcga gttcagtttt gaaaacaaat gagtcatacc     2280
taaacacgtt aataatcttc tgatatcagc ttatgactca agttatgagc cgtgtgcaaa     2340
acatgagata agtttatgac atcatccact gatcgtgcgt tacaagtaga attctactcg     2400
taaagccagt tcggttatga gccgtgtgca aaacatgaca tcagcttatg actcatactt     2460
gattgtgttt tacgcgtaga attctactcg taaagcgagt tcggttatga gccgtgtgca     2520
aaacatgaca tcagcttatg agtcataatt aatcgtgcgt tacaagtaga attctactcg     2580
taaagcgagt tgaaggatca tatttagttg cgttttatgag ataagattga aagcacgtgt     2640
aaaatgtttc cgagctcgtc gacgtaggcc tttgaattcc gcgcgcttcg gaccgggatc     2700
```

```
ggtaccaaat tccgttttgc gacgatgcag agtttttgaa caggctgctc aaacacatag   2760
atccgtaccc gctcagtcgg atgtattaca atgcagccaa taccatgttt tacacgacta   2820
tggaaaacta tgccgtgtcc aattgcaagt tcaacattga ggattacaat aacatattta   2880
aggtgatgga aaatattagg aaacacagca acaaaaattc aaacgaccaa gacgagttaa   2940
acatatattt gggagttcag tcgtcgaatg caaagcgtaa aaaatattaa taaggtaaaa   3000
attacagcta cataaattac acaatttaaa ctgcagtctg gagatacgga cctttaattc   3060
aacccaacac aatatattat agttaaataa gaattattat caaatcattt gtatattaat   3120
taaaatacta tactgtaaat tacattttat ttacaatcac tcgacctcga gatgtctctt   3180
tggctgccta gcgaggccac tgtctacttg cctcctgtcc cagtatctaa agttgtaagc   3240
acggatgaat atgttgcacg cacaaacata tattatcatg caggaacatc cagactactt   3300
gcagttggac atccctattt tcctattaaa aaacctaaca ataacaaaat attagttcct   3360
aaagtatcag gattacaata cagggtattt agaatatatt tacctgaccc caataagttt   3420
ggttttcctg acacctcatt ttacaatcca gatacacagc ggctggtttg ggcctgtgta   3480
ggtgttgagg taggccgtgg tcagccatta ggtgtgggca ttagtggcca tcctttatta   3540
aataaattgg atgacacaga aaatgctagt gcttatgcag caaatgcagg tgtggataat   3600
agagaatgta tatctatgga ttacaaacaa acacaattgt gtttaattgg ttgcaaacca   3660
cctataggg aacactgggg caaaggatcc ccatgtaaca atgttgcagt aaatccaggt   3720
gattgtccac cattagagtt aataaacaca gttattcagg atggtgatat ggttgatacc   3780
ggctttggtg ctatggactt tactacatta caggctaaca aaagtgaagt tccactggat   3840
atttgtacgt ctatttgcaa atatccagat tatattaaaa tggtgtcaga accatatggc   3900
gacagcttat ttttttattt acgaagggaa caatgtttg ttagacattt atttaatagg   3960
gctggtgctg ttggtgaaaa tgtaccagac gatttataca ttaaaggctc tgggtctact   4020
gcaaatttag ccagttcaaa ttattttcct acacctagtg gttctatggt tacctctgat   4080
gcccaaatat ttaataaacc atattggtta caacgagcac agggccacaa taatggtatt   4140
tgttggggta accaactatt tgttactgtt gttgatacta cacgcagtac aaaatatgtca   4200
ttatgtgctg ccatatctac ttcagaaact acatataaaa atactaactt taaagagtac   4260
ctacgacatg gggaggaata tgatttacag tttattttc aactgtgcaa ataaccttaa   4320
actgcagacg ttatgacata catacattct atgaattcca ctatttggaa ggactggaat   4380
tttggtttac aacctcccc aggaggcaca ctagaagata cttataggtt tgtaacatcc   4440
caggcaattg cttgtcaaaa acatacacct ccagcaccta agaagatcc ccttaaaaaa   4500
tatactttt gggaagtaaa tttaaaagaa aagttttctg cagacctaga tcagtttcct   4560
ttaggacgca aattttact acaagcagga tttaaggcca aaccaaaatt tacattagga   4620
aaacgaaaag ctacacccac cacctcatct acctctacaa ctgctaaacg caaaaaacgt   4680
aagctgtaac catggaagct tatgaatcgt ttttaaaata acaaatcaat tgttttataa   4740
tattcgtacg attctttgat tatgtaataa aatgtgatca ttaggaagat tacgaaaaat   4800
ataaaaaata tgagttctgt gtgtataaca atgctgtaa acgccacaat tgtgtttgtt   4860
gcaaataaac ccatgattat ttgattaaaa ttgttgtttt ctttgttcat agacaatagt   4920
gtgttttgcc taaacgtgta ctgcataaac tccatgcgag tgtatagcga gctagtggct   4980
aacgcttgcc ccaccaaagt agattcgtca aaatcctcaa tttcatcacc ctcctccaag   5040
```

```
tttaacattt ggccgtcgga attaacttct aaagatgcca cataatctaa taaatgaaat      5100
agagattcaa acgtggcgtc atcgtccgtt tcgaccattt ccgaaaagaa ctcgggcata      5160
aactctatga tttctctgga cgtggtgttg tcgaaactct caaagtacgc agtcaggaac      5220
gtgcgcgaca tgtcgtcggg aaactcgcgc ggaaacatgt tgttgtaacc gaacgggtcc      5280
catagcgcca aaaccaaatc tgccagcgtc aatagaatga gcacgatgcc gacaatggag      5340
ctggcttgga tagcgattcg agttaa                                          5366

<210> SEQ ID NO 53
<211> LENGTH: 5981
<212> TYPE: DNA
<213> ORGANISM: Artificial Sequence
<220> FEATURE:
<223> OTHER INFORMATION: Recombinant expression cassette

<400> SEQUENCE: 53
ttagttgaac tcgaacttct tgtacttgca gttgagcttt tgctcggcga atgtgatggc        60
gtcggagagt ggcaccagtc cctgcaggat caaggccaag agcttcagca agttgttgtg       120
cagtgtagtt gactcgcgac ggttgacctt gccgatcacg aacatgtggt gcttgaatct       180
gttgtacttt tggatgacct ggctcacatc aacgtccttg atttcgccag agatccagta       240
gaactccttg ttcttcttag cgatggtcag ccttttcctcg ttcttgaagg acaacacgat      300
gaagttgtga cccttaacgt tatcgacgtt ttgagtcaag tactgctcaa cgatgtgcat       360
gcttccgtct tccttcttga ccttcttgag gttctcggcg ttgttgttag aagcgatgtt       420
gtcgtggtac ttgtagttgt tgaagagcag gttagcgacg gacgagtact tgtatgtcag       480
agtgctcttc ttgttcacga tgaggttcag gttatcaacg acgtacttgt tgggagggtt       540
gtccgggaat tggacggact ccgagtactt gaggatctgg gaaacgtatg gcagacgaa        600 gaagttgtta gaggcggttt cgatctcgtt tgattccttg cggctcagca tgatgggcaa       660
agtgaagagg ttcttgtcct ggtacatctc gtacaacttc gacaagagga atccacactt      720
acgctcgccg agtgattgca gcaaggtcac gaaggttgtc tgagcgtagt acatatcgag       780
gttgaagtag gaggtcagag cggccttgaa tgtgtggtgg acgtccacga agtgacactt       840
cttgcagttt tgagcggcgg tctcatcgtt gcagacgtcc tgtgagtgtg ggatttcgat       900
gccagtctcc ttaaccaggt tgtagctgat catgaagcgg atcttatcga aggtcacaac       960
gaacacacgg ttgtcaacca tgtagtagtt gtttgtgtac tcgtagacca cgttagagac      1020
gtacttggcg aagatgattt cgaaaggctt cacctcggac ttcttaacga cgaacatgta      1080
gtaaccggtt tcagacatgt gatcggagaa tctgttcgag ttgtagtcgt tatcgtcgaa      1140
cctcatcagg taggggcgaa agtcgtttgt gaagtagtga gtgatctcct gggtggaagc      1200
cactgtacag atgttagtgt tgtggttgat ggtttgttcc agtgtagcgc atgactggat      1260
ggtgctcttc ttgtacttag gtctcaactt gatcttgttg aattgaccca caactccctg      1320
ggagttatcc aggtactcgt ccaacttcct cttggtgcct gtggccgacg gctggttgac      1380
accagcagag tgttcgaagg actcggcgtg gtaagctgag ctaggagagg ttgttcgac       1440 cactggctgt tcgagtgact cgctgtagta ggcagaggac acagcttcct ccaggttgtc      1500
agtggtcttg agcagacact ccaccaaatc gttgtcagtg agcgagttaa ctgaggcgag      1560
gaagttgcta gcggcagcgg tttcagagtc ggagatgaca gtatcagctc cgtccggggt      1620
tgggtggttt tagtaagaca agtaatcgtt aggttgcttg tcgcagaact ccagagtatga     1680 gttgtcgaag ctagcacgag agggagtgct ggcagaggtg taggaagcgt tgaagttgat      1740
```

```
ttgagtcatg gtgacctggt tgttcacgat cttatcgcca cctgtgtcca cctgcagttg    1800
ctgggcctca gcgcaggctg aagtggcctc acaggagtag gggctggaag cacagttgga    1860
agtcatgatg tttcttgga cgttcaggac gtggctggat gtacggatca tagatctatc    1920
tagattcgaa agcggccgcg actagtgagc tcgtcgacgt aggcctttga attccgcgcg    1980
cttcggaccg ggatccgcgc ccgatggtgg gacggtatga ataatccgga atatttatag    2040 gttttttat tacaaaactg ttacgaaaac agtaaaatac ttatttattt gcagatggt    2100 tatcatttta attatctcca tgatctatta atattccgga gtataccta ccgtaaagcg    2160 agtttagttt tgaaaaacaa atgacatcat ttgtataatg acatcatccc ctgattgtgt    2220
tttacaagta gaattctatc cgtaaagcga gttcagtttt gaaaacaaat gagtcatacc    2280
taaacacgtt aataatcttc tgatatcagc ttatgactca agttatgagc cgtgtgcaaa    2340
acatgagata agtttatgac atcatccact gatcgtgcgt tacaagtaga attctactcg    2400
taaagccagt tcggttatga gccgtgtgca aaacatgaca tcagcttatg actcatactt    2460
gattgtgttt tacgcgtaga attctactcg taaagcgagt tcggttatga gccgtgtgca    2520
aaacatgaca tcagcttatg agtcataatt aatcgtgcgt tacaagtaga attctactcg    2580
taaagcgagt tgaaggatca tatttagttg cgtttatgag ataagattga aagcacgtgt    2640
aaaatgtttc cgagctcgtc gacgtaggcc tttgaattcc gcgcgcttcg gacgggatc    2700 ggtaccaaat tccgttttgc gacgatgcag agttttgaa caggctgctc aaacacatag    2760
atccgtaccc gctcagtcgg atgtattaca atgcagccaa taccatgttt tacacgacta    2820
tggaaaacta tgccgtgtcc aattgcaagt tcaacattga ggattacaat aacatattta    2880
aggtgatgga aaatattagg aaacacagca acaaaaattc aaacgaccaa gacgagttaa    2940
acatatattt gggagttcag tcgtcgaatg caaagcgtaa aaaatattaa taaggtaaaa    3000
attacagcta cataaattac acaatttaaa ctgcagtctg gagatacgga cctttaattc    3060
aacccaacac aatatattat agttaaataa gaattattat caaatcattt gtatattaat    3120
taaaatacta tactgtaaat tacatttat ttacaatcac tcgacctcga gatggagggc    3180
aaagcccgca cagcgccgca aggcgaagca gcaggcactg ccaccacagc atcagtccct    3240
ggaaccacaa ccgatggcat ggaccccggc gttgtggcca ctaccagcgt ggtcactgca    3300
gagaattcat ccgcatcgat tgcaacggca gggattggcg gaccacccca acaggtggac    3360
caacaagaga catggagaac gaacttttat tataatgacg ttttcacttg gtcagtcgcg    3420
gatgcccctg gcagcatact ttacaccgtt caacattctc cacagaacaa cccattcaca    3480
gccgtgctga gccagatgta tgctggctgg gctggtggca tgcagtttcg cttcatagtt    3540
gccggatcgt gtgtgtttgg tgggcggttg gttgcgccg tgataccacc gggcatcgag    3600
attggaccag gctggaggt caggcaattc ccccatgttg tcatcgacgc tcgttcactt    3660
gaacctgtca ccatcaccat gccagacttg cgtcccaaca tgtaccatcc aactggtgac    3720
cctggccttg ttcccacact agtccttagt gtttataaca acctcatcaa cccgtttggt    3780
gggtccacca gcgcaatcca ggtgacagtg gaaacaaggc caagtgaaga tttttgagttc    3840 gtgatgattc gagcccctc cagcaagact gttgactcaa tttcacccgc aggcctcctc    3900
acgaccccag tcctcactgg ggttggcaat gacaacaggt ggaatggcca aatagtggga    3960
ctgcaaccag tacctggagg gttctctacg tgcaacaggc attggaactt gaatggcagc    4020
acatatggct ggtcaagccc ccggttgcc gacattgacc atcgaagagg cagtgcaagt    4080
```

```
tacccectggat ccaacgcaac caacgtgctt cagttttggt atgccaatgc tgggtctgca    4140
atcgacaatc ccatctccca ggttgcacca gacggctttc ctgatatgtc gttcgtgccc    4200
tttaacggcc ctggcattcc agccgcgggg tgggtcggat ttggtgcaat ctggaacagt    4260
aacagcggtg cccccaacgt tacgactgtg caggcttatg agttaggttt tgccactggg    4320
gcaccaggca acctccagcc caccaccaac acttcaggtt cacagactgt cgccaagtcc    4380
atatatgccg tggtaactgg cacagcccaa aaccccgccg gattgtttgt gatggcctcg    4440
ggtgttatct ccaccccaag tgccaacgcc atcacataca cgccccaacc agacagaatt    4500
gtaaccacac ccggcactcc tgccgctgca cctgtgggta agaacacacc catcatgttc    4560
gcgtctgtcg tcaggcgcac cggtgacgtc aacgccacag ctgggtcagc taacgggacc    4620
cagtacggca caggctctca accactgcca gtaacaattg actttcgct caacaactac    4680
tcgtcagcac ttatgcccgg acagtttttc gtttggcagt taacctttgc atctggtttc    4740
atggagattg gtttaagtgt ggacgggtat tttatgcag gaacaggagc ctcaaccaca    4800
ctcattgact tgactgaact cattgacgta cgccctgtgg gacccaggcc atccaagagc    4860
acactcgtgt tcaacctggg gggcacagcc aatggctttt cttatgtctg aattcatcgg    4920
actgggactt gcaggtgcca gcgttttgag caatgcattg ctccgcaggc aagagctgca    4980
actacaaaga caagctttgg agaatggggtt ggttttgaaa gccgaccaat taggtaggtt    5040
aggttttaat ccaaatgaag ttaagaatgt gattgtaggg aatagtttta gtagtaatgt    5100
tagattaagt aatatgcata atgatgctag tgtagttaat gcttataatg tgtataatcc    5160
tgccagcaat ggcatcagaa agaaaattaa gagtttgaat aatagtgtta agatttataa    5220
caccactggg gagtccagtg tttaatttga ttttattggt tttgaaattt ggtttaattg    5280
ggtttatagt ttaaagtaag ctatccatgg aagcttatga atcgttttta aaataacaaa    5340
tcaattgttt tataatattc gtacgattct ttgattatgt aataaaatgt gatcattagg    5400
aagattacga aaaatataaa aaatatgagt tctgtgtgta taacaaatgc tgtaaacgcc    5460
acaattgtgt ttgttgcaaa taaacccatg attatttgat taaaattgtt gttttctttg    5520
ttcatagaca atagtgtgtt ttgcctaaac gtgtactgca taaactccat gcgagtgtat    5580
agcgagctag tggctaacgc ttgccccacc aaagtagatt cgtcaaaatc ctcaatttca    5640
tcaccctcct ccaagtttaa catttggccg tcggaattaa cttctaaaga tgccacataa    5700
tctaataaat gaaatagaga ttcaaacgtg gcgtcatcgt ccgtttcgac catttccgaa    5760
aagaactcgg gcataaactc tatgatttct ctggacgtgg tgttgtcgaa actctcaaag    5820
tacgcagtca ggaacgtgcg cgacatgtcg tcgggaaact cgcgcggaaa catgttgttg    5880
taaccgaacg ggtcccatag cgccaaaacc aaatctgcca gcgtcaatag aatgagcacg    5940
atgccgacaa tggagctggc ttggatagcg attcgagtta a                        5981
```

<210> SEQ ID NO 54
<211> LENGTH: 4961
<212> TYPE: DNA
<213> ORGANISM: Artificial Sequence
<220> FEATURE:
<223> OTHER INFORMATION: Recombinant expression cassette

<400> SEQUENCE: 54

```
ttagttgaac tcgaacttct tgtacttgca gttgagcttt tgctcggcga atgtgatggc      60
gtcggagagt ggcaccagtc cctgcaggat caaggccaag agcttcagca agttgttgtg     120
cagtgtagtt gactcgcgac ggttgacctt gccgatcacg aacatgtggt gcttgaatct     180
```

```
gttgtacttt tggatgacct ggctcacatc aacgtccttg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactt gaggatctgg gaaacgtatg gcgagacgaa    600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
cttgcagttt tgagcggcgg tctcatcgtt gcagacgtcc tgtgagtgtg ggatttcgat    900
gccagtctcc ttaaccaggt tgtagctgat catgaagcgg atcttatcga aggtcacaac    960
gaacacacgg ttgtcaacca tgtagtagtt gtttgtgtac tcgtagacca cgttagagac   1020
gtacttggcg aagatgattt cgaaaggctt cacctcggac ttcttaacga cgaacatgta   1080
gtaaccggtt tcagacatgt gatcggagaa tctgttcgag ttgtagtcgt tatcgtcgaa   1140
cctcatcagg taggggcga agtcgtttgt gaagtagtga gtgatctcct gggtggaagc   1200
cactgtacag atgttagtgt tgtggttgat ggtttgttcc agtgtagcgc atgactggat   1260
ggtgctcttc ttgtacttag gtctcaactt gatcttgttg aattgaccca caactccctg   1320
ggagttatcc aggtactcgt ccaacttcct cttggtgcct gtggccgacg gctggttgac   1380
accagcagag tgttcgaagg actcggcgtg gtaagctgag ctaggagagg gttgttcgac   1440
cactggctgt tcgagtgact cgctgtagta ggcagaggac acagcttcct ccaggttgtc   1500
agtggtcttg agcagacact ccaccaaatc gttgtcagtg agcgagttaa ctgaggcgag   1560
gaagttgcta gcggcagcgg tttcagagtc ggagatgaca gtatcagctc cgtccgggt   1620 tgggtggttg tagtaagaca agtaatcgtt aggttgcttg tcgcagaact ccgagtatga   1680
gttgtcgaag ctagcacgag agggagtgct ggcagaggtg taggaagcgt tgaagttgat   1740
ttgagtcatg gtgacctggt tgttcacgat cttatcgcca cctgtgtcca cctgcagttg   1800
ctgggcctca gcgcaggctg aagtggcctc acaggagtag gggctggaag cacagttgga   1860
agtcatgatg ttttcttgga cgttcaggac gtggctggat gtacggatca tagatctatc   1920
tagattcgaa agcggccgcg actagtgagc tcgtcgacgt aggcctttga attccgcgcg   1980
cttcggaccg ggatccgcgc ccgatggtgg gacggtatga ataatccgga atatttatag   2040 gttttttat tacaaaactg ttacgaaaac agtaaaatac ttatttattt gcgagatggt   2100
tatcatttta attatctcca tgatctatta atattccgga gtatacctac ccgtaaagcg   2160
agtttagttt tgaaaaacaa atgacatcat ttgtataatg acatcatccc ctgattgtgt   2220
tttacaagta gaattctatc cgtaaagcga gttcagtttt gaaaacaaat gagtcatacc   2280
taaacacgtt aataatcttc tgatatcagc ttatgactca agttatgagc cgtgtgcaaa   2340
acatgagata agtttatgac atcatccact gatcgtgcgt tacaagtaga attctactcg   2400
taaagccagt tcggttatga gccgtgtgca aaacatgaca tcagcttatg actcatactt   2460
gattgtgttt tacgcgtaga attctactcg taaagcgagt tcggttatga gccgtgtgca   2520
```

```
aaacatgaca tcagcttatg agtcataatt aatcgtgcgt tacaagtaga attctactcg    2580
taaagcgagt tgaaggatca tatttagttg cgtttatgag ataagattga aagcacgtgt    2640
aaaatgtttc cgagctcgtc gacgtaggcc tttgaattcc gcgcgcttcg gaccgggatc    2700
ggtaccaaat tccgttttgc gacgatgcag agttttttgaa caggctgctc aaacacatag    2760
atccgtaccc gctcagtcgg atgtattaca atgcagccaa taccatgttt tacacgacta    2820
tggaaaacta tgccgtgtcc aattgcaagt tcaacattga ggattacaat aacatattta    2880
aggtgatgga aaatattagg aaacacagca acaaaaattc aaacgaccaa gacgagttaa    2940
acatatattt gggagttcag tcgtcgaatg caaagcgtaa aaaatattaa taaggtaaaa    3000
attacagcta cataaattac acaatttaaa ctgcagtctg gagatacgga cctttaattc    3060
aacccaacac aatatattat agttaaataa gaattattat caaatcattt gtatattaat    3120
taaaatacta tactgtaaat tacattttat ttacaatcac tcgacctcga gatgtctctt    3180
tggctgccta gcgaggccac tgtctacttg cctcctgtcc cagtatctaa agttgtaagc    3240
acggatgaat atgttgcacg cacaaacata tattatcatg caggaacatc cagactactt    3300
gcagttggac atccctattt tcctattaaa aaacctaaca ataacaaaat attagttcct    3360
aaagtatcag gattacaata cagggtattt agaatatatt tacctgaccc caataagttt    3420
ggttttcctg acacctcatt ttacaatcca gatacacagc ggctggtttg ggcctgtgta    3480
ggtgttgagg taggccgtgg tcagccatta ggtgtgggca ttagtggcca tcctttatta    3540
aataaattgg atgacacaga aaatgctagt gcttatgcag caaatgcagg tgtggataat    3600
agagaatgta tatctatgga ttacaaacaa acacaattgt gtttaattgg ttgcaaacca    3660
cctataggg aacactgggg caaaggatcc ccatgtaaca atgttgcagt aaatccaggt    3720
gattgtccac cattagagtt aataaacaca gttattcagg atggtgatat ggttgatacc    3780
ggctttggtg ctatggactt tactacatta caggctaaca aaagtgaagt tccactggat    3840
atttgtacgt ctatttgcaa atatccagat tatattaaaa tggtgtcaga accatatggc    3900
gacagcttat tttttattt acgaagggaa caaatgtttg ttagacattt atttaatagg    3960
gctggtgctg ttggtgaaaa tgtaccagac gattttataca ttaaaggctc tgggtctact    4020
gcaaatttag ccagttcaaa ttattttcct acacctagtg gttctatggt tacctctgat    4080
gcccaaatat ttaataaacc atattggtta caacgagcac agggccacaa taatggtatt    4140
tgttggggta accaactatt tgttactgtt gttgatacta cacgcagtac aaatatgtca    4200
ttatgtgctg ccatatctac ttcagaaact acatataaaa atactaactt taaagagtac    4260
ctacgacatg gggaggaata tgatttacag tttatttttc aactgtgcaa aataaccta    4320
actgcagacg ttatgacata catacattct atgaattcca ctatttggga ggactggaat    4380
tttggtttac aacctccccc aggaggcaca ctagaagata cttataggtt tgtaacatcc    4440
caggcaattg cttgtcaaaa acatacacct ccagcaccta agaagatcc ccttaaaaaa    4500
tatactttt gggaagtaaa tttaaaagaa aagttttctg cagacctaga tcagttcct    4560
ttaggacgca aattttttact acaagcagga tttaaggcca aaccaaaatt tacattagga    4620
aaacgaaaag ctacacccac cacctcatct acctctacaa ctgctaaacg caaaaaacgt    4680
aagctgtaaa agcttcagct ggtcgagaag tactagagga tcataatcag ccataccaca    4740
tttgtagagg ttttacttgc tttaaaaaac ctcccacacc tccccctgaa cctgaaacat    4800
aaaatgaatg caattgttgt tgttaacttg tttattgcag cttataatgg ttacaaataa    4860
agcaatagca tcacaaattt cacaaataaa gcattttttt cactgcattc tagttgtggt    4920
```
ttgtccaaac tcatcaatgt atcttatcat gtctggatct g         4961

<210> SEQ ID NO 55
<211> LENGTH: 5576
<212> TYPE: DNA
<213> ORGANISM: Artificial Sequence
<220> FEATURE:
<223> OTHER INFORMATION: Recombinant expression cassette

<400> SEQUENCE: 55

| | | | | |
|---|---|---|---|---|
| ttagttgaac | tcgaacttct | tgtacttgca | gttgagcttt | tgctcggcga atgtgatggc |     60 |
| gtcggagagt | ggcaccagtc | cctgcaggat | caaggccaag | agcttcagca agttgttgtg |    120 |
| cagtgtagtt | gactcgcgac | ggttgacctt | gccgatcacg | aacatgtggt gcttgaatct |    180 |
| gttgtacttt | tggatgacct | ggctcacatc | aacgtccttg | atttcgccag agatccagta |    240 |
| gaactccttg | ttcttcttag | cgatggtcag | cctttcctcg | ttcttgaagg acaacacgat |    300 |
| gaagttgtga | cccttaacgt | tatcgacgtt | ttgagtcaag | tactgctcaa cgatgtgcat |    360 |
| gcttccgtct | tccttcttga | ccttcttgag | gttctcggcg | ttgttgttag aagcgatgtt |    420 |
| gtcgtggtac | ttgtagttgt | tgaagagcag | gttagcgacg | gacgagtact tgtatgtcag |    480 |
| agtgctcttc | ttgttcacga | tgaggttcag | gttatcaacg | acgtacttgt tgggagggtt |    540 |
| gtccgggaat | tggacggact | ccgagtactt | gaggatctgg | gaaacgtatg gcagacgaa |    600 |
| gaagttgtta | gaggcggttt | cgatctcgtt | tgattccttg | cggctcagca tgatgggcaa |    660 |
| agtgaagagg | ttcttgtcct | ggtacatctc | gtacaacttc | gacaagagga atccacactt |    720 |
| acgctcgccg | agtgattgca | gcaaggtcac | gaaggttgtc | tgagcgtagt acatatcgag |    780 |
| gttgaagtag | gaggtcagag | cggccttgaa | tgtgtggtgg | acgtccacga agtgacactt |    840 |
| cttgcagttt | tgagcggcgg | tctcatcgtt | gcagacgtcc | tgtgagtgtg ggatttcgat |    900 |
| gccagtctcc | ttaaccaggt | tgtagctgat | catgaagcgg | atcttatcga aggtcacaac |    960 |
| gaacacacgg | ttgtcaacca | tgtagtagtt | gtttgtgtac | tcgtagacca cgttagagac |   1020 |
| gtacttggcg | aagatgattt | cgaaaggctt | cacctcggac | ttcttaacga cgaacatgta |   1080 |
| gtaaccggtt | tcagacatgt | gatcggagaa | tctgttcgag | ttgtagtcgt tatcgtcgaa |   1140 |
| cctcatcagg | taggggcga | agtcgtttgt | gaagtagtga | gtgatctcct gggtggaagc |   1200 |
| cactgtacag | atgttagtgt | tgtggttgat | ggtttgttcc | agtgtagcgc atgactggat |   1260 |
| ggtgctcttc | ttgtacttag | gtctcaactt | gatcttgttg | aattgaccca caactccctg |   1320 |
| ggagttatcc | aggtactcgt | ccaacttcct | cttggtgcct | gtggccgacg gctggttgac |   1380 |
| accagcagag | tgttcgaagg | actcggcgtg | gtaagctgag | ctaggagagg ttgttcgac |   1440 |
| cactggctgt | tcgagtgact | cgctgtagta | ggcagaggac | acagcttcct ccaggttgtc |   1500 |
| agtggtcttg | agcagacact | ccaccaaatc | gttgtcagtg | agcgagttaa ctgaggcgag |   1560 |
| gaagttgcta | gcggcagcgg | tttcagagtc | ggagatgaca | gtatcagctc cgtccgggt |   1620 |
| tgggtggttg | tagtaagaca | agtaatcgtt | aggttgcttg | tcgcagaact ccgagtatga |   1680 |
| gttgtcgaag | ctagcacgag | agggagtgct | ggcagaggtg | taggaagcgt tgaagttgat |   1740 |
| ttgagtcatg | gtgacctggt | tgttcacgat | cttatcgcca | cctgtgtcca cctgcagttg |   1800 |
| ctgggcctca | gcgcaggctg | aagtggcctc | acaggagtag | gggctggaag cacagttgga |   1860 |
| agtcatgatg | ttttcttgga | cgttcaggac | gtggctggat | gtacggatca tagatctatc |   1920 |
| tagattcgaa | agcggccgcg | actagtgagc | tcgtcgacgt | aggcctttga attccgcgcg |   1980 |

```
cttcggaccg ggatccgcgc ccgatggtgg gacggtatga ataatccgga atatttatag   2040 gttttttat tacaaaactg ttacgaaaac agtaaaatac ttatttattt gcgagatggt    2100
tatcatttta attatctcca tgatctatta atattccgga gtataccta ccgtaaagcg    2160 agtttagttt tgaaaaacaa atgacatcat ttgtataatg acatcatccc ctgattgtgt   2220
tttacaagta gaattctatc cgtaaagcga gttcagtttt gaaaacaaat gagtcatacc   2280
taaacacgtt aataatcttc tgatatcagc ttatgactca agttatgagc cgtgtgcaaa   2340
acatgagata agtttatgac atcatccact gatcgtgcgt tacaagtaga attctactcg   2400
taaagccagt tcggttatga gccgtgtgca aaacatgaca tcagcttatg actcatactt   2460
gattgtgttt tacgcgtaga attctactcg taaagcgagt tcggttatga gccgtgtgca   2520
aaacatgaca tcagcttatg agtcataatt aatcgtgcgt tacaagtaga attctactcg   2580
taaagcgagt tgaaggatca tatttagttg cgtttatgag ataagattga aagcacgtgt   2640
aaaatgtttc cgagctcgtc gacgtaggcc tttgaattcc gcgcgcttcg gaccgggatc   2700
ggtaccaaat tccgttttgc gacgatgcag agttttgaa caggctgctc aaacacatag    2760
atccgtaccc gctcagtcgg atgtattaca atgcagccaa taccatgttt tacacgacta   2820
tggaaaacta tgccgtgtcc aattgcaagt tcaacattga ggattacaat aacatattta   2880
aggtgatgga aaatattagg aaacacagca acaaaaattc aaacgaccaa gacgagttaa   2940
acatatattt gggagttcag tcgtcgaatg caaagcgtaa aaaatattaa taaggtaaaa    3000
attacagcta cataaattac acaatttaaa ctgcagtctg gagatacgga cctttaattc   3060
aacccaacac aatatattat agttaaataa gaattattat caaatcattt gtatattaat   3120
taaaatacta tactgtaaat tacatttat ttacaatcac tcgacctcga gatggagggc    3180
aaagcccgca cagcgccgca aggcgaagca gcaggcactg ccaccacagc atcagtccct   3240
ggaaccacaa ccgatggcat ggaccccggc gttgtggcca ctaccagcgt ggtcactgca   3300
gagaattcat ccgcatcgat tgcaacggca gggattggcg gaccacccca acaggtggac   3360
caacaagaga catggagaac gaacttttat tataatgacg ttttcacttg gtcagtcgcg   3420 gatgccctg gcagcatact ttacaccgtt caacattctc cacagaacaa cccattcaca    3480
gccgtgctga gccagatgta tgctggctgg gctggtggca tgcagtttcg cttcatagtt   3540
gccggatcgg gtgtgtttgg tgggcggttg gttgcggccg tgataccacc gggcatcgag   3600
attggaccag ggctggaggt caggcaattc ccccatgttg tcatcgacgc tcgttcactt   3660
gaacctgtca ccatcaccat gccagacttg cgtcccaaca tgtaccatcc aactggtgac   3720
cctggccttg ttcccacact agtccttagt gtttataaca acctcatcaa cccgtttggt   3780
gggtccacca gcgcaatcca ggtgacagtg gaaacaaggc caagtgaaga ttttgagttc   3840
gtgatgattc gagcccctc cagcaagact gttgactcaa tttcacccgc aggcctcctc    3900
acgaccccag tcctcactgg ggttggcaat gacaacaggt ggaatggcca aatagtggga   3960
ctgcaaccag tacctggagg gttctctacg tgcaacaggc attggaactt gaatggcagc   4020
acatatggct ggtcaagccc ccggtttgcc gacattgacc atcgaagagg cagtgcaagt   4080
taccctggat ccaacgcaac caacgtgctt cagttttggt atgccaatgc tgggtctgca   4140
atcgacaatc ccatctccca ggttgcacca gacggctttc ctgatatgtc gttcgtgccc   4200
tttaacggcc ctggcattcc agccgcgggg tgggtcggat ttggtgcaat ctggaacagt   4260
aacagcggtg cccccaacgt tacgactgtg caggcttatg agttaggttt tgccactggg   4320
gcaccaggca acctccagcc caccaccaac acttcaggtt cacagactgt cgccaagtcc   4380
```

```
atatatgccg tggtaactgg cacagcccaa aaccccgccg gattgtttgt gatggcctcg    4440
ggtgttatct ccaccccaag tgccaacgcc atcacataca cgccccaacc agacagaatt    4500
gtaaccacac ccggcactcc tgccgctgca cctgtgggta agaacacacc catcatgttc    4560
gcgtctgtcg tcaggcgcac cggtgacgtc aacgccacag ctgggtcagc taacgggacc    4620
cagtacggca caggctctca accactgcca gtaacaattg gactttcgct caacaactac    4680
tcgtcagcac ttatgcccgg acagtttttc gtttggcagt taacctttgc atctggtttc    4740
atggagattg gtttaagtgt ggacgggtat ttttatgcag gaacaggagc ctcaaccaca    4800
ctcattgact tgactgaact cattgacgta cgccctgtgg gacccaggcc atccaagagc    4860
acactcgtgt tcaacctggg gggcacagcc aatggctttt cttatgtctg aattcatcgg    4920
actgggactt gcaggtgcca gcgttttgag caatgcattg ctccgcaggc aagagctgca    4980
actacaaaga caagctttgg agaatgggtt ggttttgaaa gccgaccaat taggtaggtt    5040
aggttttaat ccaaatgaag ttaagaatgt gattgtaggt aatagtttta gtagtaatgt    5100
tagattaagt aatatgcata atgatgctag tgtagttaat gcttataatg tgtataatcc    5160
tgccagcaat ggcatcagaa agaaaattaa gagtttgaat aatagtgtta agatttataa    5220
caccactggg gagtccagtg tttaatttga ttttattggt tttgaaattt ggtttaattg    5280
ggtttatagt ttaaagtaag ctataagctt cagctggtcg agaagtacta gaggatcata    5340
atcagccata ccacatttgt agaggtttta cttgctttaa aaaacctccc acacctcccc    5400
ctgaacctga aacataaaat gaatgcaatt gttgttgtta acttgtttat tgcagcttat    5460
aatggttaca aataaagcaa tagcatcaca aatttcacaa ataaagcatt tttttcactg    5520
cattctagtt gtggtttgtc caaactcatc aatgtatctt atcatgtctg gatctg        5576
```

<210> SEQ ID NO 56
<211> LENGTH: 4145
<212> TYPE: DNA
<213> ORGANISM: Artificial Sequence
<220> FEATURE:
<223> OTHER INFORMATION: Recombinant expression cassette

<400> SEQUENCE: 56

```
ttagttgaac tcgaacttct tgtacttgca gttgagcttt tgctcggcga atgtgatggc      60
gtcggagagt ggcaccagtc cctgcaggat caaggcaag agcttcagca agttgttgtg     120
cagtgtagtt gactcgcgac ggttgacctt gccgatcacg aacatgtggt gcttgaatct    180
gttgtacttt tggatgacct ggctcacatc aacgtccttg atttcgccag agatccagta    240
gaactccttg ttcttcttag cgatggtcag cctttcctcg ttcttgaagg acaacacgat    300
gaagttgtga cccttaacgt tatcgacgtt ttgagtcaag tactgctcaa cgatgtgcat    360
gcttccgtct tccttcttga ccttcttgag gttctcggcg ttgttgttag aagcgatgtt    420
gtcgtggtac ttgtagttgt tgaagagcag gttagcgacg gacgagtact tgtatgtcag    480
agtgctcttc ttgttcacga tgaggttcag gttatcaacg acgtacttgt tgggagggtt    540
gtccgggaat tggacggact ccgagtactg gaggatctgg gaaacgtatg gcgagacgaa    600
gaagttgtta gaggcggttt cgatctcgtt tgattccttg cggctcagca tgatgggcaa    660
agtgaagagg ttcttgtcct ggtacatctc gtacaacttc gacaagagga atccacactt    720
acgctcgccg agtgattgca gcaaggtcac gaaggttgtc tgagcgtagt acatatcgag    780
gttgaagtag gaggtcagag cggccttgaa tgtgtggtgg acgtccacga agtgacactt    840
```

-continued

```
cttgcagttt tgagcggcgg tctcatcgtt gcagacgtcc tgtgagtgtg ggatttcgat      900
gccagtctcc ttaaccaggt tgtagctgat catgaagcgg atcttatcga aggtcacaac      960
gaacacacgg ttgtcaacca tgtagtagtt gtttgtgtac tcgtagacca cgttagagac     1020
gtacttggcg aagatgattt cgaaaggctt cacctcggac ttcttaacga cgaacatgta     1080
gtaaccggtt tcagacatgt gatcggagaa tctgttcgag ttgtagtcgt tatcgtcgaa     1140
cctcatcagg taggggcga agtcgtttgt gaagtagtga gtgatctcct gggtggaagc     1200
cactgtacag atgttagtgt tgtggttgat ggtttgttcc agtgtagcgc atgactggat     1260
ggtgctcttc ttgtacttag gtctcaactt gatcttgttg aattgaccca caactccctg     1320
ggagttatcc aggtactcgt ccaacttcct cttggtgcct gtggccgacg gctggttgac     1380
accagcagag tgttcgaagg actcggcgtg gtaagctgag ctaggagagg gttgttcgac     1440
cactggctgt tcgagtgact cgctgtagta ggcagaggac acagcttcct ccaggttgtc     1500
agtggtcttg agcagacact ccaccaaatc gttgtcagtg agcgagttaa ctgaggcgag     1560
gaagttgcta gcggcagcgg tttcagagtc ggagatgaca gtatcagctc cgtccggggt     1620
tgggtggttg tagtaagaca agtaatcgtt aggttgcttg tcgcagaact ccgagtatga     1680
gttgtcgaag ctagcacgag agggagtgct ggcagaggtg taggaagcgt tgaagttgat     1740
ttgagtcatg gtgacctggt tgttcacgat cttatcgcca cctgtgtcca cctgcagttg     1800
ctgggcctca gcgcaggctg aagtggcctc acaggagtag gggctggaag cacagttgga     1860
agtcatgatg ttttcttgga cgttcaggac gtggctggat gtacggatca tagatctatc     1920
tagattcgaa agcggccgcg actagtgagc tcgtcgacgt aggcctttga attccgcgcg     1980
cttcggaccg ggatccgcgc ccgatggtgg gacggtatga ataatccgga atatttatag     2040
gttttttttat tacaaaactg ttacgaaaac agtaaaatac ttatttattt gcagagatggt     2100
tatcatttta attatctcca tgatctatta atattccgga gtataccta ccgtaaagcg      2160
agtttagttt tgaaaaacaa atgacatcat ttgtataatg acatcatccc ctgattgtgt     2220
tttacaagta gaattctatc cgtaaagcga gttcagtttt gaaaacaaat gagtcatacc     2280
taaacacgtt aataatcttc tgatatcagc ttatgactca agttatgagc cgtgtgcaaa     2340
acatgagata agtttatgac atcatccact gatcgtgcgt tacaagtaga attctactcg     2400
taaagccagt tcggttatga gccgtgtgca aaacatgaca tcagcttatg actcatactt     2460
gattgtgttt tacgcgtaga attctactcg taaagcgagt tcggttatga gccgtgtgca     2520
aaacatgaca tcagcttatg agtcataatt aatcgtgcgt tacaagtaga attctactcg     2580
taaagcgagt tgaaggatca tatttagttg cgtttatgag ataagattga aagcacgtgt     2640
aaaatgtttc cgagctcgtc gacgtaggcc tttgaattcc gcgcgcttcg gacccgggatc    2700
ggtaccaaat tccgttttgc gacgatgcag agttttgaa caggctgctc aaacacatag      2760
atccgtaccc gctcagtcgg atgtattaca atgcagccaa taccatgttt tacacgacta     2820
tggaaaacta tgccgtgtcc aattgcaagt tcaacattga ggattacaat aacatatttta    2880
aggtgatgga aaatattagg aaacacagca acaaaaattc aaacgaccaa gacgagttaa     2940
acatatattt gggagttcag tcgtcgaatg caaagcgtaa aaaatattaa taaggtaaaa     3000
attacagcta cataaattac acaatttaaa ctgcagtctg gagatacgga cctttaattc     3060
aacccaacac aatatattat agttaaataa gaattattat caaatcattt gtatattaat     3120
taaaatacta tactgtaaat tacattttat ttacaatcac tcgacctcga gatgacgtat     3180
ccaaggaggc gtttccgcag acgaagacac cgccccgca gccatcttgg ccagatcctc       3240
```

```
cgccgccgcc cctggctcgt ccaccccgc caccgttacc gctggagaag gaaaaatggc      3300
atcttcaaca cccgcctctc ccgcaccttc ggatatactg tcaaggctac cacagtcaca      3360
acgccctcct gggcggtgga catgatgaga tttaatatta acgactttgt tcccccggga      3420 gggggacca acaaaatctc tatacccttt gaatactaca gaataagaaa ggttaaggtt      3480
gaattctggc cctgctcccc aatcacccag ggtgacaggg gagtgggctc cactgctgtt      3540
attctagatg ataactttgt aacaaaggcc acagccctaa cctatgaccc ctatgtaaac      3600
tactcctccc gccatacaat cccccaaccc ttctcctacc actcccgtta cttcacaccc      3660
aaacctgtac tggatagaac tattgattac ttccagccaa acaacaaaaa aaatcagctt      3720
tggctgaggc tacaaacctc tgcaaatgta gaccacgtag gcctcggcac tgcgttcgaa      3780
aacagtaaat acgaccagga ctacaatatc cgtgtaacca tgtatgtaca attcagagaa      3840
tttaatctta aagacccccc acttaaaccc taaaagcttc agctggtcga gaagtactag      3900
aggatcataa tcagccatac cacatttgta gaggttttac ttgctttaaa aaacctccca      3960
cacctccccc tgaacctgaa acataaaatg aatgcaattg ttgttgttaa cttgtttatt      4020
gcagcttata atggttacaa ataaagcaat agcatcacaa atttcacaaa taaagcattt      4080
ttttcactgc attctagttg tggtttgtcc aaactcatca atgtatctta tcatgtctgg      4140
atctg                                                                4145
```